US010961307B2

(12) United States Patent
Johanns et al.

(10) Patent No.: US 10,961,307 B2
(45) Date of Patent: Mar. 30, 2021

(54) METHODS OF TREATING MODERATELY TO SEVERELY ACTIVE ULCERATIVE COLITIS BY ADMINISTERING AN ANTI-IL12/IL23 ANTIBODY

(71) Applicant: Janssen Biotech, Inc., Horsham, PA (US)

(72) Inventors: Jewel Johanns, Devon, PA (US); Katherine Li, Wallingford, PA (US); Colleen Marano, Malvern, PA (US); Richard Strauss, Doylestown, PA (US); Hongyan Zhang, Malvern, PA (US); Christopher O'Brien, Lafayette Hill, PA (US); Omoniyi Adedokun, Phoenixville, PA (US); Kimberly Shields-Tuttle, West Chester, PA (US)

(73) Assignee: Janssen Biotech, Inc., Horsham, PA (US)

(*) Notice: Subject to any disclaimer, the term of this patent is extended or adjusted under 35 U.S.C. 154(b) by 0 days.

(21) Appl. No.: 16/580,509

(22) Filed: Sep. 24, 2019

(65) Prior Publication Data

US 2020/0095315 A1 Mar. 26, 2020

Related U.S. Application Data

(60) Provisional application No. 62/895,774, filed on Sep. 4, 2019, provisional application No. 62/769,818, filed on Nov. 20, 2018, provisional application No. 62/735,501, filed on Sep. 24, 2018.

(51) Int. Cl.

| | | |
|---|---|---|
| *A61K 39/00* | (2006.01) | |
| *C07K 16/24* | (2006.01) | |
| *A61K 9/08* | (2006.01) | |
| *A61K 47/22* | (2006.01) | |
| *A61K 47/26* | (2006.01) | |
| *A61K 47/18* | (2017.01) | |
| *A61P 1/04* | (2006.01) | |
| *A61K 9/00* | (2006.01) | |

(52) U.S. Cl.
CPC .......... *C07K 16/244* (2013.01); *A61K 9/0019* (2013.01); *A61K 9/08* (2013.01); *A61K 39/00* (2013.01); *A61K 47/183* (2013.01); *A61K 47/22* (2013.01); *A61K 47/26* (2013.01); *A61P 1/04* (2018.01); *A61K 2039/505* (2013.01); *A61K 2039/54* (2013.01); *A61K 2039/545* (2013.01); *C07K 2317/31* (2013.01); *C07K 2317/565* (2013.01)

(58) Field of Classification Search
CPC .............. C07K 16/244; C07K 2317/21; C07K 2317/31; C07K 2317/565; C07K 2317/76; A61K 9/0019; A61K 9/08; A61K 47/22; A61K 47/26; A61K 47/183; A61K 2039/505; A61K 2039/54; A61K 2039/545; A61P 1/04
See application file for complete search history.

(56) References Cited

U.S. PATENT DOCUMENTS

| | | |
|---|---|---|
| 5,457,038 A | 10/1995 | Trinchieri et al. |
| 5,547,852 A | 8/1996 | Seller et al. |
| 5,648,467 A | 7/1997 | Trinchieri et al. |
| 5,780,597 A | 7/1998 | Gately et al. |
| 5,811,523 A | 9/1998 | Trinchieri et al. |
| 5,891,680 A | 4/1999 | Lieschke et al. |
| 6,086,876 A | 7/2000 | Karp et al. |
| 6,225,117 B1 | 5/2001 | Gately et al. |
| 6,300,478 B1 | 10/2001 | Trinchieri et al. |
| 6,338,848 B1 | 1/2002 | Leonard et al. |
| 6,495,667 B1 | 12/2002 | Bazan |
| 6,902,734 B2 | 6/2005 | Giles-Komar et al. |
| 6,914,128 B1 | 7/2005 | Salfeld et al. |
| 7,063,964 B2 | 6/2006 | Giles-Komar et al. |
| 7,166,285 B2 | 7/2007 | Giles-Komar et al. |
| 7,279,157 B2 | 10/2007 | Giles-Komar et al. |
| 7,560,247 B2 | 7/2009 | Giles-Komar et al. |
| 7,887,807 B2 | 2/2011 | Giles-Komar et al. |
| 8,084,233 B2 | 12/2011 | Giles-Komar et al. |
| 8,329,171 B2 | 12/2012 | Giles-Komar et al. |
| 8,703,141 B2 | 4/2014 | Giles-Komar et al. |
| 9,409,984 B2 | 8/2016 | Giles-Komar et al. |
| 9,676,848 B2 | 6/2017 | Giles-Komar et al. |
| 10,259,867 B2 | 4/2019 | Giles-Komar et al. |
| 10,519,231 B2 | 12/2019 | Giles-Komar et al. |

(Continued)

FOREIGN PATENT DOCUMENTS

| | | |
|---|---|---|
| CL | 688-2000 | 3/2000 |
| EP | 0640689 A2 | 3/1995 |

(Continued)

OTHER PUBLICATIONS https://www.ema.europa.eu/en/medicines/human/EPAR/stelara. Accessed from the internet Jul. 13, 2020. Date provided by Google search—Jan. 15, 2009.*
https://clinicaltrials.gov/ct2/show/NCT02407236. Accessed from the internet Jul. 13, 2020.*
Adedokun, et al, "Ustekinumab Pharmacokinetics and Exposure Response in a Phase 3 Randomized Trial of Patients with Ulcerative Colitis," Clinical Gastroenterology and Hepatology, 18: 2244-2255 (2020).

(Continued)

*Primary Examiner* — Robert S Landsman
(74) *Attorney, Agent, or Firm* — Eric Dichter

(57) ABSTRACT

Described are methods and compositions for clinical proven safe and effective treatment of ulcerative colitis, particularly moderately to severely active ulcerative colitis in patients who have had an inadequate response to or are intolerant of a conventional or existing therapy by intravenous and/or subcutaneous administration of an anti-IL-12/IL-23p40 antibody.

34 Claims, 1 Drawing Sheet
Specification includes a Sequence Listing.

(56) References Cited

U.S. PATENT DOCUMENTS

| | | |
|---|---|---|
| 2009/0181027 A1 | 7/2009 | Dal Monte et al. |
| 2018/0252728 A1 | 9/2018 | Georgantas, III et al. |
| 2020/0062841 A1 | 2/2020 | Giles-Komar et al. |
| 2020/0262908 A1* | 8/2020 | Jones .................. A61P 1/00 |

FOREIGN PATENT DOCUMENTS

| | | |
|---|---|---|
| EP | 790255 A2 | 8/1997 |
| EP | 433827 B1 | 3/1998 |
| EP | 804581 B1 | 9/2001 |
| EP | 1 137 766 B1 | 9/2005 |
| WO | WO 90/05147 A1 | 5/1990 |
| WO | WO 92/05256 A1 | 4/1992 |
| WO | WO 96/33735 A | 10/1996 |
| WO | WO 97/15327 A | 5/1997 |
| WO | WO 99/37682 A2 | 7/1999 |
| WO | WO 00/34459 A1 | 6/2000 |
| WO | WO 00/56772 A1 | 9/2000 |
| WO | WO 01/19373 A2 | 3/2001 |

OTHER PUBLICATIONS

Adedokun, et al., "Pharmacokinetics and Exposure Response Relationships of Ustekinumab in Patients with Crohn's Disease," Gastroenterology, 154: 1660-1671 (2018).

Ahern et al., "Interleukin-23 Drives Intestinal Inflammation through Direct Activity on T Cell," Immunity. 33(2):279-288 (2010).

Anderson et al., "Meta-analysis identifies 29 additional ulcerative colitis risk loci, increasing the number of confirmed associations to 47," Nature Genetics, 43(3):246-252 (2011).

Baumgart, et al., "Crohn's Disease," Lancet, 380: 1590-1605 (2012).

Berg et al., "Enterocolitis and Colon Cancer in Interleukin-10-deficient Mice are Associated with Aberrant Cytokine Production and CD4+ TH1-like Responses," Journal of Clinical Investigations, 98:1010-1020 (1996).

Steven Brant, "Promises, Delivery, and Challenges of Inflammatory Bowel Disease Risk Gene Discovery," Clinical Gastroenterology and Hepatology, 11(1):22-26 (2013).

Colombel et al., "Adalimumab for Maintenance of Clinical Response and Remission in Patients with Crohn's Disease: The CHARM Trial," Gastroenterology. 132:52-65 (2007).

Danese, et al., "Ulcerative Colitis," New England Journal of Medicine, 365:1715-1725 (2011).

Davidson et al., "IL-12, But Not IFN-γPlays a Major Role in Sustaining the Chronic Phase of Colitis in IL-10-Deficient Mice," Journal of Immunology, 161:3143-3149 (1998).

Feagan et al., "Vedolizumab as Induction and Maintenance Therapy for Ulcerative Colitis," New England Journal of Medicine, 369:699 710 (2013).

Feagan, et al., "Ustekinumab as Induction and Maintenance Therapy for Crohn's Disease," New England Journal of Medicine, 375 (20): 1946-1960 (2016).

Geremia et al., "Innate and adaptive immunity in inflammatory bowel disease," Autoimmunity Reviews, 13:3-10 (2014).

Hanauer et al., "Maintenance infliximab for Crohn's Disease: the ACCENT I randomized trial," Lancet. 359:1541-1549 (2002).

Hanauer, et al., "IM-UNITI: Three-year Efficacy, Safety, and Immunogenicity of Ustekinumab Treatment of Crohn's Disease," Journal of Crohn's and Colitis: 23-32 (2020).

Janssen Research & Development, LLC, "A Study to Evaluate the Safety and Efficacy of Ustekinumab Induction and Maintenance Therapy in participants with Moderately to Severely Active Ulcerative Colitis (UNIFI)," (Dec. 19, 2019).

Janssen Research & Development, LLC, "A Multicenter, Randomized, Double-blind, Placebo-controlled, Proof-of-Concept Study of Ustekinumab in Subjects with Active Systemic Lupus Erythematosus," Clinical Trial No. NCT0239061, Approved Jan. 18, 2017.

Li, et al., "Relationship Between Combined Histologic and Endoscopic Endpoints and Efficacy of Ustekinumab Treatment in Patients with Ulcerative Colitis," Gastroenterology, S0016-5085 (20): 35107-6 (Journal Pre-proof Aug. 2020).

Loftus, et al., "Epidemiology of inflammatory bowel disease," Gastroenterology Clinics of North America, 31:1-20 (2002).

Edward V. Loftus, Jr., "Clinical Epidemiology of Inflammatory Bowel Disease: Incidence, Prevalence, and Environmental Influences," Gastroenterology, 126(6):1504-1517 (2004).

Neurath et al., "Antibodies to Interleukin 12 Abrogate Established Experimental Colitis in Mice," Journal of Experimental Medicine, 182(5):1281-1290 (1995).

Neurath, "Cytokines in inflammatory bowel disease," Nature Revs Immunology, 14(5):329-42 (2014).

Papp, et al., Efficacy and Safety of Ustekinumab, A Human Interleukin-12/23 Monoclonal Antibody, in Patients with Psoriasis: 52 Week Results from a Randomised, Double-Blind, Placebo-Controlled Trial (PHOENIX 2), The Lancet, 371: 1675-1684 (2008).

Sandborn et al., "Adalimumab Induces and Maintains Clinical Remission in Patients With Moderate-to-Severe Ulcerative Colitis," Gastroenterology. 142:257-265 (2012).

Sandborn et al., "A Randomized Trial of Ustekinumab, a Human Interleukin-12/23 Monoclonal Antibody, in Patients with Moderate-to-Severe Crohn's Disease," Gastroenterology. 135(4):1130-1141 (2008).

Sandborn et al., "Vedolizumab as Induction and Maintenance Therapy for Crrohn's Disease," New England Journal of Medicine, 369:711-721 (2013).

Sandborn, et al., "Long-Term Efficacy and Safety of Ustekinumab for Crohn's disease through the second year of therapy," Alimentary Pharmacology & Therapeutics, 48: 65-77 (2018).

Sandborn, et al., "Ustekinumab Induction and Maintenance Therapy in Refractory Crohn's Disease," The New England Journal of Medicine, 367: 1519-1528 (2012).

Sands, et al., "Safety and Efficacy of Ustekinumab Induction Therapy in Patients with Moderate to Severe Ulcerative Colitis: Results from the Phase 3 UNIFI Study," American College of Gastroenterology Conference, Philadelphia, Pennsylvania (Oct. 2018). (Poster Presentation).

Sands, et al, "Ustekinumab as Induction and Maintenance Therapy for Ulcerative Colitis," The New England Journal of Medicine, 381(13): 1201-1214 (2019).

Simon, et al., "Ustekinumab for the treatment of Crohn's disease: can it find its niche?" Therapeutic Advances in Gastroenterology, 9 (1): 26-36 (2016).

Tally et al., "An Evidence-Based Systematic Review of Medical Therapies for Inflammatory Bowel Disease," American Journal of Gastroenterology, 106 Suppl 1:S2-S25 (2011).

Uhlig et al., "Differential Activity of IL-12 and IL-23 in Mucosal and Systemic Innate Immune Pathology," Immunity. 25:309 318 (2006).

Yen et al., "IL-23 is essential for T cell-mediated colitis and promoted inflammation via IL-17 and IL-6," The Journal of Clinical Investigation, 116(5):1310-1316 (2006).

Yu et al., "Expression of Interleukin-22/STAT3 signaling pathway in ulcerative colitis and related carcinogenesis," World Journal of Gastroenterology, 19(17):2638-2649 (2013).

PCT Search Report dated Jan. 13, 2020.

* cited by examiner

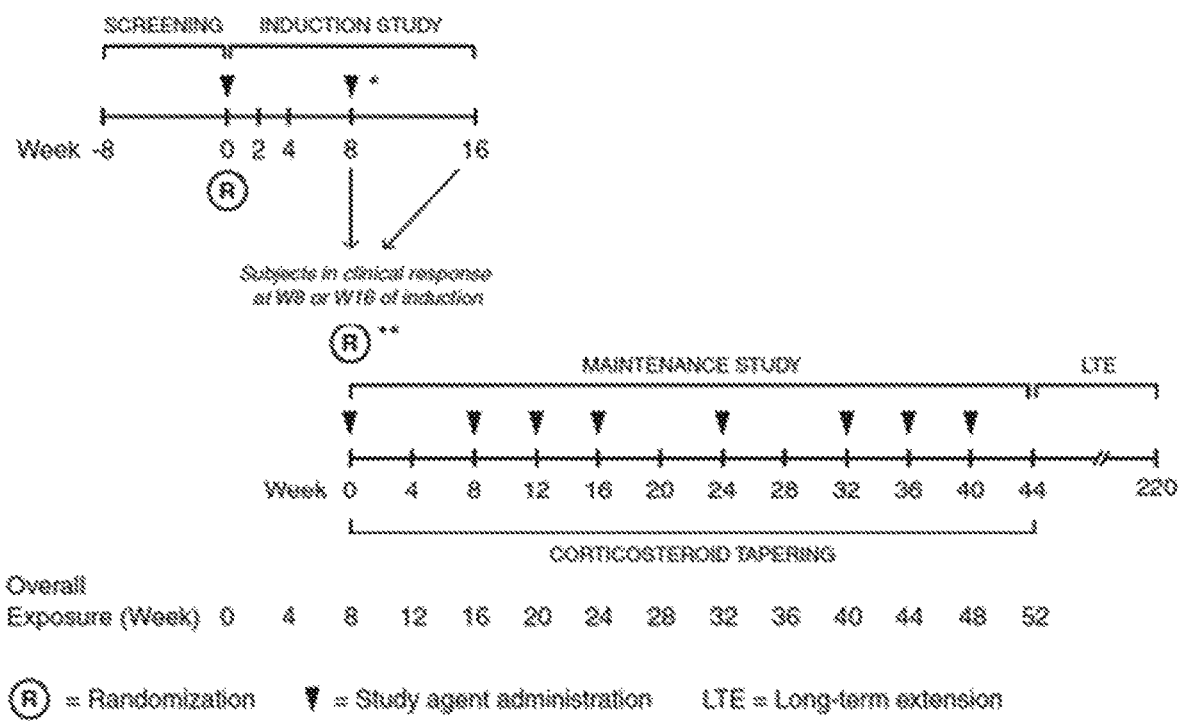

METHODS OF TREATING MODERATELY TO SEVERELY ACTIVE ULCERATIVE COLITIS BY ADMINISTERING AN ANTI-IL12/IL23 ANTIBODY

CROSS-REFERENCE TO RELATED APPLICATIONS

This application claims the benefit of U.S. Provisional Application Ser. No. 62/895,774 filed 4 Sep. 2019, U.S. Provisional Application Ser. No. 62/769,818, filed 20 Nov. 2018 and U.S. Provisional Application Ser. No. 62/735,501, filed 24 Sep., 2018, the entire contents of which are incorporated herein by reference in their entireties.

REFERENCE TO SEQUENCE LISTING SUBMITTED ELECTRONICALLY

This application contains a sequence listing, which is submitted electronically via EFS-Web as an ASCII formatted sequence listing with a file name "JBI6010USNP1Sequence Listing.txt" creation date of 28 Aug. 2018, and having a size of 14,790 bytes. The sequence listing submitted via EFS-Web is part of the specification and is herein incorporated by reference in its entirety.

FIELD OF THE INVENTION

The invention relates to methods of providing a clinically proven safe and clinically proven effective treatment of ulcerative colitis, particularly moderately to severely active ulcerative colitis in patients who have had an inadequate response to or are intolerant of a conventional or existing therapy by intravenous and/or subcutaneous administration of an anti-IL-12/IL-23p40 antibody.

BACKGROUND OF THE INVENTION

Inflammatory bowel diseases (IBDs), including ulcerative colitis (UC), are chronic relapsing disorders characterized by destructive inflammation and epithelial injury in the gastrointestinal (GI) tract (Baumgart and Sandborn, J Clin Invest. 98:1010-1020 (1996); Danese and Fiocchi, N Engl J Med. 365:1715-1725 (2011)). The incidence of UC in the United States is estimated to be between 9 and 12 per 100,000 persons with a prevalence of 205 to 240 per 100,000 persons (Tally et al., Am J Gastroenterol. 106 Suppl 1:S2-S25 (2011)). The estimate of the prevalence of UC in Europe is approximately 1 million people (Loftus, Gastroenterology. 126(6):1504-1517 (2004); Loftus, Gastoenterol Clin N Am. 31:1-20 (2002)). The etiology of UC is unknown. However, abnormal immune responses to contents in the gut, including intestinal microbes, are thought to drive disease in genetically predisposed individuals (Geremia et al., Autoimmun Rev. 13:3-10 (2014)). Dysregulated innate and adaptive immune pathways contribute to aberrant intestinal inflammation in IBD, and cytokines, including interleukin (IL)-12, interferon-gamma (IFNγ), and IL-23 have been implicated in the pathogenesis of UC (Geremia et al., Autoimmune Rev. 2014; 13:3-10; Neurath, Nat Rev Immunol. 14(5):329-42 (2014)).

The involvement of the IL-12/23 pathway in the pathogenesis of IBD is well established, and an important role for IL-12/IL-23 pathway in intestinal inflammation has been elucidated in colitis (Ahern et al., Immunity. 33(2):279-288 (2010); Investigator's Brochure: STELARA® (ustekinumab), edition 18. Janssen Research & Development, LLC (2017); Uhlig et al., Immunity. 25:309 318 (2006); Yen et al., J Clin Invest. 116(5):1310-1316 (2006)). Early studies showed that treatment with anti-IFNγ (Berg et al., J Clin Invest. 98:1010-1020 (1996); Davidson et al., J Immunol. 161:3143-3149 (1998)) or anti-IL-12p40 monoclonal antibodies (mAb) prevented disease in experimental colitis models, suggesting an important role for type 1 T helper (Th-1) cells in promoting intestinal inflammation (Neurath et al., J Exp Med. 182(5):1281-1290 (1995)). Genome-wide association studies have implicated several genetic loci in humans in the IL-12/23 pathway that are associated with increased susceptibility to UC, including IL-23R and IL-12B (Anderson et al., Nat Genet. 43(3):246-252 (2011); Brant et al., Clin Gastroenterol Hepatol. 11(1): 22-26 (2013)). Subjects with active UC were shown to have significantly more IL-23, IL-22, IL-22R1 and p-STAT3-positive cells than subjects with inactive UC and normal controls (Yu et al., World J Gastroenterol. 19(17):2638-2649 (2013)).

Biologic therapies currently approved for the treatment of UC are either tumor necrosis factor (TNF) or integrin inhibitors (Colombel et al., Gastroenterology. 132:52-65 (2007); Hanauer et al., Lancet. 359:1541-1549 (2002); Sandborn et al., N Engl J Med. 369:711-721 (2013); Sandborn et al., Gastroenterology. 142:257-265 (2012)). However, only 1 therapy of all currently approved treatments, vedolizumab, has demonstrated efficacy in subjects who have had an inadequate response to (i.e., primary nonresponse or secondary loss of response) or are intolerant of anti-TNFs (Feagan et al., N Engl J Med. 369:699 710 (2013)). Anti-TNFs have safety risks associated with immunosuppression and not all subjects adequately respond to such therapy. Furthermore, as was observed with the anti-TNFs, inadequate response, and intolerance has been identified in subjects receiving vedolizumab for the treatment of their UC. Therefore, there remains an unmet need for novel therapies with alternative mechanisms of action.

When tested, biologic therapies that are currently approved for the treatment of UC have also demonstrated efficacy in Crohn's disease (Sandborn et al., Gastroenterology. 135(4):1130-1141 (2008)). Multiple lines of evidence suggest that inflammatory bowel disease (UC and Crohn's disease) is mediated by Th1 or Th17 cells with strong contribution from the proinflammatory cytokines, IL-12, and IL-23. Ustekinumab (STELARA®) is a fully human immunoglobulin G1 mAb to human IL-12/23p40 that prevents IL-12 and IL-23 bioactivity by inhibiting their interaction with their cell surface IL-12R131 receptor protein (Investigator's Brochure: STELARA® (ustekinumab), edition 18. Janssen Research & Development, LLC (2017)). Through this mechanism of action, ustekinumab effectively neutralizes IL-12 (Th1)- and IL-23 (Th17)-mediated cellular responses. Ustekinumab has received marketing approval globally, including countries in North America, Europe, South America, and the Asia-Pacific region, for the treatment of adult subjects with moderately to severely active Crohn's disease (the first approval for Crohn's disease was received on 11 Nov. 2016), moderate to severe plaque psoriasis, or active psoriatic arthritis, as well as for pediatric subjects (12 to 17 years old) with moderate to severe plaque psoriasis.

The efficacy and safety of intravenous (IV) ustekinumab as induction therapy in Crohn's disease have been evaluated in clinical studies CRD3001 and CRD3002. In study CRD3001, subjects with demonstrated prior failure or intolerance to one or more TNF antagonists were evaluated, and in CRD3002 subjects with history of inadequate response to or intolerance of corticosteroids or immunomodulators, but without a history of an inadequate response or intolerance to TNF antagonists were evaluated. In these studies, two IV doses were evaluated: a 130 mg IV fixed dose (~2 mg/kg on a mg/kg basis) was chosen for the low-dose group, while body-weight range based doses approximating ~6 mg/kg IV (weight≤55 kg: ustekinumab 260 mg; weight>55 and ≤85 kg: ustekinumab 390 mg; weight>85 kg: ustekinumab: 520 mg) were chosen as the high-dose group. In both studies, ustekinumab demonstrated clinically significant efficacy compared with placebo and was well-tolerated with a favorable safety profile.

Prior to the present invention, no studies had been conducted with ustekinumab for UC. there is a need in the art for improved methods of treating UC, particularly moderately to severely active UC, in subjects who had previously failed or were intolerant of a biologic therapy or other conventional therapy, or subjects who had demonstrated corticosteroid dependence.

BRIEF SUMMARY OF THE INVENTION

The present application relates to clinically proven safe and clinically proven effective methods and compositions for treatment of moderately to severely active ulcerative colitis (UC), particularly in subjects who have had an inadequate response to or are intolerant of a conventional or existing therapy, by administration of an anti-IL-12/IL-23p40 antibody to subjects, thereby addressing a clear unmet medical need in this subject population.

In one general aspect, the application relates to a clinically proven safe and clinically proven effective method of treating moderately to severely active ulcerative colitis (UC) in a subject in need thereof, comprising administering to the subject a pharmaceutical composition comprising a safe and effective amount of an anti-IL-12/IL-23p40 antibody, wherein the antibody comprises a heavy chain variable region and a light chain variable region, the heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and the light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6.

In certain embodiments, the anti-IL-12 and/or anti-IL-23 antibody is administered intravenously to the subject, preferably at week 0, at a dosage of about 6.0 mg/kg body weight of the subject or 130 mg per administration.

In certain embodiments, the anti-IL-12 and/or anti-IL-23 antibody is administered intravenously or subcutaneously to the subject, preferably at week 8, at a dosage of about 6.0 mg/kg body weight of the subject or 90 mg per administration, respectively.

Preferably, the subject treated by methods according to embodiments of the application has had an inadequate response to or are intolerant of a conventional or existing therapy. In some embodiments, the subject had previously failed or were intolerant of a biologic therapy, such as an anti-TNF and/or vedolizumab. In some embodiments, the subject had previously failed or were intolerant of a non-biologic therapy, such as a treatment with corticosteroids, azathioprine (AZA), and/or 6 mercaptopurine (6 MP). In some embodiments, the subject had demonstrated corticosteroid dependence.

In another general aspect, the application relates to a clinically proven safe and clinically proven effective method of treating moderately to severely active ulcerative colitis (UC) in a subject in need thereof, comprising:

intravenously administering to the subject a pharmaceutical composition comprising an anti-IL-12/IL-23p40 antibody at a dosage of about 6.0 mg/kg body weight of the subject or 130 mg of the antibody per administration at week 0 of the treatment, and subcutaneously administering to the subject a pharmaceutical composition comprising the anti-IL-12/IL-23p40 antibody at a dosage of 90 mg of the antibody per administration at week 8 of the treatment, wherein the antibody comprises a heavy chain variable region and a light chain variable region, the heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and the light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6; and wherein the subject had previously failed or were intolerant of at least one therapy selected from the group consisting of: an anti-TNF, vedolizumab, corticosteroids, azathioprine (AZA), and 6 mercaptopurine (6 MP), or the subject had demonstrated corticosteroid dependence In certain embodiments, methods of the present application comprise intravenously (IV) and/or subcutaneously (SC) administering to the subject a pharmaceutical composition comprising an anti-IL-12 and/or anti-IL-23 antibody or antigen binding fragment comprising: (i) a heavy chain variable domain amino acid sequence of SEQ ID NO:7; and (ii) a light chain variable domain amino acid sequence of SEQ ID NO:8.

In certain embodiments, methods of the present application comprise intravenously (IV) and/or subcutaneously (SC) administering to the subject a pharmaceutical composition comprising the anti-IL-12/23p40 antibody ustekinumab, which comprises: (i) a heavy chain amino acid sequence of SEQ ID NO:10; and (ii) a light chain amino acid sequence of SEQ ID NO:11.

In certain embodiments, the IV dose at week 0 is about 6.0 mg/kg. For example, the IV dose is 260 mg for subjects with body weight≥35 kg and ≤55 kg, 390 mg for subjects with body weight>55 kg and ≤85 kg, and 520 mg for subjects with body weight>85 kg.

In certain embodiments, the subject is a responder to a treatment of a method according to an embodiment of the application and is identified as having at least one of: (1) a clinical remission based on at least one of the global submissions and the US submissions; (2) an endoscopic healing; (3) a clinical response; (4) a change from baseline in Inflammatory Bowel Disease Questionnaire (IBDQ) score; (5) a mucosal healing; (6) a decrease from baseline in Mayo score; and (7) a normalization of one or more biomarkers selected from the group consisting of C-reactive protein, fecal lactoferrin and fecal calprotectin. Preferably, at least one of (1) to (7) above is identified from the subject by week 16, more preferably by week 8 or week 4, and most preferably by week 2 of the treatment.

In certain embodiments, the present invention provides a clinically proven safe and clinically proven effective method of treating moderately to severely active UC in a subject, wherein the subject is a responder to the treatment with the antibody and is identified as having a statistically significant improvement in disease activity as determined by endoscopic healing with a Mayo endoscopy subscore of 0 or 1 by week 8 of treatment with the antibody.

In other embodiments, the present invention provides a clinically proven safe and clinically proven effective method of treating moderately to severely active UC in a subject, wherein the subject is a responder to the treatment with the antibody and is identified as having a statistically significant improvement in disease activity as determined by an Ulcerative Colitis Endoscopic Index of Severity (UCEIS) score of ≤4 by week 8 of treatment with the antibody.

In certain embodiments, the subject is in clinical response as determined by a decrease from baseline in the Mayo score by ≥30% and ≥3 points and a decrease from baseline in the rectal bleeding subscore ≥1 points or a rectal bleeding subscore of 0 or 1 by week 8 of treatment with the antibody.

In other embodiments, a maintenance dose of the anti-IL-12/IL-23p40 antibody is administered every 8 weeks after the treatment at week 8 or every 12 weeks after the treatment at week 8 and clinical response is maintained by the subject for at least 44 weeks.

In certain embodiments, the present invention provides a clinically proven safe and clinically proven effective method of treating moderately to severely active UC in a subject, wherein a subject identified as a non-responder to an initial treatment is administered a second treatment, preferably with an administration route different from the initial treatment. For example, a subject identified as a non-responder to an initial treatment with an IV administration of an antibody or antibody binding fragment can be treated with a subsequent subcutaneous administration of the antibody or antibody binding fragment according to embodiments of the invention.

In certain embodiments, the present application provides for a method of treating moderately to severely active UC in a subject, wherein an anti-IL-12 and/or anti-IL-23 antibody for use with IV administration is in a pharmaceutical composition comprising a solution comprising 10 mM L-histidine, 8.5% (w/v) sucrose, 0.04% (w/v) polysorbate 80, 0.4 mg/mL L methionine, and 20 μg/mL EDTA disodium salt, dehydrate, at pH 6.0.

In certain embodiments, the present application provides for a clinically proven safe and clinically proven effective method of treating moderately to severely active UC in a subject, wherein an anti-IL-12 and/or anti-IL-23 antibody for use with subcutaneous administration is in a pharmaceutical composition comprising a solution comprising 6.7 mM L-histidine, 7.6% (w/v) sucrose, 0.004% (w/v) polysorbate 80, at pH 6.0.

In certain embodiments, the present application provides a method further comprising administering to the subject one or more additional drugs used to treat UC. In a preferred embodiment, the additional drug is selected from the group consisting of: oral 5-aminosalicylate (5-ASA) compounds, oral corticosteroids, immunomodulators, 6-mercaptopurine (6-MP), azathioprine (AZA), or methotrexate (MTX).

Other aspects of the application include pharmaceutical compositions comprising an anti-IL-12 and/or anti-IL-23 antibody for use in a clinically proven safe and clinically proven effective method of treating moderately to severely active UC in a subject, as well as methods of preparing the compositions and kits comprising the pharmaceutical compositions.

In certain embodiments, a kit useful for a method of the invention comprises at least one of a pharmaceutical composition for intravenous administration of the invention and pharmaceutical composition for subcutaneous administration of the invention. In other embodiments, the kit comprises both a pharmaceutical composition for intravenous administration and a pharmaceutical composition for subcutaneous administration of the invention.

BRIEF DESCRIPTION OF THE DRAWINGS

The foregoing summary, as well as the following detailed description of the invention, will be better understood when read in conjunction with the appended drawings. It should be understood that the invention is not limited to the precise embodiments shown in the drawings.

FIG. 1 shows a diagrammatic representation of the study design. Abbreviations: W8=Week 8; W16=Week 16; LTE=Long-term Extension.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles or the like which has been included in the present specification is for the purpose of providing context for the invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein.

It must be noted that as used herein and in the appended claims, the singular forms "a," "an," and "the" include plural reference unless the context clearly dictates otherwise. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the invention.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim. Any of the aforementioned terms of "comprising", "containing", "including", and "having", whenever used herein in the context of an aspect or embodiment of the invention can be replaced with the term "consisting of" or "consisting essentially of" to vary scopes of the disclosure.

As used herein, the conjunctive term "and/or" between multiple recited elements is understood as encompassing both individual and combined options. For instance, where two elements are conjoined by "and/or", a first option refers to the applicability of the first element without the second. A second option refers to the applicability of the second element without the first. A third option refers to the applicability of the first and second elements together. Any one of these options is understood to fall within the meaning, and therefore satisfy the requirement of the term "and/or" as used herein. Concurrent applicability of more than one of the options is also understood to fall within the meaning, and therefore satisfy the requirement of the term "and/or."

As used herein, "subject" means any animal, preferably a mammal, most preferably a human, whom will be or has been treated by a method according to an embodiment of the invention. The term "mammal" as used herein, encompasses any mammal. Examples of mammals include, but are not limited to, cows, horses, sheep, pigs, cats, dogs, mice, rats, rabbits, guinea pigs, non-human primates (NHPs) such as monkeys or apes, humans, etc., more preferably a human.

As used herein, the term "in combination", in the context of the administration of two or more therapies to a subject, refers to the use of more than one therapy. The term "in combination" does not restrict the order in which therapies are administered to a subject. For example, a first therapy (e.g., a composition described herein) can be administered prior to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 16 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy to a subject.

As used herein, an "anti-IL-12 antibody," "anti-IL-23 antibody," "anti-IL-12/23p40 antibody," or "IL-12/23p40 antibody," refers to a monoclonal antibody (mAb) or antigen binding fragment thereof, that binds the 40 kDa (p40) subunit shared by the cytokines interleukin-12 and interleukin-23 (IL-12/23p40). The antibody can affect at least one of IL-12/23 activity or function, such as but not limited to, RNA, DNA or protein synthesis, IL-12/23 release, IL-12/23 receptor signaling, membrane IL-12/23 cleavage, IL-12/23 activity, IL-12/23 production and/or synthesis.

The term "antibody" is further intended to encompass antibodies, digestion fragments, specified portions and variants thereof, including antibody mimetics or comprising portions of antibodies that mimic the structure and/or function of an antibody or specified fragment or portion thereof, including single chain antibodies and fragments thereof. Functional fragments include antigen-binding fragments that bind to a mammalian IL-12/23. For example, antibody fragments capable of binding to IL-12/23 or portions thereof, including, but not limited to, Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), Fv or scFv (e.g., by molecular biology techniques) fragments, are encompassed by the invention (see, e.g., Colligan, Immunology, supra).

Such fragments can be produced by enzymatic cleavage, synthetic or recombinant techniques, as known in the art and/or as described herein. Antibodies can also be produced in a variety of truncated forms using antibody genes in which one or more stop codons have been introduced upstream of the natural stop site. For example, a combination gene encoding a F(ab')$_2$ heavy chain portion can be designed to include DNA sequences encoding the $C_H1$ domain and/or hinge region of the heavy chain. The various portions of antibodies can be joined together chemically by conventional techniques, or can be prepared as a contiguous protein using genetic engineering techniques.

As used herein, the term "human antibody" refers to an antibody in which substantially every part of the protein (e.g., CDR, framework, $C_L$, $C_H$ domains (e.g., $C_H1$, $C_H2$, $C_H3$), hinge, ($V_L$, $V_H$)) is substantially non-immunogenic in humans, with only minor sequence changes or variations. A "human antibody" can also be an antibody that is derived from or closely matches human germline immunoglobulin sequences. Human antibodies can include amino acid residues not encoded by germline immunoglobulin sequences (e.g., mutations introduced by random or site-specific mutagenesis in vitro or by somatic mutation in vivo). Often, this means that the human antibody is substantially non-immunogenic in humans. Human antibodies have been classified into groupings based on their amino acid sequence similarities. Accordingly, using a sequence similarity search, an antibody with a similar linear sequence can be chosen as a template to create a human antibody. Similarly, antibodies designated primate (monkey, baboon, chimpanzee, etc.), rodent (mouse, rat, rabbit, guinea pig, hamster, and the like) and other mammals designate such species, sub-genus, genus, sub-family, and family specific antibodies. Further, chimeric antibodies can include any combination of the above. Such changes or variations optionally and preferably retain or reduce the immunogenicity in humans or other species relative to non-modified antibodies. Thus, a human antibody is distinct from a chimeric or humanized antibody.

It is pointed out that a human antibody can be produced by a non-human animal or prokaryotic or eukaryotic cell that is capable of expressing functionally rearranged human immunoglobulin (e.g., heavy chain and/or light chain) genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

Anti-IL-12/23p40 antibodies (also termed IL-12/23p40 antibodies) (or antibodies to IL-23) useful in the methods and compositions of the present invention can optionally be characterized by high affinity binding to IL-12/23p40, optionally and preferably, having low toxicity. In particular, an antibody, specified fragment or variant of the invention, where the individual components, such as the variable region, constant region and framework, individually and/or collectively, optionally and preferably possess low immunogenicity, is useful in the present invention. The antibodies that can be used in the invention are optionally characterized by their ability to treat subjects for extended periods with measurable alleviation of symptoms and low and/or acceptable toxicity. Low or acceptable immunogenicity and/or high affinity, as well as other suitable properties, can contribute to the therapeutic results achieved. "Low immunogenicity" is defined herein as raising significant HAHA, HACA or HAMA responses in less than about 75%, or preferably less than about 50% of the subjects treated and/or raising low titres in the subject treated (less than about 300, preferably less than about 100 measured with a double antigen enzyme immunoassay) (Elliott et al., Lancet 344: 1125-1127 (1994), entirely incorporated herein by reference). "Low immunogenicity" can also be defined as the incidence of titrable levels of antibodies to the anti-IL-12 antibody in subjects treated with anti-IL-12 antibody as occurring in less than 25% of subjects treated, preferably, in less than 10% of subjects treated with the recommended dose for the recommended course of therapy during the treatment period.

The terms "clinically proven efficacy" and "clinically proven effective" as used herein in the context of a dose, dosage regimen, treatment or method refer to the effectiveness of a particular dose, dosage or treatment regimen. Efficacy can be measured based on change in the course of the disease in response to an agent of the present invention. For example, an anti-IL12/23p40 of the present invention (e.g., ustekinumab) is administered to a subject in an amount and for a time sufficient to induce an improvement, preferably a sustained improvement, in at least one indicator that reflects the severity of the disorder that is being treated. Various indicators that reflect the extent of the subject's illness, disease or condition can be assessed for determining whether the amount and time of the treatment is sufficient. Such indicators include, for example, clinically recognized indicators of disease severity, symptoms, or manifestations of the disorder in question. The degree of improvement generally is determined by a physician, who can make this determination based on signs, symptoms, biopsies, or other test results, and who can also employ questionnaires that are administered to the subject, such as quality-of-life questionnaires developed for a given disease. For example, an anti-IL12/23p40 or anti-IL23 antibody of the present invention can be administered to achieve an improvement in a subject's condition related to ulcerative colitis.

Improvement can be indicated by an improvement in an index of disease activity, by amelioration of clinical symptoms or by any other measure of disease activity. Once such index of disease is the ulcerative colitis Mayo score. The Mayo score is an established, validated disease activity index for mild, moderate, and severe ulcerative colitis (UC) that is calculated as the sum of the 4 subscores of stool frequency, rectal bleeding, findings of endoscopy, and physician's global assessment (PGA), and ranges from 0-12. A score of 3 to 5 points indicates mildly active disease, a score of 6 to 10 points indicates moderately active disease, and a score of 11 to 12 points indicates severe disease. The partial Mayo score, which is the Mayo score without the endoscopy subscore, is calculated as the sum of stool frequency, rectal bleeding, and physician's global assessment subscores, and ranges from 0 to 9. The modified Mayo score, which is the Mayo score without the PGA subscore, is calculated as the sum of the stool frequency, rectal bleeding, and endoscopy subscores, and ranges from 0 to 9. Other disease activity indexes for UC include for example, Ulcerative Colitis Endoscopic Index of Severity (UCEIS) score and the Bristol Stool Form Scale (BSFS) score. The UCEIS score provides an overall assessment of endoscopic severity of UC, based on mucosal vascular pattern, bleeding, and ulceration (Travis et al., Gut. 61:535-542 (2012)). The score ranges from 3 to 11 with a higher score indicating more severe disease by endoscopy. The BSFS score is used to classify the form (or consistency) of human feces into 7 categories (Lewis and Heaton, Scand J Gastroenterol. 32(9):920-924 (1997)).

The term "clinical response" as used herein as it relates to a subject's response to drug administration, refers to a decrease from induction baseline in the Mayo score by ≥30% and ≥3 points, with either a decrease from baseline in the rectal bleeding subscore ≥1 or a rectal bleeding subscore of 0 or 1.

The term "clinically proven safe," as it relates to a dose, dosage regimen, treatment or method with anti-IL-12/IL-23p40 antibody of the present invention (e.g., ustekinumab), refers to a favorable risk:benefit ratio with an acceptable frequency and/or acceptable severity of treatment-emergent adverse events (referred to as AEs or TEAEs) compared to the standard of care or to another comparator. As used herein, "adverse event," "treatment-emergent adverse event," and "adverse reaction" mean any harm, unfavorable, unintended or undesired sign or outcome associated with or caused by administration of a pharmaceutical composition or therapeutic. It is an untoward medical occurrence in a subject administered a medicinal product. However, abnormal values or observations are not reported as adverse events unless considered clinically significant by the investigator. As used herein, when referring to an adverse event, "clinically apparent" means clinically significant as determined by a medical doctor or an investigator using standard acceptable to those of ordinary skill in the art. When the harm or undesired outcome of adverse events reaches such a level of severity, a regulatory agency can deem the pharmaceutical composition or therapeutic unacceptable for the proposed use. In particular, "safe" as it relates to a dose, dosage regimen or treatment with an anti-IL12/23p40 or anti-IL23 antibody of the present invention refers to with an acceptable frequency and/or acceptable severity of adverse events associated with administration of the antibody if attribution is considered to be possible, probable, or very likely due to the use of the anti-IL12/23p40 or anti-IL23 antibody.

As used herein, unless otherwise noted, the term "clinically proven" (used independently or to modify the terms "safe" and/or "effective") shall mean that it has been proven by a clinical trial wherein the clinical trial has met the approval standards of U.S. Food and Drug Administration, EMEA or a corresponding national regulatory agency. For example, the clinical study may be an adequately sized, randomized, double-blinded study used to clinically prove the effects of the drug.

As used herein, a dosage amount of an anti-IL-12/IL-23p40 antibody in "mg/kg" refers to the amount of the anti-IL-12/IL-23p40 antibody in milligrams per kilogram of the body weight of a subject to be administered with the antibody.

Antibodies of the Present Invention—Production and Generation

At least one anti-IL-12/23p40 (or anti-IL-23) used in the method of the present invention can be optionally produced by a cell line, a mixed cell line, an immortalized cell or clonal population of immortalized cells, as well known in the art. See, e.g., Ausubel, et al., ed., Current Protocols in Molecular Biology, John Wiley & Sons, Inc., NY, NY (1987-2001); Sambrook, et al., Molecular Cloning: A Laboratory Manual, 2nd Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001), each entirely incorporated herein by reference.

Human antibodies that are specific for human IL-12/23p40 or IL-23 proteins or fragments thereof can be raised against an appropriate immunogenic antigen, such as an isolated IL-12/23p40 protein, IL-23 protein and/or a portion thereof (including synthetic molecules, such as synthetic peptides). Other specific or general mammalian antibodies can be similarly raised. Preparation of immunogenic antigens, and monoclonal antibody production can be performed using any suitable technique in view of the present disclosure.

In one approach, a hybridoma is produced by fusing a suitable immortal cell line (e.g., a myeloma cell line, such as, but not limited to, Sp2/0, Sp2/0-AG14, NSO, NS1, NS2, AE-1, L.5, L243, P3X63Ag8.653, Sp2 SA3, Sp2 MAI, Sp2 SS1, Sp2 SA5, U937, MLA 144, ACT IV, MOLT4, DA-1, JURKAT, WEHI, K-562, COS, RAJI, NIH 3T3, HL-60, MLA 144, NAMALWA, NEURO 2A, or the like, or heteromylomas, fusion products thereof, or any cell or fusion cell derived therefrom, or any other suitable cell line as known in the art) (see, e.g., www.atcc.org, www.lifetech.com, and the like), with antibody producing cells, such as, but not limited to, isolated or cloned spleen, peripheral blood, lymph, tonsil, or other immune or B cell containing cells, or any other cells expressing heavy or light chain constant or variable or framework or CDR sequences, either as endogenous or heterologous nucleic acid, as recombinant or endogenous, viral, bacterial, algal, prokaryotic, amphibian, insect, reptilian, fish, mammalian, rodent, equine, ovine, goat, sheep, primate, eukaryotic, genomic DNA, cDNA, rDNA, mitochondrial DNA or RNA, chloroplast DNA or RNA, hnRNA, mRNA, tRNA, single, double or triple stranded, hybridized, and the like or any combination thereof. See, e.g., Ausubel, supra, and Colligan, Immunology, supra, chapter 2, entirely incorporated herein by reference.

Antibody producing cells can also be obtained from the peripheral blood or, preferably, the spleen or lymph nodes, of humans or other suitable animals that have been immunized with the antigen of interest. Any other suitable host cell can also be used for expressing heterologous or endogenous nucleic acid encoding an antibody, specified fragment or variant thereof, of the present invention. The fused cells (hybridomas) or recombinant cells can be isolated using selective culture conditions or other suitable known methods, and cloned by limiting dilution or cell sorting, or other known methods. Cells which produce antibodies with the desired specificity can be selected by a suitable assay (e.g., ELISA).

Other suitable methods of producing or isolating antibodies of the requisite specificity can be used, including, but not limited to, methods that select recombinant antibody from a peptide or protein library (e.g., but not limited to, a bacteriophage, ribosome, oligonucleotide, RNA, cDNA, or the like, display library; e.g., as available from Cambridge antibody Technologies, Cambridgeshire, UK; MorphoSys, Martinsreid/Planegg, DE; Biovation, Aberdeen, Scotland, UK; Biolnvent, Lund, Sweden; Dyax Corp., Enzon, Affymax/Biosite; Xoma, Berkeley, Calif.; Ixsys. See, e.g., EP 368,684, PCT/GB91/01134; PCT/GB92/01755; PCT/GB92/002240; PCT/GB92/00883; PCT/GB93/00605; U.S. Ser. No. 08/350,260(5/12/94); PCT/GB94/01422; PCT/GB94/02662; PCT/GB97/01835; (CAT/MRC); WO90/14443; WO90/14424; WO90/14430; PCT/US94/1234; WO92/18619; WO96/07754; (Scripps); WO96/13583, WO97/08320 (MorphoSys); WO95/16027 (Biolnvent); WO88/06630; WO90/3809 (Dyax); U.S. Pat. No. 4,704,692 (Enzon); PCT/US91/02989 (Affymax); WO89/06283; EP 371 998; EP 550 400; (Xoma); EP 229 046; PCT/US91/07149 (Ixsys); or stochastically generated peptides or proteins—U.S. Pat. Nos. 5,723,323, 5,763,192, 5,814,476, 5,817,483, 5,824,514, 5,976,862, WO 86/05803, EP 590 689 (Ixsys, predecessor of Applied Molecular Evolution (AME), each entirely incorporated herein by reference)) or that rely upon immunization of transgenic animals (e.g., SCID mice, Nguyen et al., Microbiol. Immunol. 41:901-907 (1997); Sandhu et al., Crit. Rev. Biotechnol. 16:95-118 (1996); Eren et al., Immunol. 93:154-161 (1998), each entirely incorporated by reference as well as related patents and applications) that are capable of producing a repertoire of human antibodies, as known in the art and/or as described herein. Such techniques, include, but are not limited to, ribosome display (Hanes et al., Proc. Natl. Acad. Sci. USA, 94:4937-4942 (Can 1997); Hanes et al., Proc. Natl. Acad. Sci. USA, 95:14130-14135 (November 1998)); single cell antibody producing technologies (e.g., selected lymphocyte antibody method ("SLAM") (U.S. Pat. No. 5,627,052, Wen et al., J. Immunol. 17:887-892 (1987); Babcook et al., Proc. Natl. Acad. Sci. USA 93:7843-7848 (1996)); gel microdroplet and flow cytometry (Powell et al., Biotechnol. 8:333-337 (1990); One Cell Systems, Cambridge, Mass.; Gray et al., J. Imm. Meth. 182:155-163 (1995); Kenny et al., Bio/Technol. 13:787-790 (1995)); B-cell selection (Steenbakkers et al., Molec. Biol. Reports 19:125-134 (1994); Jonak et al., Progress Biotech, Vol. 5, In Vitro Immunization in Hybridoma Technology, Borrebaeck, ed., Elsevier Science Publishers B.V., Amsterdam, Netherlands (1988)).

Methods for engineering or humanizing non-human or human antibodies can also be used and are well known in the art. Generally, a humanized or engineered antibody has one or more amino acid residues from a source that is non-human, e.g., but not limited to, mouse, rat, rabbit, non-human primate or other mammal. These non-human amino acid residues are replaced by residues often referred to as "import" residues, which are typically taken from an "import" variable, constant or other domain of a known human sequence.

Known human Ig sequences are disclosed, e.g., www.ncbi.nlm.nih.gov/entrez/query.fcgi; www.ncbi.nih.gov/igblast; www.atcc.org/phage/hdb.html; www.mrc-cpe.cam.ac.uk/ALIGNMENTS.php; www.kabatdatabase.com/top.html; ftp.ncbi.nih.gov/repository/kabat; www.sciquest.com; www.abcam.com; www.antibodyresource.com/onlinecomp.html; www.public.iastate.edu/~pedro/research_tools.html; www.whfreeman.com/immunology/CH05/kuby05.htm; www.hhmi.org/grants/lectures/1996/vlab; www.path.cam.ac.uk/~mrc7/mikeimages.html; mcb.harvard.edu/BioLinks/Immunology.html; www.immunologylink.com; pathbox.wustl.edu/~hcenter/index.html; www.appliedbiosystems.com; www.nal.usda.gov/awic/pubs/antibody; www.m.ehime-u.ac.jp/~yasuhito/Elisa.html; www.biodesign.com; www.cancerresearchuk.org; www.biotech.ufl.edu; www.isac-net.org; baserv.uci.kun.nl/~jraats/links1.html; www.recab.uni-hd.de/immuno.bme.nwu.edu; www.mrc-cpe.cam.ac.uk; www.ibt.unam.mx/vir/V_mice.html; http://www.bioinforg.uk/abs; antibody.bath.ac.uk; www.unizh.ch; www.cryst.bbk.ac.uk/~ubcg07s; www.nimr.mrc.ac.uk/CC/ccaewg/ccaewg.html; www.path.cam.ac.uk/~mrc7/humanisation/TAHHP.html; www.ibt.unam.mx/vir/structure/stat_aim.html; www.biosci.missouri.edu/smithgp/index.html; www.jerini.de; Kabat et al., Sequences of Proteins of Immunological Interest, U.S. Dept. Health (1983), each entirely incorporated herein by reference.

Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing antigen binding. Accordingly, part or all of the non-human or human CDR sequences are maintained while the non-human sequences of the variable and constant regions can be replaced with human or other amino acids.

Antibodies can also optionally be humanized or human antibodies engineered with retention of high affinity for the antigen and other favorable biological properties. To achieve this goal, humanized (or human) antibodies can be optionally prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, framework (FR) residues can be selected and combined from the consensus and import sequences so that the desired antibody characteristic, such as increased affinity for the target antigen(s), is achieved.

In addition, the human anti-IL-12/23p40 (or anti-IL-23) specific antibody used in the method of the present invention can comprise a human germline light chain framework. In particular embodiments, the light chain germline sequence is selected from human VK sequences including, but not limited to, A1, A10, A11, A14, A17, A18, A19, A2, A20, A23, A26, A27, A3, A30, A5, A7, B2, B3, L1, L10, L11, L12, L14, L15, L16, L18, L19, L2, L20, L22, L23, L24, L25, L4/18a, L5, L6, L8, L9, O1, O11, O12, O14, O18, O2, O4, and O8. In certain embodiments, this light chain human germline framework is selected from V1-11, V1-13, V1-16, V1-17, V1-18, V1-19, V1-2, V1-20, V1-22, V1-3, V1-4, V1-5, V1-7, V1-9, V2-1, V2-11, V2-13, V2-14, V2-15, V2-17, V2-19, V2-6, V2-7, V2-8, V3-2, V3-3, V3-4, V4-1, V4-2, V4-3, V4-4, V4-6, V5-1, V5-2, V5-4, and V5-6.

In other embodiments, the human anti-IL-12/23p40 (or anti-IL-23) specific antibody used in the method of the present invention can comprise a human germline heavy chain framework. In particular embodiments, this heavy chain human germline framework is selected from VH1-18, VH1-2, VH1-24, VH1-3, VH1-45, VH1-46, VH1-58, VH1-69, VH1-8, VH2-26, VH2-5, VH2-70, VH3-11, VH3-13, VH3-15, VH3-16, VH3-20, VH3-21, VH3-23, VH3-30, VH3-33, VH3-35, VH3-38, VH3-43, VH3-48, VH3-49, VH3-53, VH3-64, VH3-66, VH3-7, VH3-72, VH3-73, VH3-74, VH3-9, VH4-28, VH4-31, VH4-34, VH4-39, VH4-4, VH4-59, VH4-61, VH5-51, VH6-1, and VH7-81.

In particular embodiments, the light chain variable region and/or heavy chain variable region comprises a framework region or at least a portion of a framework region (e.g., containing 2 or 3 subregions, such as FR2 and FR3). In certain embodiments, at least FRL1, FRL2, FRL3, or FRL4 is fully human. In other embodiments, at least FRH1, FRH2, FRH3, or FRH4 is fully human. In some embodiments, at least FRL1, FRL2, FRL3, or FRL4 is a germline sequence (e.g., human germline) or comprises human consensus sequences for the particular framework (readily available at the sources of known human Ig sequences described above). In other embodiments, at least FRH1, FRH2, FRH3, or FRH4 is a germline sequence (e.g., human germline) or comprises human consensus sequences for the particular framework. In preferred embodiments, the framework region is a fully human framework region.

Humanization or engineering of antibodies of the present invention can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151: 2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,723,323, 5,976,862, 5,824,514, 5,817,483, 5,814,476, 5,763,192, 5,723,323, 5,766886, 5714352, 6204023, 6180370, 5693762, 5530101, 5585089, 5225539; 4816567, PCT/: US98/16280, US96/18978, US91/09630, US91/05939, US94/01234, GB89/01334, GB91/01134, GB92/01755; WO90/14443, WO90/14424, WO90/14430, EP 229246, each entirely incorporated herein by reference, included references cited therein.

In certain embodiments, the antibody comprises an altered (e.g., mutated) Fc region. For example, in some embodiments, the Fc region has been altered to reduce or enhance the effector functions of the antibody. In some embodiments, the Fc region is an isotype selected from IgM, IgA, IgG, IgE, or other isotype. Alternatively, or additionally, it can be useful to combine amino acid modifications with one or more further amino acid modifications that alter C1q binding and/or the complement dependent cytotoxicity function of the Fc region of an IL-23 binding molecule. The starting polypeptide of particular interest can be one that binds to C1q and displays complement dependent cytotoxicity (CDC). Polypeptides with pre-existing C1q binding activity, optionally further having the ability to mediate CDC can be modified such that one or both of these activities are enhanced. Amino acid modifications that alter C1q and/or modify its complement dependent cytotoxicity function are described, for example, in WO0042072, which is hereby incorporated by reference.

As disclosed above, one can design an Fc region of the human anti-IL-12/23p40 (or anti-IL-23) specific antibody of the present invention with altered effector function, e.g., by modifying C1q binding and/or FcγR binding and thereby changing complement dependent cytotoxicity (CDC) activity and/or antibody-dependent cell-mediated cytotoxicity (ADCC) activity. "Effector functions" are responsible for activating or diminishing a biological activity (e.g., in a subject). Examples of effector functions include, but are not limited to: C1q binding; CDC; Fc receptor binding; ADCC; phagocytosis; down regulation of cell surface receptors (e.g., B cell receptor; BCR), etc. Such effector functions can require the Fc region to be combined with a binding domain (e.g., an antibody variable domain) and can be assessed using various assays (e.g., Fc binding assays, ADCC assays, CDC assays, etc.).

For example, one can generate a variant Fc region of the human anti-IL-12/23p40 (or anti-IL-23) antibody with improved C1q binding and improved FcγRIII binding (e.g., having both improved ADCC activity and improved CDC activity). Alternatively, if it is desired that effector function be reduced or ablated, a variant Fc region can be engineered with reduced CDC activity and/or reduced ADCC activity. In other embodiments, only one of these activities can be increased, and, optionally, also the other activity reduced (e.g., to generate an Fc region variant with improved ADCC activity, but reduced CDC activity and vice versa).

Fc mutations can also be introduced in engineer to alter their interaction with the neonatal Fc receptor (FcRn) and improve their pharmacokinetic properties. A collection of human Fc variants with improved binding to the FcRn have been described (Shields et al., (2001). High resolution mapping of the binding site on human IgG1 for FcγRI, FcγRII, FcγRIII, and FcRn and design of IgG1 variants with improved binding to the FcγR, J. Biol. Chem. 276:6591-6604).

Another type of amino acid substitution serves to alter the glycosylation pattern of the Fc region of the human anti-IL-12/23p40 (or anti-IL-23) specific antibody. Glycosylation of an Fc region is typically either N-linked or O-linked. N-linked refers to the attachment of the carbohydrate moiety to the side chain of an asparagine residue. O-linked glycosylation refers to the attachment of one of the sugars N-aceylgalactosamine, galactose, or xylose to a hydroxyamino acid, most commonly serine or threonine, although 5-hydroxyproline or 5-hydroxylysine can also be used. The recognition sequences for enzymatic attachment of the carbohydrate moiety to the asparagine side chain peptide sequences are asparagine-X-serine and asparagine-X-threonine, where X is any amino acid except proline. Thus, the presence of either of these peptide sequences in a polypeptide creates a potential glycosylation site.

The glycosylation pattern can be altered, for example, by deleting one or more glycosylation site(s) found in the polypeptide, and/or adding one or more glycosylation sites that are not present in the polypeptide. Addition of glycosylation sites to the Fc region of a human IL-23 specific antibody is conveniently accomplished by altering the amino acid sequence such that it contains one or more of the above-described tripeptide sequences (for N-linked glycosylation sites). An exemplary glycosylation variant has an amino acid substitution of residue Asn 297 of the heavy chain. The alteration can also be made by the addition of, or substitution by, one or more serine or threonine residues to the sequence of the original polypeptide (for O-linked glycosylation sites). Additionally, a change of Asn 297 to Ala can remove one of the glycosylation sites.

In certain embodiments, the human anti-IL-12/23p40 (or anti-IL-23) specific antibody of the present invention is expressed in cells that express beta (1,4)-N-acetylglucosaminyltransferase III (GnT III), such that GnT III adds GlcNAc to the human anti-IL-12/23p40 (or anti-IL-23) antibody. Methods for producing antibodies in such a fashion are provided in WO/9954342, WO/03011878, patent publication 20030003097A1, and Umana et al., Nature Biotechnology, 17:176-180, February 1999; all of which are herein specifically incorporated by reference in their entireties.

The human anti-IL-12/23p40 (or anti-IL-23) antibody can also be optionally generated by immunization of a transgenic animal (e.g., mouse, rat, hamster, non-human primate, and the like) capable of producing a repertoire of human antibodies, as described herein and/or as known in the art. Cells that produce a human anti-IL-12/23p40 (or anti-IL-23) antibody can be isolated from such animals and immortalized using suitable methods, such as the methods described herein.

Transgenic mice that can produce a repertoire of human antibodies that bind to human antigens can be produced by known methods (e.g., but not limited to, U.S. Pat. Nos. 5,770,428, 5,569,825, 5,545,806, 5,625,126, 5,625,825, 5,633,425, 5,661,016 and 5,789,650 issued to Lonberg et al.; Jakobovits et al. WO 98/50433, Jakobovits et al. WO 98/24893, Lonberg et al. WO 98/24884, Lonberg et al. WO 97/13852, Lonberg et al. WO 94/25585, Kucherlapate et al. WO 96/34096, Kucherlapate et al. EP 0463 151 B1, Kucherlapate et al. EP 0710 719 A1, Surani et al. U.S. Pat. No. 5,545,807, Bruggemann et al. WO 90/04036, Bruggemann et al. EP 0438 474 B1, Lonberg et al. EP 0814 259 A2, Lonberg et al. GB 2 272 440 A, Lonberg et al. Nature 368:856-859 (1994), Taylor et al., Int. Immunol. 6(4)579-591 (1994), Green et al, Nature Genetics 7:13-21 (1994), Mendez et al., Nature Genetics 15:146-156 (1997), Taylor et al., Nucleic Acids Research 20(23):6287-6295 (1992), Tuaillon et al., Proc Natl Acad Sci USA 90(8)3720-3724 (1993), Lonberg et al., Int Rev Immunol 13(1):65-93 (1995) and Fishwald et al., Nat Biotechnol 14(7):845-851 (1996), which are each entirely incorporated herein by reference). Generally, these mice comprise at least one transgene comprising DNA from at least one human immunoglobulin locus that is functionally rearranged, or which can undergo functional rearrangement. The endogenous immunoglobulin loci in such mice can be disrupted or deleted to eliminate the capacity of the animal to produce antibodies encoded by endogenous genes.

Screening antibodies for specific binding to similar proteins or fragments can be conveniently achieved using peptide display libraries. This method involves the screening of large collections of peptides for individual members having the desired function or structure. Antibody screening of peptide display libraries is well known in the art. The displayed peptide sequences can be from 3 to 5000 or more amino acids in length, frequently from 5-100 amino acids long, and often from about 8 to 25 amino acids long. In addition to direct chemical synthetic methods for generating peptide libraries, several recombinant DNA methods have been described. One type involves the display of a peptide sequence on the surface of a bacteriophage or cell. Each bacteriophage or cell contains the nucleotide sequence encoding the particular displayed peptide sequence. Such methods are described in PCT Patent Publication Nos. 91/17271, 91/18980, 91/19818, and 93/08278.

Other systems for generating libraries of peptides have aspects of both in vitro chemical synthesis and recombinant methods. See, PCT Patent Publication Nos. 92/05258, 92/14843, and 96/19256. See also, U.S. Pat. Nos. 5,658,754; and 5,643,768. Peptide display libraries, vector, and screening kits are commercially available from such suppliers as Invitrogen (Carlsbad, Calif.), and Cambridge antibody Technologies (Cambridgeshire, UK). See, e.g., U.S. Pat. Nos. 4,704,692, 4,939,666, 4,946,778, 5,260,203, 5,455,030, 5,518,889, 5,534,621, 5,656,730, 5,763,733, 5,767,260, 5,856,456, assigned to Enzon; U.S. Pat. Nos. 5,223,409, 5,403,484, 5,571,698, 5,837,500, assigned to Dyax, 5427908, 5580717, assigned to Affymax; 5885793, assigned to Cambridge antibody Technologies; 5750373, assigned to Genentech, 5618920, 5595898, 5576195, 5698435, 5693493, 5698417, assigned to Xoma, Colligan, supra; Ausubel, supra; or Sambrook, supra, each of the above patents and publications entirely incorporated herein by reference.

Antibodies used in the method of the present invention can also be prepared using at least one anti-IL-12/23p40 (or anti-IL-23) antibody encoding nucleic acid to provide transgenic animals or mammals, such as goats, cows, horses, sheep, rabbits, and the like, that produce such antibodies in their milk. Such animals can be provided using known methods. See, e.g., but not limited to, U.S. Pat. Nos. 5,827, 690; 5,849,992; 4,873,316; 5,849,992; 5,994,616; 5,565, 362; 5,304,489, and the like, each of which is entirely incorporated herein by reference.

Antibodies used in the method of the present invention can additionally be prepared using at least one anti-IL-12/23p40 (or anti-IL-23) antibody encoding nucleic acid to provide transgenic plants and cultured plant cells (e.g., but not limited to, tobacco and maize) that produce such antibodies, specified portions or variants in the plant parts or in cells cultured therefrom. As a non-limiting example, transgenic tobacco leaves expressing recombinant proteins have been successfully used to provide large amounts of recombinant proteins, e.g., using an inducible promoter. See, e.g., Cramer et al., Curr. Top. Microbol. Immunol. 240:95-118 (1999) and references cited therein. Also, transgenic maize have been used to express mammalian proteins at commercial production levels, with biological activities equivalent to those produced in other recombinant systems or purified from natural sources. See, e.g., Hood et al., Adv. Exp. Med. Biol. 464:127-147 (1999) and references cited therein. Antibodies have also been produced in large amounts from transgenic plant seeds including antibody fragments, such as single chain antibodies (scFv's), including tobacco seeds and potato tubers. See, e.g., Conrad et al., Plant Mol. Biol. 38:101-109 (1998) and references cited therein. Thus, antibodies of the present invention can also be produced using transgenic plants, according to known methods. See also, e.g., Fischer et al., Biotechnol. Appl. Biochem. 30:99-108 (October, 1999), Ma et al., Trends Biotechnol. 13:522-7 (1995); Ma et al., Plant Physiol. 109:341-6 (1995); Whitelam et al., Biochem. Soc. Trans. 22:940-944 (1994); and references cited therein. Each of the above references is entirely incorporated herein by reference.

The antibodies used in the method of the invention can bind human IL-12/IL-23p40 or IL-23 with a wide range of affinities (KD). In a preferred embodiment, a human mAb can optionally bind human IL-12/IL-23p40 or IL-23 with high affinity. For example, a human mAb can bind human IL-12/IL-23p40 or IL-23 with a KD equal to or less than about 10-7 M, such as but not limited to, 0.1-9.9 (or any range or value therein)×10-7, 10-8, 10-9, 10-10, 10-11, 10-12, 10-13 or any range or value therein.

The affinity or avidity of an antibody for an antigen can be determined experimentally using any suitable method. (See, for example, Berzofsky, et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein). The measured affinity of a particular antibody-antigen interaction can vary if measured under different conditions (e.g., salt concentration, pH). Thus, measurements of affinity and other antigen-binding parameters (e.g., KD, Ka, Kd) are preferably made with standardized solutions of antibody and antigen, and a standardized buffer, such as the buffer described herein.

Vectors and Host Cells

The present invention also relates to vectors that include isolated nucleic acid molecules, host cells that are genetically engineered with the recombinant vectors, and the production of at least one anti-IL-12/IL-23p40 antibody by recombinant techniques, as is well known in the art. See, e.g., Sambrook, et al., supra; Ausubel, et al., supra, each entirely incorporated herein by reference.

The polynucleotides can optionally be joined to a vector containing a selectable marker for propagation in a host. Generally, a plasmid vector is introduced in a precipitate, such as a calcium phosphate precipitate, or in a complex with a charged lipid. If the vector is a virus, it can be packaged in vitro using an appropriate packaging cell line and then transduced into host cells.

The DNA insert should be operatively linked to an appropriate promoter. The expression constructs will further contain sites for transcription initiation, termination and, in the transcribed region, a ribosome binding site for translation. The coding portion of the mature transcripts expressed by the constructs will preferably include a translation initiating at the beginning and a termination codon (e.g., UAA, UGA or UAG) appropriately positioned at the end of the mRNA to be translated, with UAA and UAG preferred for mammalian or eukaryotic cell expression.

Expression vectors will preferably but optionally include at least one selectable marker. Such markers include, e.g., but are not limited to, methotrexate (MTX), dihydrofolate reductase (DHFR, U.S. Pat. Nos. 4,399,216; 4,634,665; 4,656,134; 4,956,288; 5,149,636; 5,179,017, ampicillin, neomycin (G418), mycophenolic acid, or glutamine synthetase (GS, U.S. Pat. Nos. 5,122,464; 5,770,359; 5,827, 739) resistance for eukaryotic cell culture, and tetracycline or ampicillin resistance genes for culturing in E. coli and other bacteria or prokaryotics (the above patents are entirely incorporated hereby by reference). Appropriate culture mediums and conditions for the above-described host cells are known in the art. Suitable vectors will be readily apparent to the skilled artisan. Introduction of a vector construct into a host cell can be effected by calcium phosphate transfection, DEAE-dextran mediated transfection, cationic lipid-mediated transfection, electroporation, transduction, infection or other known methods. Such methods are described in the art, such as Sambrook, supra, Chapters 1-4 and 16-18; Ausubel, supra, Chapters 1, 9, 13, 15, 16.

At least one antibody used in the method of the present invention can be expressed in a modified form, such as a fusion protein, and can include not only secretion signals, but also additional heterologous functional regions. For instance, a region of additional amino acids, particularly charged amino acids, can be added to the N-terminus of an antibody to improve stability and persistence in the host cell, during purification, or during subsequent handling and storage. Also, peptide moieties can be added to an antibody of the present invention to facilitate purification. Such regions can be removed prior to final preparation of an antibody or at least one fragment thereof. Such methods are described in many standard laboratory manuals, such as Sambrook, supra, Chapters 17.29-17.42 and 18.1-18.74; Ausubel, supra, Chapters 16, 17 and 18.

Those of ordinary skill in the art are knowledgeable in the numerous expression systems available for expression of a nucleic acid encoding a protein used in the method of the present invention. Alternatively, nucleic acids can be expressed in a host cell by turning on (by manipulation) in a host cell that contains endogenous DNA encoding an antibody. Such methods are well known in the art, e.g., as described in U.S. Pat. Nos. 5,580,734, 5,641,670, 5,733,746, and 5,733,761, entirely incorporated herein by reference.

Illustrative of cell cultures useful for the production of the antibodies, specified portions or variants thereof, are mammalian cells. Mammalian cell systems often will be in the form of monolayers of cells although mammalian cell suspensions or bioreactors can also be used. A number of suitable host cell lines capable of expressing intact glycosylated proteins have been developed in the art, and include the COS-1 (e.g., ATCC CRL 1650), COS-7 (e.g., ATCC CRL-1651), HEK293, BHK21 (e.g., ATCC CRL-10), CHO (e.g., ATCC CRL 1610) and BSC-1 (e.g., ATCC CRL-26) cell lines, Cos-7 cells, CHO cells, hep G2 cells, P3X63Ag8.653, SP2/0-Ag14, 293 cells, HeLa cells and the like, which are readily available from, for example, American Type Culture Collection, Manassas, Va. (www.atcc.org). Preferred host cells include cells of lymphoid origin, such as myeloma and lymphoma cells. Particularly preferred host cells are P3X63Ag8.653 cells (ATCC Accession Number CRL-1580) and SP2/0-Ag14 cells (ATCC Accession Number CRL-1851). In a particularly preferred embodiment, the recombinant cell is a P3X63Ab8.653 or a SP2/0-Ag14 cell.

Expression vectors for these cells can include one or more of the following expression control sequences, such as, but not limited to, an origin of replication; a promoter (e.g., late or early SV40 promoters, the CMV promoter (U.S. Pat. Nos. 5,168,062; 5,385,839), an HSV tk promoter, a pgk (phosphoglycerate kinase) promoter, an EF-1 alpha promoter (U.S. Pat. No. 5,266,491), at least one human immunoglobulin promoter; an enhancer, and/or processing information sites, such as ribosome binding sites, RNA splice sites, polyadenylation sites (e.g., an SV40 large T Ag poly A addition site), and transcriptional terminator sequences. See, e.g., Ausubel et al., supra; Sambrook, et al., supra. Other cells useful for production of nucleic acids or proteins of the present invention are known and/or available, for instance, from the American Type Culture Collection Catalogue of Cell Lines and Hybridomas (www.atcc.org) or other known or commercial sources.

When eukaryotic host cells are employed, polyadenlyation or transcription terminator sequences are typically incorporated into the vector. An example of a terminator sequence is the polyadenlyation sequence from the bovine growth hormone gene. Sequences for accurate splicing of the transcript can also be included. An example of a splicing sequence is the VP1 intron from SV40 (Sprague, et al., J. Virol. 45:773-781 (1983)). Additionally, gene sequences to control replication in the host cell can be incorporated into the vector, as known in the art.

Purification of an Antibody

An anti-IL-12/IL-23p40 or IL-23 antibody can be recovered and purified from recombinant cell cultures by well-known methods including, but not limited to, protein A purification, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. High performance liquid chromatography ("HPLC") can also be employed for purification. See, e.g., Colligan, Current Protocols in Immunology, or Current Protocols in Protein Science, John Wiley & Sons, NY, N.Y., (1997-2001), e.g., Chapters 1, 4, 6, 8, 9, 10, each entirely incorporated herein by reference.

Antibodies used in the method of the present invention include naturally purified products, products of chemical synthetic procedures, and products produced by recombinant techniques from a eukaryotic host, including, for example, yeast, higher plant, insect and mammalian cells. Depending upon the host employed in a recombinant production procedure, the antibody can be glycosylated or can be non-glycosylated, with glycosylated preferred. Such methods are described in many standard laboratory manuals, such as Sambrook, supra, Sections 17.37-17.42; Ausubel, supra, Chapters 10, 12, 13, 16, 18 and 20, Colligan, Protein Science, supra, Chapters 12-14, all entirely incorporated herein by reference.

Anti-IL-12/IL-23p40 or IL-23 Antibodies

An anti-IL-12/IL-23p40 or IL-23 antibody according to the present invention includes any protein or peptide containing molecule that comprises at least a portion of an immunoglobulin molecule, such as but not limited to, at least one ligand binding portion (LBP), such as but not limited to, a complementarity determining region (CDR) of a heavy or light chain or a ligand binding portion thereof, a heavy chain or light chain variable region, a framework region (e.g., FR1, FR2, FR3, FR4 or fragment thereof, further optionally comprising at least one substitution, insertion or deletion), a heavy chain or light chain constant region, (e.g., comprising at least one CH1, hinge1, hinge2, hinge3, hinge4, CH2, or CH3 or fragment thereof, further optionally comprising at least one substitution, insertion or deletion), or any portion thereof, that can be incorporated into an antibody. An antibody can include or be derived from any mammal, such as but not limited to, a human, a mouse, a rabbit, a rat, a rodent, a primate, or any combination thereof, and the like.

Preferably, the human antibody or antigen-binding fragment binds human IL-12/IL-23p40 or IL-23 and, thereby, partially or substantially neutralizes at least one biological activity of the protein. An antibody, or specified portion or variant thereof, that partially or preferably substantially neutralizes at least one biological activity of at least one IL-12/IL-23p40 or IL-23 protein or fragment can bind the protein or fragment and thereby inhibit activities mediated through the binding of IL-12/IL-23p40 or IL-23 to the IL-12 and/or IL-23 receptor or through other IL-12/IL-23p40 or IL-23-dependent or mediated mechanisms. As used herein, the term "neutralizing antibody" refers to an antibody that can inhibit an IL-12/IL-23p40 or IL-23-dependent activity by about 20-120%, preferably by at least about 10, 20, 30, 40, 50, 55, 60, 65, 70, 75, 80, 85, 90, 91, 92, 93, 94, 95, 96, 97, 98, 99, 100% or more depending on the assay. The capacity of an anti-IL-12/IL-23p40 or IL-23 antibody to inhibit an IL-12/IL-23p40 or IL-23-dependent activity is preferably assessed by at least one suitable IL-12/IL-23p40 or IL-23 protein or receptor assay, as described herein and/or as known in the art. A human antibody can be of any class (IgG, IgA, IgM, IgE, IgD, etc.) or isotype and can comprise a kappa or lambda light chain. In one embodiment, the human antibody comprises an IgG heavy chain or defined fragment, for example, at least one of isotypes, IgG1, IgG2, IgG3 or IgG4 (e.g., γ1, γ2, γ3, γ4). Antibodies of this type can be prepared by employing a transgenic mouse or other trangenic non-human mammal comprising at least one human light chain (e.g., IgG, IgA, and IgM) transgenes as described herein and/or as known in the art. In another embodiment, the anti-IL-23 human antibody comprises an IgG1 heavy chain and an IgG1 light chain.

An antibody binds at least one specified epitope specific to at least one IL-12/IL-23p40 or IL-23 protein, subunit, fragment, portion or any combination thereof. The at least one epitope can comprise at least one antibody binding region that comprises at least one portion of the protein, which epitope is preferably comprised of at least one extracellular, soluble, hydrophillic, external or cytoplasmic portion of the protein.

Generally, the human antibody or antigen-binding fragment will comprise an antigen-binding region that comprises at least one human complementarity determining region (CDR1, CDR2 and CDR3) or variant of at least one heavy chain variable region and at least one human complementarity determining region (CDR1, CDR2 and CDR3) or variant of at least one light chain variable region. The CDR sequences can be derived from human germline sequences or closely match the germline sequences. For example, the CDRs from a synthetic library derived from the original non-human CDRs can be used. These CDRs can be formed by incorporation of conservative substitutions from the original non-human sequence. In another particular embodiment, the antibody or antigen-binding portion or variant can have an antigen-binding region that comprises at least a portion of at least one light chain CDR (i.e., CDR1, CDR2 and/or CDR3) having the amino acid sequence of the corresponding CDRs 1, 2 and/or 3.

Such antibodies can be prepared by chemically joining together the various portions (e.g., CDRs, framework) of the antibody using conventional techniques, by preparing and expressing a (i.e., one or more) nucleic acid molecule that encodes the antibody using conventional techniques of recombinant DNA technology or by using any other suitable method.

In one embodiment, an anti-IL-12/23p40 antibody useful for the invention is a monoclonal antibody, preferably a human mAb, comprising heavy chain complementarity determining regions (CDRs) HCDR1, HCDR2, and HCDR3 of SEQ ID NOs: 1, 2, and 3, respectively; and light chain CDRs LCDR1, LCDR2, and LCDR3, of SEQ ID NOs: 4, 5, and 6, respectively.

The anti-IL-12/IL-23p40 or IL-23 specific antibody can comprise at least one of a heavy or light chain variable region having a defined amino acid sequence. For example, in a preferred embodiment, the anti-IL-12/IL-23p40 or IL-23 antibody comprises an anti-IL-12/IL-23p40 antibody with a heavy chain variable region comprising an amino acid sequence at least 85%, preferably at least 90%, more preferably at least 95%, and most preferably 100% identical to SEQ ID NO:7, and a light chain variable region comprising an amino acid sequence at least 85%, preferably at least 90%, more preferably at least 95%, and most preferably 100% identical to SEQ ID NO:8.

The anti-IL-12/IL-23p40 or IL-23 specific antibody can also comprise at least one of a heavy or light chain having a defined amino acid sequence. In another preferred embodiment, the anti-IL-12/IL-23p40 or IL-23 antibody comprises an anti-IL-12/IL-23p40 antibody with a heavy chain comprising an amino acid sequence at least 85%, preferably at least 90%, more preferably at least 95%, and most preferably 100% identical to SEQ ID NO:10, and a light chain variable region comprising an amino acid sequence at least 85%, preferably at least 90%, more preferably at least 95%, and most preferably 100% identical to SEQ ID NO:11.

Preferably, the anti-IL-12/23p40 antibody is ustekinumab (Stelara®), comprising a heavy chain having the amino acid sequence of SEQ ID NO: 10 and a light chain comprising the amino acid sequence of SEQ ID NO: 11. Other examples of anti-IL12/23p40 antibodies useful for the invention include, but are not limited to, Briakinumab (ABT-874, Abbott) and other antibodies described in U.S. Pat. Nos. 6,914,128, 7,247,711, 7,700,739, the entire contents of which are incorporated herein by reference).

The invention also relates to antibodies, antigen-binding fragments, immunoglobulin chains and CDRs comprising amino acids in a sequence that is substantially the same as an amino acid sequence described herein. Preferably, such antibodies or antigen-binding fragments and antibodies comprising such chains or CDRs can bind human IL-12/IL-23p40 or IL-23 with high affinity (e.g., KD less than or equal to about $10^{-9}$M). Amino acid sequences that are substantially the same as the sequences described herein include sequences comprising conservative amino acid substitutions, as well as amino acid deletions and/or insertions. A conservative amino acid substitution refers to the replacement of a first amino acid by a second amino acid that has chemical and/or physical properties (e.g., charge, structure, polarity, hydrophobicity/hydrophilicity) that are similar to those of the first amino acid. Conservative substitutions include, without limitation, replacement of one amino acid by another within the following groups: lysine (K), arginine (R) and histidine (H); aspartate (D) and glutamate (E); asparagine (N), glutamine (Q), serine (S), threonine (T), tyrosine (Y), K, R, H, D and E; alanine (A), valine (V), leucine (L), isoleucine (I), proline (P), phenylalanine (F), tryptophan (W), methionine (M), cysteine (C) and glycine (G); F, W and Y; C, S and T.

Antibodies that bind to human IL-12/IL-23p40 or IL-23 and that comprise a defined heavy or light chain variable region can be prepared using suitable methods, such as phage display (Katsube, Y., et al., Int J Mol. Med, 1(5):863-868 (1998)) or methods that employ transgenic animals, as known in the art and/or as described herein. For example, a transgenic mouse, comprising a functionally rearranged human immunoglobulin heavy chain transgene and a transgene comprising DNA from a human immunoglobulin light chain locus that can undergo functional rearrangement, can be immunized with human IL-12/IL-23p40 or IL-23 or a fragment thereof to elicit the production of antibodies. If desired, the antibody producing cells can be isolated and hybridomas or other immortalized antibody-producing cells can be prepared as described herein and/or as known in the art. Alternatively, the antibody, specified portion or variant can be expressed using the encoding nucleic acid or portion thereof in a suitable host cell.

An anti-IL-12/IL-23p40 or IL-23 antibody used in the method of the present invention can include one or more amino acid substitutions, deletions or additions, either from natural mutations or human manipulation, as specified herein.

The number of amino acid substitutions a skilled artisan would make depends on many factors, including those described above. Generally speaking, the number of amino acid substitutions, insertions or deletions for any given anti-IL-12/IL-23p40 or IL-23 antibody, fragment or variant will not be more than 40, 30, 20, 19, 18, 17, 16, 15, 14, 13, 12, 11, 10, 9, 8, 7, 6, 5, 4, 3, 2, 1, such as 1-30 or any range or value therein, as specified herein.

Amino acids in an anti-IL-12/IL-23p40 or IL-23 specific antibody that are essential for function can be identified by methods known in the art, such as site-directed mutagenesis or alanine-scanning mutagenesis (e.g., Ausubel, supra, Chapters 8, 15; Cunningham and Wells, Science 244:1081-1085 (1989)). The latter procedure introduces single alanine mutations at every residue in the molecule. The resulting mutant molecules are then tested for biological activity, such as, but not limited to, at least one IL-12/IL-23p40 or IL-23 neutralizing activity. Sites that are critical for antibody binding can also be identified by structural analysis, such as crystallization, nuclear magnetic resonance or photoaffinity labeling (Smith, et al., J. Mol. Biol. 224:899-904 (1992) and de Vos, et al., Science 255:306-312 (1992)).

Anti-IL-12/IL-23p40 or IL-23 antibodies can include, but are not limited to, at least one portion, sequence or combination selected from 5 to all of the contiguous amino acids of at least one of SEQ ID NOs 1, 2, 3, 4, 5, 6, 7, 8, 10, or 11.

IL-12/IL-23p40 or IL-23 antibodies or specified portions or variants can include, but are not limited to, at least one portion, sequence or combination selected from at least 3-5 contiguous amino acids of the SEQ ID NOs above; 5-17 contiguous amino acids of the SEQ ID NOs above, 5-10 contiguous amino acids of the SEQ ID NOs above, 5-11 contiguous amino acids of the SEQ ID NOs above, 5-7 contiguous amino acids of the SEQ ID NOs above; 5-9 contiguous amino acids of the SEQ ID NOs above.

An anti-IL-12/IL-23p40 or IL-23 antibody can further optionally comprise a polypeptide of at least one of 70-100% of 5, 17, 10, 11, 7, 9, 119, 108, 449, or 214 contiguous amino acids of the SEQ ID NOs above. In one embodiment, the amino acid sequence of an immunoglobulin chain, or portion thereof (e.g., variable region, CDR) has about 70-100% identity (e.g., 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100 or any range or value therein) to the amino acid sequence of the corresponding chain of at least one of the SEQ ID NOs above. For example, the amino acid sequence of a light chain variable region can be compared with the sequence of the SEQ ID NOs above, or the amino acid sequence of a heavy chain CDR3 can be compared with the SEQ ID NOs above. Preferably, 70-100% amino acid identity (i.e., 90, 91, 92, 93, 94, 95, 96, 97, 98, 99, 100 or any range or value therein) is determined using a suitable computer algorithm, as known in the art.

"Identity," as known in the art, is a relationship between two or more polypeptide sequences or two or more polynucleotide sequences, as determined by comparing the sequences. In the art, "identity" also means the degree of sequence relatedness between polypeptide or polynucleotide sequences, as determined by the match between strings of such sequences.

"Identity" and "similarity" can be readily calculated by known methods, including, but not limited to, those described in Computational Molecular Biology, Lesk, A. M., ed., Oxford University Press, New York, 1988; Biocomputing:Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., Siam J. Applied Math., 48:1073 (1988). In addition, values for percentage identity can be obtained from amino acid and nucleotide sequence alignments generated using the default settings for the AlignX component of Vector NTI Suite 8.0 (Informax, Frederick, Md.).

Preferred methods to determine identity are designed to give the largest match between the sequences tested. Methods to determine identity and similarity are codified in publicly available computer programs. Preferred computer program methods to determine identity and similarity between two sequences include, but are not limited to, the GCG program package (Devereux, J., et al., Nucleic Acids Research 12(1): 387 (1984)), BLASTP, BLASTN, and FASTA (Atschul, S. F. et al., J. Molec. Biol. 215:403-410 (1990)). The BLAST X program is publicly available from NCBI and other sources (BLAST Manual, Altschul, S., et al., NCBINLM NIH Bethesda, Md. 20894: Altschul, S., et al., J. Mol. Biol. 215:403-410 (1990). The well-known Smith Waterman algorithm can also be used to determine identity.

Exemplary heavy chain and light chain variable regions sequences and portions thereof are provided in the SEQ ID NOs above. The antibodies of the present invention, or specified variants thereof, can comprise any number of contiguous amino acid residues from an antibody of the present invention, wherein that number is selected from the group of integers consisting of from 10-100% of the number of contiguous residues in an anti-IL-12/IL-23p40 or IL-23 antibody. Optionally, this subsequence of contiguous amino acids is at least about 10, 20, 30, 40, 50, 60, 70, 80, 90, 100, 110, 120, 130, 140, 150, 160, 170, 180, 190, 200, 210, 220, 230, 240, 250 or more amino acids in length, or any range or value therein. Further, the number of such subsequences can be any integer selected from the group consisting of from 1 to 20, such as at least 2, 3, 4, or 5.

As those of skill will appreciate, the present invention includes at least one biologically active antibody of the present invention. Biologically active antibodies have a specific activity at least 20%, 30%, or 40%, and, preferably, at least 50%, 60%, or 70%, and, most preferably, at least 80%, 90%, or 95%-100% or more (including, without limitation, up to 10 times the specific activity) of that of the native (non-synthetic), endogenous or related and known antibody. Methods of assaying and quantifying measures of enzymatic activity and substrate specificity are well known to those of skill in the art.

In another aspect, the invention relates to human antibodies and antigen-binding fragments, as described herein, which are modified by the covalent attachment of an organic moiety. Such modification can produce an antibody or antigen-binding fragment with improved pharmacokinetic properties (e.g., increased in vivo serum half-life). The organic moiety can be a linear or branched hydrophilic polymeric group, fatty acid group, or fatty acid ester group. In particular embodiments, the hydrophilic polymeric group can have a molecular weight of about 800 to about 120,000 Daltons and can be a polyalkane glycol (e.g., polyethylene glycol (PEG), polypropylene glycol (PPG)), carbohydrate polymer, amino acid polymer or polyvinyl pyrolidone, and the fatty acid or fatty acid ester group can comprise from about eight to about forty carbon atoms.

The modified antibodies and antigen-binding fragments can comprise one or more organic moieties that are covalently bonded, directly or indirectly, to the antibody. Each organic moiety that is bonded to an antibody or antigen-binding fragment of the invention can independently be a hydrophilic polymeric group, a fatty acid group or a fatty acid ester group. As used herein, the term "fatty acid" encompasses mono-carboxylic acids and di-carboxylic acids. A "hydrophilic polymeric group," as the term is used herein, refers to an organic polymer that is more soluble in water than in octane. For example, polylysine is more soluble in water than in octane. Thus, an antibody modified by the covalent attachment of polylysine is encompassed by the invention. Hydrophilic polymers suitable for modifying antibodies of the invention can be linear or branched and include, for example, polyalkane glycols (e.g., PEG, monomethoxy-polyethylene glycol (mPEG), PPG and the like), carbohydrates (e.g., dextran, cellulose, oligosaccharides, polysaccharides and the like), polymers of hydrophilic amino acids (e.g., polylysine, polyarginine, polyaspartate and the like), polyalkane oxides (e.g., polyethylene oxide, polypropylene oxide and the like) and polyvinyl pyrolidone. Preferably, the hydrophilic polymer that modifies the antibody of the invention has a molecular weight of about 800 to about 150,000 Daltons as a separate molecular entity. For example, PEG5000 and PEG20,000, wherein the subscript is the average molecular weight of the polymer in Daltons, can be used. The hydrophilic polymeric group can be substituted with one to about six alkyl, fatty acid or fatty acid ester groups. Hydrophilic polymers that are substituted with a fatty acid or fatty acid ester group can be prepared by employing suitable methods. For example, a polymer comprising an amine group can be coupled to a carboxylate of the fatty acid or fatty acid ester, and an activated carboxylate (e.g., activated with N, N-carbonyl diimidazole) on a fatty acid or fatty acid ester can be coupled to a hydroxyl group on a polymer.

Fatty acids and fatty acid esters suitable for modifying antibodies of the invention can be saturated or can contain one or more units of unsaturation. Fatty acids that are suitable for modifying antibodies of the invention include, for example, n-dodecanoate (C12, laurate), n-tetradecanoate (C14, myristate), n-octadecanoate (C18, stearate), n-eicosanoate (C20, arachidate), n-docosanoate (C22, behenate), n-triacontanoate (C30), n-tetracontanoate (C40), cis-Δ9-octadecanoate (C18, oleate), all cis-Δ5,8,11,14-eicosatetraenoate (C20, arachidonate), octanedioic acid, tetradecanedioic acid, octadecanedioic acid, docosanedioic acid, and the like. Suitable fatty acid esters include mono-esters of dicarboxylic acids that comprise a linear or branched lower alkyl group. The lower alkyl group can comprise from one to about twelve, preferably, one to about six, carbon atoms.

The modified human antibodies and antigen-binding fragments can be prepared using suitable methods, such as by reaction with one or more modifying agents. A "modifying agent" as the term is used herein, refers to a suitable organic group (e.g., hydrophilic polymer, a fatty acid, a fatty acid ester) that comprises an activating group. An "activating group" is a chemical moiety or functional group that can, under appropriate conditions, react with a second chemical group thereby forming a covalent bond between the modifying agent and the second chemical group. For example, amine-reactive activating groups include electrophilic groups, such as tosylate, mesylate, halo (chloro, bromo, fluoro, iodo), N-hydroxysuccinimidyl esters (NHS), and the like. Activating groups that can react with thiols include, for example, maleimide, iodoacetyl, acrylolyl, pyridyl disulfides, 5-thiol-2-nitrobenzoic acid thiol (TNB-thiol), and the like. An aldehyde functional group can be coupled to amine- or hydrazide-containing molecules, and an azide group can react with a trivalent phosphorous group to form phosphoramidate or phosphorimide linkages. Suitable methods to introduce activating groups into molecules are known in the art (see for example, Hermanson, G. T., Bioconjugate Techniques, Academic Press: San Diego, Calif. (1996)). An activating group can be bonded directly to the organic group (e.g., hydrophilic polymer, fatty acid, fatty acid ester), or through a linker moiety, for example, a divalent C1-C12 group wherein one or more carbon atoms can be replaced by a heteroatom, such as oxygen, nitrogen or sulfur. Suitable linker moieties include, for example, tetraethylene glycol, —(CH2)3-, —NH—(CH2)6-NH—, —(CH2)2-NH— and —CH2-O—CH2-CH2-O—CH2-CH2-O—CH—NH—. Modifying agents that comprise a linker moiety can be produced, for example, by reacting a mono-Boc-alkyl-diamine (e.g., mono-Boc-ethylenediamine, mono-Boc-diaminohexane) with a fatty acid in the presence of 1-ethyl-3-(3-dimethylaminopropyl) carbodiimide (EDC) to form an amide bond between the free amine and the fatty acid carboxylate. The Boc protecting group can be removed from the product by treatment with trifluoroacetic acid (TFA) to expose a primary amine that can be coupled to another carboxylate, as described, or can be reacted with maleic anhydride and the resulting product cyclized to produce an activated maleimido derivative of the fatty acid. (See, for example, Thompson, et al., WO 92/16221, the entire teachings of which are incorporated herein by reference.)

The modified antibodies can be produced by reacting a human antibody or antigen-binding fragment with a modifying agent. For example, the organic moieties can be bonded to the antibody in a non-site specific manner by employing an amine-reactive modifying agent, for example, an NHS ester of PEG. Modified human antibodies or antigen-binding fragments can also be prepared by reducing disulfide bonds (e.g., intra-chain disulfide bonds) of an antibody or antigen-binding fragment. The reduced antibody or antigen-binding fragment can then be reacted with a thiol-reactive modifying agent to produce the modified antibody of the invention. Modified human antibodies and antigen-binding fragments comprising an organic moiety that is bonded to specific sites of an antibody of the present invention can be prepared using suitable methods, such as reverse proteolysis (Fisch et al., Bioconjugate Chem., 3:147-153 (1992); Werlen et al., Bioconjugate Chem., 5:411-417 (1994); Kumaran et al., Protein Sci. 6(10):2233-2241 (1997); Itoh et al., Bioorg. Chem., 24(1): 59-68 (1996); Capellas et al., Biotechnol. Bioeng., 56(4):456-463 (1997)), and the methods described in Hermanson, G. T., Bioconjugate Techniques, Academic Press: San Diego, Calif. (1996).

The method of the present invention also uses an anti-IL-12/IL-23p40 or IL-23 antibody composition comprising at least one, at least two, at least three, at least four, at least five, at least six or more anti-IL-12/IL-23p40 or IL-23 antibodies thereof, as described herein and/or as known in the art that are provided in a non-naturally occurring composition, mixture or form. Such compositions comprise non-naturally occurring compositions comprising at least one or two full length, C- and/or N-terminally deleted variants, domains, fragments, or specified variants, of the anti-IL-12/IL-23p40 or IL-23 antibody amino acid sequence selected from the group consisting of 70-100% of the contiguous amino acids of the SEQ ID NOs above, or specified fragments, domains or variants thereof. Preferred anti-IL-12/IL-23p40 or IL-23 antibody compositions include at least one or two full length, fragments, domains or variants as at least one CDR or LBP containing portions of the anti-IL-12/IL-23p40 or IL-23 antibody sequence described herein, for example, 70-100% of the SEQ ID NOs above, or specified fragments, domains or variants thereof. Further preferred compositions comprise, for example, 40-99% of at least one of 70-100% of the SEQ ID NOs above, etc., or specified fragments, domains or variants thereof. Such composition percentages are by weight, volume, concentration, molarity, or molality as liquid or dry solutions, mixtures, suspension, emulsions, particles, powder, or colloids, as known in the art or as described herein.

Antibody Compositions Comprising Further Therapeutically Active Ingredients

The antibody compositions used in the method of the invention can optionally further comprise an effective amount of at least one compound or protein selected from at least one of an anti-infective drug, a cardiovascular (CV) system drug, a central nervous system (CNS) drug, an autonomic nervous system (ANS) drug, a respiratory tract drug, a gastrointestinal (GI) tract drug, a hormonal drug, a drug for fluid or electrolyte balance, a hematologic drug, an antineoplastic, an immunomodulation drug, an ophthalmic, otic or nasal drug, a topical drug, a nutritional drug or the like. Such drugs are well known in the art, including formulations, indications, dosing and administration for each presented herein (see, e.g., Nursing 2001 Handbook of Drugs, 21st edition, Springhouse Corp., Springhouse, P A, 2001; Health Professional's Drug Guide 2001, ed., Shannon, Wilson, Stang, Prentice-Hall, Inc, Upper Saddle River, N.J.; Pharmcotherapy Handbook, Wells et al., ed., Appleton & Lange, Stamford, Conn., each entirely incorporated herein by reference).

By way of example of the drugs that can be combined with the antibodies for the method of the present invention, the anti-infective drug can be at least one selected from amebicides or at least one antiprotozoals, anthelmintics, antifungals, antimalarials, antituberculotics or at least one antileprotics, aminoglycosides, penicillins, cephalosporins, tetracyclines, sulfonamides, fluoroquinolones, antivirals, macrolide anti-infectives, and miscellaneous anti-infectives. The hormonal drug can be at least one selected from corticosteroids, androgens or at least one anabolic steroid, estrogen or at least one progestin, gonadotropin, antidiabetic drug or at least one glucagon, thyroid hormone, thyroid hormone antagonist, pituitary hormone, and parathyroid-like drug. The at least one cephalosporin can be at least one selected from cefaclor, cefadroxil, cefazolin sodium, cefdinir, cefepime hydrochloride, cefixime, cefmetazole sodium, cefonicid sodium, cefoperazone sodium, cefotaxime sodium, cefotetan disodium, cefoxitin sodium, cefpodoxime proxetil, cefprozil, ceftazidime, ceftibuten, ceftizoxime sodium, ceftriaxone sodium, cefuroxime axetil, cefuroxime sodium, cephalexin hydrochloride, cephalexin monohydrate, cephradine, and loracarbef.

The at least one coricosteroid can be at least one selected from betamethasone, betamethasone acetate or betamethasone sodium phosphate, betamethasone sodium phosphate, cortisone acetate, dexamethasone, dexamethasone acetate, dexamethasone sodium phosphate, fludrocortisone acetate, hydrocortisone, hydrocortisone acetate, hydrocortisone cypionate, hydrocortisone sodium phosphate, hydrocortisone sodium succinate, methylprednisolone, methylprednisolone acetate, methylprednisolone sodium succinate, prednisolone, prednisolone acetate, prednisolone sodium phosphate, prednisolone tebutate, prednisone, triamcinolone, triamcinolone acetonide, and triamcinolone diacetate. The at least one androgen or anabolic steroid can be at least one selected from danazol, fluoxymesterone, methyltestosterone, nandrolone decanoate, nandrolone phenpropionate, testosterone, testosterone cypionate, testosterone enanthate, testosterone propionate, and testosterone transdermal system.

The at least one immunosuppressant can be at least one selected from azathioprine, basiliximab, cyclosporine, daclizumab, lymphocyte immune globulin, muromonab-CD3, mycophenolate mofetil, mycophenolate mofetil hydrochloride, sirolimus, 6-mercaptopurine, methotrexate, mizoribine, and tacrolimus.

The at least one local anti-infective can be at least one selected from acyclovir, amphotericin B, azelaic acid cream, bacitracin, butoconazole nitrate, clindamycin phosphate, clotrimazole, econazole nitrate, erythromycin, gentamicin sulfate, ketoconazole, mafenide acetate, metronidazole (topical), miconazole nitrate, mupirocin, naftifine hydrochloride, neomycin sulfate, nitrofurazone, nystatin, silver sulfadiazine, terbinafine hydrochloride, terconazole, tetracycline hydrochloride, tioconazole, and tolnaftate. The at least one scabicide or pediculicide can be at least one selected from crotamiton, lindane, permethrin, and pyrethrins. The at least one topical corticosteroid can be at least one selected from betamethasone dipropionate, betamethasone valerate, clobetasol propionate, desonide, desoximetasone, dexamethasone, dexamethasone sodium phosphate, diflorasone diacetate, fluocinolone acetonide, fluocinonide, flurandrenolide, fluticasone propionate, halcionide, hydrocortisone, hydrocortisone acetate, hydrocortisone butyrate, hydrocorisone valerate, mometasone furoate, and triamcinolone acetonide. (See, e.g., pp. 1098-1136 of Nursing 2001 Drug Handbook.)

Anti-IL-12/IL-23p40 or IL-23 antibody compositions can further comprise at least one of any suitable and effective amount of a composition or pharmaceutical composition comprising at least one anti-IL-12/IL-23p40 or IL-23 antibody contacted or administered to a cell, tissue, organ, animal or subject in need of such modulation, treatment or therapy, optionally further comprising at least one selected from at least one TNF antagonist (e.g., but not limited to a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, eternacept, CDP-571, CDP-870, afelimomab, lenercept, and the like), an antirheumatic (e.g., methotrexate, auranofin, aurothioglucose, azathioprine, etanercept, gold sodium thiomalate, hydroxychloroquine sulfate, leflunomide, sulfasalzine), an immunization, an immunoglobulin, an immunosuppressive (e.g., azathioprine, basiliximab, cyclosporine, daclizumab), a cytokine or a cytokine antagonist. Non-limiting examples of such cytokines include, but are not limited to, any of IL-1 to IL-23 et al. (e.g., IL-1, IL-2, etc.). Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000), each of which references are entirely incorporated herein by reference.

Anti-IL-12/IL-23p40 or IL-23 antibody compounds, compositions or combinations used in the method of the present invention can further comprise at least one of any suitable auxiliary, such as, but not limited to, diluent, binder, stabilizer, buffers, salts, lipophilic solvents, preservative, adjuvant or the like. Pharmaceutically acceptable auxiliaries are preferred. Non-limiting examples of, and methods of preparing such sterile solutions are well known in the art, such as, but limited to, Gennaro, Ed., Remington's Pharmaceutical Sciences, 18th Edition, Mack Publishing Co. (Easton, Pa.) 1990. Pharmaceutically acceptable carriers can be routinely selected that are suitable for the mode of administration, solubility and/or stability of the anti-IL-12/IL-23p40, fragment or variant composition as well known in the art or as described herein.

Pharmaceutical excipients and additives useful in the present composition include, but are not limited to, proteins, peptides, amino acids, lipids, and carbohydrates (e.g., sugars, including monosaccharides, di-, tri-, tetra-, and oligosaccharides; derivatized sugars, such as alditols, aldonic acids, esterified sugars and the like; and polysaccharides or sugar polymers), which can be present singly or in combination, comprising alone or in combination 1-99.99% by weight or volume. Exemplary protein excipients include serum albumin, such as human serum albumin (HSA), recombinant human albumin (rHA), gelatin, casein, and the like. Representative amino acid/antibody components, which can also function in a buffering capacity, include alanine, glycine, arginine, betaine, histidine, glutamic acid, aspartic acid, cysteine, lysine, leucine, isoleucine, valine, methionine, phenylalanine, aspartame, and the like. One preferred amino acid is glycine.

Carbohydrate excipients suitable for use in the invention include, for example, monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol sorbitol (glucitol), myoinositol and the like. Preferred carbohydrate excipients for use in the present invention are mannitol, trehalose, and raffinose.

Anti-IL-12/IL-23p40 or IL-23 antibody compositions can also include a buffer or a pH adjusting agent; typically, the buffer is a salt prepared from an organic acid or base. Representative buffers include organic acid salts, such as salts of citric acid, ascorbic acid, gluconic acid, carbonic acid, tartaric acid, succinic acid, acetic acid, or phthalic acid; Tris, tromethamine hydrochloride, or phosphate buffers. Preferred buffers for use in the present compositions are organic acid salts, such as citrate.

Additionally, anti-IL-12/IL-23p40 or IL-23 antibody compositions can include polymeric excipients/additives, such as polyvinylpyrrolidones, ficolls (a polymeric sugar), dextrates (e.g., cyclodextrins, such as 2-hydroxypropyl-β-cyclodextrin), polyethylene glycols, flavoring agents, antimicrobial agents, sweeteners, antioxidants, antistatic agents, surfactants (e.g., polysorbates, such as "TWEEN 20" and "TWEEN 80"), lipids (e.g., phospholipids, fatty acids), steroids (e.g., cholesterol), and chelating agents (e.g., EDTA).

These and additional known pharmaceutical excipients and/or additives suitable for use in the anti-IL-12/IL-23p40 or IL-23 antibody, portion or variant compositions according to the invention are known in the art, e.g., as listed in "Remington: The Science & Practice of Pharmacy," 19th ed., Williams & Williams, (1995), and in the "Physician's Desk Reference," 52nd ed., Medical Economics, Montvale, N.J. (1998), the disclosures of which are entirely incorporated herein by reference. Preferred carrier or excipient materials are carbohydrates (e.g., saccharides and alditols) and buffers (e.g., citrate) or polymeric agents. An exemplary carrier molecule is the mucopolysaccharide, hyaluronic acid, which can be useful for intraarticular delivery.

Formulations

As noted above, the invention provides for stable formulations, which preferably comprise a phosphate buffer with saline or a chosen salt, as well as preserved solutions and formulations containing a preservative as well as multi-use preserved formulations suitable for pharmaceutical or veterinary use, comprising at least one anti-IL-12/IL-23p40 or IL-23 antibody in a pharmaceutically acceptable formulation. Preserved formulations contain at least one known preservative or optionally selected from the group consisting of at least one phenol, m-cresol, p-cresol, o-cresol, chlorocresol, benzyl alcohol, phenylmercuric nitrite, phenoxyethanol, formaldehyde, chlorobutanol, magnesium chloride (e.g., hexahydrate), alkylparaben (methyl, ethyl, propyl, butyl and the like), benzalkonium chloride, benzethonium chloride, sodium dehydroacetate and thimerosal, or mixtures thereof in an aqueous diluent. Any suitable concentration or mixture can be used as known in the art, such as 0.001-5%, or any range or value therein, such as, but not limited to 0.001, 0.003, 0.005, 0.009, 0.01, 0.02, 0.03, 0.05, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.3, 4.5, 4.6, 4.7, 4.8, 4.9, or any range or value therein. Non-limiting examples include, no preservative, 0.1-2% m-cresol (e.g., 0.2, 0.3. 0.4, 0.5, 0.9, 1.0%), 0.1-3% benzyl alcohol (e.g., 0.5, 0.9, 1.1, 1.5, 1.9, 2.0, 2.5%), 0.001-0.5% thimerosal (e.g., 0.005, 0.01), 0.001-2.0% phenol (e.g., 0.05, 0.25, 0.28, 0.5, 0.9, 1.0%), 0.0005-1.0% alkylparaben(s) (e.g., 0.00075, 0.0009, 0.001, 0.002, 0.005, 0.0075, 0.009, 0.01, 0.02, 0.05, 0.075, 0.09, 0.1, 0.2, 0.3, 0.5, 0.75, 0.9, 1.0%), and the like.

As noted above, the method of the invention uses an article of manufacture, comprising packaging material and at least one vial comprising a solution of at least one anti-IL-12/IL-23p40 or IL-23 antibody with the prescribed buffers and/or preservatives, optionally in an aqueous diluent, wherein said packaging material comprises a label that indicates that such solution can be held over a period of 1, 2, 3, 4, 5, 6, 9, 12, 18, 20, 24, 30, 36, 40, 48, 54, 60, 66, 72 hours or greater. The invention further uses an article of manufacture, comprising packaging material, a first vial comprising lyophilized anti-IL-12/IL-23p40 or IL-23 antibody, and a second vial comprising an aqueous diluent of prescribed buffer or preservative, wherein said packaging material comprises a label that instructs a subject to reconstitute the anti-IL-12/IL-23p40 or IL-23 antibody in the aqueous diluent to form a solution that can be held over a period of twenty-four hours or greater.

The anti-IL-12/IL-23p40 or IL-23 antibody used in accordance with the present invention can be produced by recombinant means, including from mammalian cell or transgenic preparations, or can be purified from other biological sources, as described herein or as known in the art.

The range of the anti-IL-12/IL-23p40 or IL-23 antibody includes amounts yielding upon reconstitution, if in a wet/dry system, concentrations from about 1.0 µg/ml to about 1000 mg/ml, although lower and higher concentrations are operable and are dependent on the intended delivery vehicle, e.g., solution formulations will differ from transdermal patch, pulmonary, transmucosal, or osmotic or micro pump methods.

Preferably, the aqueous diluent optionally further comprises a pharmaceutically acceptable preservative. Preferred preservatives include those selected from the group consisting of phenol, m-cresol, p-cresol, o-cresol, chlorocresol, benzyl alcohol, alkylparaben (methyl, ethyl, propyl, butyl and the like), benzalkonium chloride, benzethonium chloride, sodium dehydroacetate and thimerosal, or mixtures thereof. The concentration of preservative used in the formulation is a concentration sufficient to yield an antimicrobial effect. Such concentrations are dependent on the preservative selected and are readily determined by the skilled artisan.

Other excipients, e.g., isotonicity agents, buffers, antioxidants, and preservative enhancers, can be optionally and preferably added to the diluent. An isotonicity agent, such as glycerin, is commonly used at known concentrations. A physiologically tolerated buffer is preferably added to provide improved pH control. The formulations can cover a wide range of pHs, such as from about pH 4 to about pH 10, and preferred ranges from about pH 5 to about pH 9, and a most preferred range of about 6.0 to about 8.0. Preferably, the formulations of the present invention have a pH between about 6.8 and about 7.8. Preferred buffers include phosphate buffers, most preferably, sodium phosphate, particularly, phosphate buffered saline (PBS).

Other additives, such as a pharmaceutically acceptable solubilizers like Tween 20 (polyoxyethylene (20) sorbitan monolaurate), Tween 40 (polyoxyethylene (20) sorbitan monopalmitate), Tween 80 (polyoxyethylene (20) sorbitan monooleate), Pluronic F68 (polyoxyethylene polyoxypropylene block copolymers), and PEG (polyethylene glycol) or non-ionic surfactants, such as polysorbate 20 or 80 or poloxamer 184 or 188, Pluronic® polyls, other block co-polymers, and chelators, such as EDTA and EGTA, can optionally be added to the formulations or compositions to reduce aggregation. These additives are particularly useful if a pump or plastic container is used to administer the formulation. The presence of pharmaceutically acceptable surfactant mitigates the propensity for the protein to aggregate.

The formulations can be prepared by a process which comprises mixing at least one anti-IL-12/IL-23p40 or IL-23 antibody and a preservative selected from the group consisting of phenol, m-cresol, p-cresol, o-cresol, chlorocresol, benzyl alcohol, alkylparaben, (methyl, ethyl, propyl, butyl and the like), benzalkonium chloride, benzethonium chloride, sodium dehydroacetate and thimerosal or mixtures thereof in an aqueous diluent. Mixing the at least one anti-IL-12/IL-23p40 or IL-23 specific antibody and preservative in an aqueous diluent is carried out using conventional dissolution and mixing procedures. To prepare a suitable formulation, for example, a measured amount of at least one anti-IL-12/IL-23p40 or IL-23 antibody in buffered solution is combined with the desired preservative in a buffered solution in quantities sufficient to provide the protein and preservative at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The formulations can be provided to subjects as clear solutions or as dual vials comprising a vial of lyophilized anti-IL-12/IL-23p40 or IL-23 specific antibody that is reconstituted with a second vial containing water, a preservative and/or excipients, preferably, a phosphate buffer and/or saline and a chosen salt, in an aqueous diluent. Either a single solution vial or dual vial requiring reconstitution can be reused multiple times and can suffice for a single or multiple cycles of subject treatment and thus can provide a more convenient treatment regimen than currently available.

The present articles of manufacture are useful for administration over a period ranging from immediate to twenty-four hours or greater. Accordingly, the presently claimed articles of manufacture offer significant advantages to the subject. Formulations of the invention can optionally be safely stored at temperatures of from about 2° C. to about 40° C. and retain the biologically activity of the protein for extended periods of time, thus allowing a package label indicating that the solution can be held and/or used over a period of 6, 12, 18, 24, 36, 48, 72, or 96 hours or greater. If preserved diluent is used, such label can include use up to 1-12 months, one-half, one and a half, and/or two years.

The solutions of anti-IL-12/IL-23p40 or IL-23 specific antibody can be prepared by a process that comprises mixing at least one antibody in an aqueous diluent. Mixing is carried out using conventional dissolution and mixing procedures. To prepare a suitable diluent, for example, a measured amount of at least one antibody in water or buffer is combined in quantities sufficient to provide the protein and, optionally, a preservative or buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The claimed products can be provided to subjects as clear solutions or as dual vials comprising a vial of lyophilized at least one anti-IL-12/IL-23p40 or IL-23 specific antibody that is reconstituted with a second vial containing the aqueous diluent. Either a single solution vial or dual vial requiring reconstitution can be reused multiple times and can suffice for a single or multiple cycles of subject treatment and thus provides a more convenient treatment regimen than currently available.

The claimed products can be provided indirectly to subjects by providing to pharmacies, clinics, or other such institutions and facilities, clear solutions or dual vials comprising a vial of lyophilized at least one anti-IL-12/IL-23p40 or IL-23 specific antibody that is reconstituted with a second vial containing the aqueous diluent. The clear solution in this case can be up to one liter or even larger in size, providing a large reservoir from which smaller portions of the at least one antibody solution can be retrieved one or multiple times for transfer into smaller vials and provided by the pharmacy or clinic to their customers and/or subjects.

Recognized devices comprising single vial systems include pen-injector devices for delivery of a solution, such as BD Pens, BD Autojector®, Humaject®, NovoPen®, B-D® Pen, AutoPen®, and OptiPen®, GenotropinPen®, Genotronorm Pen®, Humatro Pen®, Reco-Pen®, Roferon Pen®, Biojector®, Iject®, J-tip Needle-Free Injector®, Intraject®, Medi-Ject®, Smartject® e.g., as made or developed by Becton Dickensen (Franklin Lakes, N.J., www.bectondickenson.com), Disetronic (Burgdorf, Switzerland, www.disetronic.com; Bioject, Portland, Oreg. (www.bioject.com); National Medical Products, Weston Medical (Peterborough, UK, www.weston-medical.com), Medi-Ject Corp (Minneapolis, Minn., www.mediject.com), and similarly suitable devices. Recognized devices comprising a dual vial system include those pen-injector systems for reconstituting a lyophilized drug in a cartridge for delivery of the reconstituted solution, such as the HumatroPen®. Examples of other devices suitable include pre-filled syringes, auto-injectors, needle free injectors, and needle free IV infusion sets.

The products can include packaging material. The packaging material provides, in addition to the information required by the regulatory agencies, the conditions under which the product can be used. The packaging material of the present invention provides instructions to the subject, as applicable, to reconstitute the at least one anti-IL-12/IL-23p40 or IL-23 antibody in the aqueous diluent to form a solution and to use the solution over a period of 2-24 hours or greater for the two vial, wet/dry, product. For the single vial, solution product, pre-filled syringe or auto-injector, the label indicates that such solution can be used over a period of 2-24 hours or greater. The products are useful for human pharmaceutical product use.

The formulations used in the method of the present invention can be prepared by a process that comprises mixing an anti-IL-12/IL-23p40 and a selected buffer, preferably, a phosphate buffer containing saline or a chosen salt. Mixing the anti-IL-12/IL-23p40 antibody and buffer in an aqueous diluent is carried out using conventional dissolution and mixing procedures. To prepare a suitable formulation, for example, a measured amount of at least one antibody in water or buffer is combined with the desired buffering agent in water in quantities sufficient to provide the protein and buffer at the desired concentrations. Variations of this process would be recognized by one of ordinary skill in the art. For example, the order the components are added, whether additional additives are used, the temperature and pH at which the formulation is prepared, are all factors that can be optimized for the concentration and means of administration used.

The method of the invention provides pharmaceutical compositions comprising various formulations useful and acceptable for administration to a human or animal subject. Such pharmaceutical compositions are prepared using water at "standard state" as the diluent and routine methods well known to those of ordinary skill in the art. For example, buffering components such as histidine and histidine monohydrochloride hydrate, can be provided first followed by the addition of an appropriate, non-final volume of water diluent, sucrose and polysorbate 80 at "standard state."

Isolated antibody can then be added. Last, the volume of the pharmaceutical composition is adjusted to the desired final volume under "standard state" conditions using water as the diluent. Those skilled in the art will recognize a number of other methods suitable for the preparation of the pharmaceutical compositions.

The pharmaceutical compositions can be aqueous solutions or suspensions comprising the indicated mass of each constituent per unit of water volume or having an indicated pH at "standard state." As used herein, the term "standard state" means a temperature of 25° C.+/−2° C. and a pressure of 1 atmosphere. The term "standard state" is not used in the art to refer to a single art recognized set of temperatures or pressure, but is instead a reference state that specifies temperatures and pressure to be used to describe a solution or suspension with a particular composition under the reference "standard state" conditions. This is because the volume of a solution is, in part, a function of temperature and pressure. Those skilled in the art will recognize that pharmaceutical compositions equivalent to those disclosed here can be produced at other temperatures and pressures. Whether such pharmaceutical compositions are equivalent to those disclosed here should be determined under the "standard state" conditions defined above (e.g. 25° C.+/−2° C. and a pressure of 1 atmosphere).

Importantly, such pharmaceutical compositions can contain component masses "about" a certain value (e.g. "about 0.53 mg L-histidine") per unit volume of the pharmaceutical composition or have pH values about a certain value. A component mass present in a pharmaceutical composition or pH value is "about" a given numerical value if the isolated antibody present in the pharmaceutical composition is able to bind a peptide chain while the isolated antibody is present in the pharmaceutical composition or after the isolated antibody has been removed from the pharmaceutical composition (e.g., by dilution). Stated differently, a value, such as a component mass value or pH value, is "about" a given numerical value when the binding activity of the isolated antibody is maintained and detectable after placing the isolated antibody in the pharmaceutical composition.

Competition binding analysis is performed to determine if the IL-12/IL-23p40 or IL-23 specific mAbs bind to similar or different epitopes and/or compete with each other. Abs are individually coated on ELISA plates. Competing mAbs are added, followed by the addition of biotinylated hrIL-12 or IL-23. For positive control, the same mAb for coating can be used as the competing mAb ("self-competition"). IL-12/IL-23p40 or IL-23 binding is detected using streptavidin. These results demonstrate whether the mAbs recognize similar or partially overlapping epitopes on IL-12/IL-23p40 or IL-23.

In one embodiment of the pharmaceutical compositions, the isolated antibody concentration is from about 77 to about 104 mg per ml of the pharmaceutical composition. In another embodiment of the pharmaceutical compositions the pH is from about 5.5 to about 6.5.

The stable or preserved formulations can be provided to subjects as clear solutions or as dual vials comprising a vial of lyophilized at least one anti-IL-12/IL-23p40 that is reconstituted with a second vial containing a preservative or buffer and excipients in an aqueous diluent. Either a single solution vial or dual vial requiring reconstitution can be reused multiple times and can suffice for a single or multiple cycles of subject treatment and thus provides a more convenient treatment regimen than currently available.

Other formulations or methods of stabilizing the anti-IL-12/IL-23p40 can result in other than a clear solution of lyophilized powder comprising the antibody. Among non-clear solutions are formulations comprising particulate suspensions, said particulates being a composition containing the anti-IL-12/IL-23p40 in a structure of variable dimension and known variously as a microsphere, microparticle, nanoparticle, nanosphere, or liposome. Such relatively homogenous, essentially spherical, particulate formulations containing an active agent can be formed by contacting an aqueous phase containing the active agent and a polymer and a nonaqueous phase followed by evaporation of the nonaqueous phase to cause the coalescence of particles from the aqueous phase as taught in U.S. Pat. No. 4,589,330. Porous microparticles can be prepared using a first phase containing active agent and a polymer dispersed in a continuous solvent and removing said solvent from the suspension by freeze-drying or dilution-extraction-precipitation as taught in U.S. Pat. No. 4,818,542. Preferred polymers for such preparations are natural or synthetic copolymers or polymers selected from the group consisting of glelatin agar, starch, arabinogalactan, albumin, collagen, polyglycolic acid, polylactic aced, glycolide-L(−) lactide poly(episilon-caprolactone, poly(epsilon-caprolactone-CO-lactic acid), poly(epsilon-caprolactone-CO-glycolic acid), poly(B-hydroxy butyric acid), polyethylene oxide, polyethylene, poly (alkyl-2-cyanoacrylate), poly(hydroxyethyl methacrylate), polyamides, poly(amino acids), poly(2-hydroxyethyl DL-aspartamide), poly(ester urea), poly(L-phenylalanine/ethylene glycol/1,6-diisocyanatohexane) and poly(methyl methacrylate). Particularly preferred polymers are polyesters, such as polyglycolic acid, polylactic aced, glycolide-L(~) lactide poly(episilon-caprolactone, poly(epsilon-caprolactone-CO-lactic acid), and poly(epsilon-caprolactone-CO-glycolic acid. Solvents useful for dissolving the polymer and/or the active include: water, hexafluoroisopropanol, methylenechloride, tetrahydrofuran, hexane, benzene, or hexafluoroacetone sesquihydrate. The process of dispersing the active containing phase with a second phase can include pressure forcing said first phase through an orifice in a nozzle to affect droplet formation.

Dry powder formulations can result from processes other than lyophilization, such as by spray drying or solvent extraction by evaporation or by precipitation of a crystalline composition followed by one or more steps to remove aqueous or non-aqueous solvent. Preparation of a spray-dried antibody preparation is taught in U.S. Pat. No. 6,019,968. The antibody-based dry powder compositions can be produced by spray drying solutions or slurries of the antibody and, optionally, excipients, in a solvent under conditions to provide a respirable dry powder. Solvents can include polar compounds, such as water and ethanol, which can be readily dried. Antibody stability can be enhanced by performing the spray drying procedures in the absence of oxygen, such as under a nitrogen blanket or by using nitrogen as the drying gas. Another relatively dry formulation is a dispersion of a plurality of perforated microstructures dispersed in a suspension medium that typically comprises a hydrofluoroalkane propellant as taught in WO 9916419. The stabilized dispersions can be administered to the lung of a subject using a metered dose inhaler. Equipment useful in the commercial manufacture of spray dried medicaments are manufactured by Buchi Ltd. or Niro Corp.

An anti-IL-12/IL-23p40 in either the stable or preserved formulations or solutions described herein, can be administered to a subject in accordance with the present invention via a variety of delivery methods including SC or IM injection; transdermal, pulmonary, transmucosal, implant, osmotic pump, cartridge, micro pump, or other means appreciated by the skilled artisan, as well-known in the art.

Therapeutic Applications

The present invention also provides a method for modulating or treating ulcerative colitis, in a cell, tissue, organ, animal, or subject, as known in the art or as described herein, using at least one IL-23 antibody of the present invention, e.g., administering or contacting the cell, tissue, organ, animal, or subject with a therapeutic effective amount of IL-12/IL-23p40 or IL-23 specific antibody.

Any method of the present invention can comprise administering an effective amount of a composition or pharmaceutical composition comprising an IL-12/IL-23p40 to a cell, tissue, organ, animal or subject in need of such modulation, treatment or therapy. Such a method can optionally further comprise co-administration or combination therapy for treating such diseases or disorders, wherein the administering of said at least one IL-12/IL-23p40, specified portion or variant thereof, further comprises administering, before concurrently, and/or after, at least one selected from at least one TNF antagonist (e.g., but not limited to, a TNF chemical or protein antagonist, TNF monoclonal or polyclonal antibody or fragment, a soluble TNF receptor (e.g., p55, p70 or p85) or fragment, fusion polypeptides thereof, or a small molecule TNF antagonist, e.g., TNF binding protein I or II (TBP-1 or TBP-II), nerelimonmab, infliximab, eternacept (Enbrel™), adalimulab (Humira™), CDP-571, CDP-870, afelimomab, lenercept, and the like), an antirheumatic (e.g., methotrexate, auranofin, aurothioglucose, azathioprine, gold sodium thiomalate, hydroxychloroquine sulfate, leflunomide, sulfasalzine), a muscle relaxant, a narcotic, a non-steroid anti-inflammatory drug (NSAID) (e.g., 5-aminosalicylate), an analgesic, an anesthetic, a sedative, a local anesthetic, a neuromuscular blocker, an antimicrobial (e.g., aminoglycoside, an antifungal, an antiparasitic, an antiviral, a carbapenem, cephalosporin, a flurorquinolone, a macrolide, a penicillin, a sulfonamide, a tetracycline, another antimicrobial), an antipsoriatic, a corticosteriod, an anabolic steroid, a diabetes related agent, a mineral, a nutritional, a thyroid agent, a vitamin, a calcium related hormone, an antidiarrheal, an antitussive, an antiemetic, an antiulcer, a laxative, an anticoagulant, an erythropoietin (e.g., epoetin alpha), a filgrastim (e.g., G-CSF, Neupogen), a sargramostim (GM-CSF, Leukine), an immunization, an immunoglobulin, an immunosuppressive (e.g., basiliximab, cyclosporine, daclizumab), a growth hormone, a hormone replacement drug, an estrogen receptor modulator, a mydriatic, a cycloplegic, an alkylating agent, an antimetabolite, a mitotic inhibitor, a radiopharmaceutical, an antidepressant, antimanic agent, an antipsychotic, an anxiolytic, a hypnotic, a sympathomimetic, a stimulant, donepezil, tacrine, an asthma medication, a beta agonist, an inhaled steroid, a leukotriene inhibitor, a methylxanthine, a cromolyn, an epinephrine or analog, dornase alpha (Pulmozyme), a cytokine or a cytokine antagonist. Suitable dosages are well known in the art. See, e.g., Wells et al., eds., Pharmacotherapy Handbook, 2nd Edition, Appleton and Lange, Stamford, Conn. (2000); PDR Pharmacopoeia, Tarascon Pocket Pharmacopoeia 2000, Deluxe Edition, Tarascon Publishing, Loma Linda, Calif. (2000); Nursing 2001 Handbook of Drugs, 21st edition, Springhouse Corp., Springhouse, Pa., 2001; Health Professional's Drug Guide 2001, ed., Shannon, Wilson, Stang, Prentice-Hall, Inc, Upper Saddle River, N.J., each of which references are entirely incorporated herein by reference.

Therapeutic Treatments

Treatment of ulcerative colitis is affected by administering an effective amount or dosage of an anti-IL-12/23p40 composition in a subject in need thereof. The dosage administered can vary depending upon known factors, such as the pharmacodynamic characteristics of the particular agent, and its mode and route of administration; age, health, and weight of the recipient; nature and extent of symptoms, kind of concurrent treatment, frequency of treatment, and the effect desired. In some instances, to achieve the desired therapeutic amount, it can be necessary to provide for repeated administration, i.e., repeated individual administrations of a particular monitored or metered dose, where the individual administrations are repeated until the desired daily dose or effect is achieved.

In one exemplary regimen of providing safe and effective treatment of severely active UC in a subject in need thereof, a total dosage of about 130 mg of an anti-IL-12/IL-23p40 antibody is administered intravenously to the subject per administration. For example, the total volume of the composition administered is appropriately adjusted to provide to the subject the target dosage of the antibody at 80 mg, 90 mg, 100 mg, 110 mg, 120 mg, 130 mg, 140 mg, 150 mg, 160 mg, 170 mg or 180 mg per administration.

In another exemplary regimen of providing safe and effective treatment of severely active UC in a subject in need thereof, a total dosage of about 6.0 mg/kg 1.5 mg/kg of an anti-IL-12/IL-23p40 antibody is administered intravenously to the subject per administration. For example, the total volume of the composition administered is appropriately adjusted to provide to the subject the target dosage of the antibody at 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, or 9.0 mg/kg body weight of the subject per administration.

The total dosage of an anti-IL-12/IL-23p40 antibody to be administered to the subject per administration can be administered by intravenous infusion over a period of about 30 minutes to 180 minutes, preferably 60 minutes to 120 minutes, such as 30 minutes, 60 minutes, 90 minutes, 120 minutes, 150 minutes, or 180 minutes.

In yet another exemplary regimen of providing safe and effective treatment of severely active UC in a subject in need thereof, a total dosage of about 90 mg of an anti-IL-12/IL-23p40 antibody is administered subcutaneously to the subject per administration. For example, the total volume of the composition administered is appropriately adjusted to provide to the subject the target dosage of the antibody at 40 mg, 50 mg, 60 mg, 70 mg, 80 mg, 90 mg, 100 mg, 110 mg, 120 mg, 130 mg or 140 mg per administration. The target dosage per administration can be administered in a single subcutaneous injection or in multiple subcutaneous injections, such as 1, 2, 3, 4, 5, or more subcutaneous injections.

The total dosage of the anti-IL-12/IL-23p40 antibody can be administered once per day, once per week, once per month, once every six months, etc. for a period of one day, one week, one month, six months, 1 year, 2 years or longer. Multiple administrations of the anti-IL-12/IL-23p40 antibody, each at a total dosage of described herein, can be administered to a subject in need thereof.

Dosage forms (composition) suitable for internal administration generally contain from about 0.001 milligram to about 500 milligrams of active ingredient per unit or container.

For parenteral administration, the antibody can be formulated as a solution, suspension, emulsion, particle, powder, or lyophilized powder in association, or separately provided, with a pharmaceutically acceptable parenteral vehicle. Examples of such vehicles are water, saline, Ringer's solution, dextrose solution, and 1-10% human serum albumin. Liposomes and nonaqueous vehicles, such as fixed oils, can also be used. The vehicle or lyophilized powder can contain additives that maintain isotonicity (e.g., sodium chloride, mannitol) and chemical stability (e.g., buffers and preservatives). The formulation is sterilized by known or suitable techniques.

Suitable pharmaceutical carriers are described in the most recent edition of Remington's Pharmaceutical Sciences, A. Osol, a standard reference text in this field.

Many known and developed modes can be used according to the present invention for administering pharmaceutically effective amounts of an IL-12/IL-23p40 antibody. IL-12/IL-23p40 or IL-23 antibodies of the present invention can be delivered in a carrier, as a solution, emulsion, colloid, or suspension, or as a dry powder, using any of a variety of devices and methods suitable for administration by inhalation or other modes described here within or known in the art.

Formulations for parenteral administration can contain as common excipients sterile water or saline, polyalkylene glycols, such as polyethylene glycol, oils of vegetable origin, hydrogenated naphthalenes and the like. Aqueous or oily suspensions for injection can be prepared by using an appropriate emulsifier or humidifier and a suspending agent, according to known methods. Agents for injection can be a non-toxic, non-orally administrable diluting agent, such as aqueous solution, a sterile injectable solution or suspension in a solvent. As the usable vehicle or solvent, water, Ringer's solution, isotonic saline, etc. are allowed; as an ordinary solvent or suspending solvent, sterile involatile oil can be used. For these purposes, any kind of involatile oil and fatty acid can be used, including natural or synthetic or semisynthetic fatty oils or fatty acids; natural or synthetic or semi-synthtetic mono- or di- or tri-glycerides. Parental administration is known in the art and includes, but is not limited to, conventional means of injections, a gas pressured needleless injection device as described in U.S. Pat. No. 5,851,198, and a laser perforator device as described in U.S. Pat. No. 5,839,446 entirely incorporated herein by reference.

Alternative Delivery

The invention further relates to the administration of an anti-IL-12/IL-23p40 or IL-23 antibody by parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, intralesional, bolus, vaginal, rectal, buccal, sublingual, intranasal, or transdermal means. An anti-IL-12/IL-23p40 or IL-23 antibody composition can be prepared for use for parenteral (subcutaneous, intramuscular or intravenous) or any other administration particularly in the form of liquid solutions or suspensions; for use in vaginal or rectal administration particularly in semisolid forms, such as, but not limited to, creams and suppositories; for buccal, or sublingual administration, such as, but not limited to, in the form of tablets or capsules; or intranasally, such as, but not limited to, the form of powders, nasal drops or aerosols or certain agents; or transdermally, such as not limited to a gel, ointment, lotion, suspension or patch delivery system with chemical enhancers such as dimethyl sulfoxide to either modify the skin structure or to increase the drug concentration in the transdermal patch (Junginger, et al. In "Drug Permeation Enhancement;" Hsieh, D. S., Eds., pp. 59-90 (Marcel Dekker, Inc. New York 1994, entirely incorporated herein by reference), or with oxidizing agents that enable the application of formulations containing proteins and peptides onto the skin (WO 98/53847), or applications of electric fields to create transient transport pathways, such as electroporation, or to increase the mobility of charged drugs through the skin, such as iontophoresis, or application of ultrasound, such as sonophoresis (U.S. Pat. Nos. 4,309,989 and 4,767,402) (the above publications and patents being entirely incorporated herein by reference).

EMBODIMENTS

The invention provides also the following non-limiting embodiments.

1. A method of treating moderately to severely active ulcerative colitis (UC) in a subject in need thereof, comprising administering to the subject a pharmaceutical composition comprising a clinically proven safe and clinically proven effective amount of an anti-IL-12/IL-23p40 antibody, wherein the antibody comprises a heavy chain variable region and a light chain variable region, the heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and the light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6.
2. The method of embodiment 1, wherein the antibody comprises the heavy chain variable region of the amino acid sequence of SEQ ID NO:7 and the light chain variable region of the amino acid sequence of SEQ ID NO:8.
3. The method of embodiment 1, wherein the antibody comprises a heavy chain of the amino acid sequence of SEQ ID NO:10 and a light chain of the amino acid sequence of SEQ ID NO:11.
4. The method of any one of embodiments 1 to 3, wherein the antibody is administered intravenously to the subject, preferably at week 0 of the treatment, at a dosage of about 6.0 mg/kg body weight of the subject or 130 mg per administration.
5. The method of any one of embodiments 1 to 4, wherein the antibody is further administered subcutaneously to the subject, preferably at week 8 of the treatment, at a dosage of about 90 mg per administration.
6. The method of any one of embodiments 1 to 5, wherein the subject had previously failed or were intolerant of at least one therapy selected from the group consisting of an anti-TNF, vedolizumab, corticosteroids, azathioprine (AZA), and 6 mercaptopurine (6 MP), or the subject had demonstrated corticosteroid dependence.
7. The method of embodiment 5, wherein the antibody is administered in a maintenance dose every 8 weeks after the treatment at week 8 or every 12 weeks after the treatment at week 8.
8. The method of embodiment 7, wherein the subject is a responder to the treatment with the antibody and is identified as having a clinical remission based on at least one of the global definition and the US definition by week 16, preferably by week 8, more preferably by week 2, of the treatment and the clinical remission continues at least 44 weeks after week 0.

9. The method of embodiment 8, wherein the subject is in corticosteroid-free clinical remission at least 44 weeks after week 0.
10. The method of embodiment 7, wherein the subject is a responder to the treatment with the antibody and is identified as having an endoscopic healing continuing at least 44 weeks after week 0.
11. The method of embodiment 7, wherein the subject is a responder to the treatment with the antibody and is identified as achieving a clinical response based on the Mayo endoscopy subscore continuing at least 44 weeks after week 0.
12. The method of embodiment 7, wherein the subject is a responder to the treatment with the antibody and is identified as having a change from baseline in Inflammatory Bowel Disease Questionnaire (IBDQ) score continuing at least 44 weeks after week 0.
13. The method of embodiment 7, wherein the subject is a responder to the treatment with the antibody and is identified as having a mucosal healing continuing at least 44 weeks after week 0.
14. The method of embodiment 7, wherein the subject is a responder to the treatment with the antibody and is identified as having a decrease from baseline in Mayo score continuing at least 44 weeks after week 0.
15. The method of embodiment 7, wherein the subject is a responder to the treatment with the antibody and is identified as having a normalization of one or more biomarkers selected from the group consisting of C-reactive protein, fecal lactoferrin and fecal calprotectin continuing at least 44 weeks after week 0.
16. The method of embodiment 7, wherein the subject is in clinical response as determined by a decrease from baseline in the Mayo score by ≥30% and ≥3 points and a decrease from baseline in the rectal bleeding subscore ≥1 points or a rectal bleeding subscore of 0 or 1 continuing at least 44 weeks after week 0.
17. A method of treating moderately to severely active ulcerative colitis (UC) in a subject in need thereof, comprising:
    a. intravenously administering to the subject an anti-IL-12/IL-23p40 antibody in a first pharmaceutical composition at a dosage of about 6.0 mg/kg body weight of the subject or 130 mg per administration at week 0 of the treatment, and
    b. subcutaneously administering to the subject the anti-IL-12/IL-23p40 antibody in a second pharmaceutical composition at a dosage of 90 mg per administration, preferably at week 8 of the treatment, wherein the antibody comprises a heavy chain variable region and a light chain variable region, the heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and the light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6; and
    wherein the subject had previously failed or were intolerant of at least one therapy selected from the group consisting of: an anti-TNF, vedolizumab, corticosteroids, azathioprine (AZA), and 6 mercaptopurine (6 MP), or the subject had demonstrated corticosteroid dependence.
18. The method of embodiment 17, wherein the antibody comprises the heavy chain variable region of the amino acid sequence of SEQ ID NO:7 and the light chain variable region of the amino acid sequence of SEQ ID NO:8.
19. The method of embodiment 17, wherein the antibody comprises a heavy chain of the amino acid sequence of SEQ ID NO:10 and a light chain of the amino acid sequence of SEQ ID NO:11.
20. The method of any one of embodiments 1-19, wherein the pharmaceutical composition for intravenous administration further comprises a solution comprising 10 mM L-histidine, 8.5% (w/v) sucrose, 0.04% (w/v) polysorbate 80, 0.4 mg/mL L-methionine, and 20 µg/mL EDTA disodium salt, dehydrate, at pH 6.0.
21. The method of any one of embodiments 1-20, wherein the pharmaceutical composition for subcutaneous administration further comprises a solution comprising 6.7 mM L-histidine, 7.6% (w/v) sucrose, 0.004% (w/v) polysorbate 80, at pH 6.0.
22. The method of any one of embodiments 1-21, wherein the subject is a responder to the treatment with the antibody and is identified as having a clinical remission based on at least one of the global definition and the US definition by week 16, preferably by week 8, more preferably by week 2, of the treatment.
23. The method of any one of embodiments 1-22, wherein the subject is a responder to the treatment with the antibody and is identified as having an endoscopic healing by week 16, preferably by week 8, more preferably by week 2, of the treatment.
24. The method of any one of embodiments 1-23, wherein the subject is a responder to the treatment with the antibody and is identified as achieving a clinical response based on the Mayo endoscopy subscore by week 16, preferably by week 8, more preferably by week 2, of the treatment.
25. The method of any one of embodiments 1-24, wherein the subject is a responder to the treatment with the antibody and is identified as having a change from baseline in Inflammatory Bowel Disease Questionnaire (IBDQ) score by week 16, preferably by week 8, more preferably by week 2, of the treatment.
26. The method of any one of embodiments 1-25, wherein the subject is a responder to the treatment with the antibody and is identified as having a mucosal healing by week 16, preferably by week 8, more preferably by week 2, of the treatment.
27. The method of any one of embodiments 1-26, wherein the subject is a responder to the treatment with the antibody and is identified as having a decrease from baseline in Mayo score by week 16, preferably by week 8, more preferably by week 2, of the treatment.
28. The method of any one of embodiments 1-27, wherein the subject is a responder to the treatment with the antibody and is identified as having a normalization of one or more biomarkers selected from the group consisting of C-reactive protein, fecal lactoferrin and fecal calprotectin by week 16, preferably by week 8, more preferably by week 2, of the treatment.
29. The method of any one of embodiments 1-28, wherein the subject is in clinical response as determined by a decrease from baseline in the Mayo score by ≥30% and ≥3 points and a decrease from baseline in the rectal bleeding subscore ≥1 points or a rectal bleeding subscore of 0 or 1 by week 16, preferably by week 8, more preferably by week 2, of the treatment.
30. The method of any one of embodiments 17-21, wherein the subject is not a responder to the treatment with the antibody by week 8 and is a responder to the treatment by week 16 of the treatment.
31. A method of treating moderately to severely active ulcerative colitis (UC) in a subject in need thereof, comprising:
   a. intravenously administering to the subject an anti-IL-12/IL-23p40 antibody in a first pharmaceutical composition at a dosage of about 6.0 mg/kg body weight of the subject or 130 mg per administration at week 0 of the treatment, and
   b. subcutaneously administering to the subject the anti-IL-12/IL-23p40 antibody in a second pharmaceutical composition at a dosage of 90 mg per administration, preferably at week 8 of the treatment, wherein the antibody comprises a heavy chain variable region and a light chain variable region, the heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and the light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6 followed by a maintenance therapy
   wherein the maintenance therapy comprises subcutaneously administering to the subject the anti-IL-12/IL-23p40 antibody at a dosage of 90 mg per administration, once every 8 weeks or once every 12 weeks, and wherein the maintenance therapy is provided for 44 weeks.
32. A pharmaceutical composition of an anti-IL-12/IL-23p40 antibody, comprising an antibody and packaging comprising one or more drug product label elements disclosed in Annex I including data from a randomized, double-blind, placebo-controlled, clinical study in adult men and women with moderately to severely active ulcerative colitis (UC), wherein the antibody comprises: (i) a heavy chain variable region and a light chain variable region, the heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and the light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6; (ii) a heavy chain variable region of the amino acid sequence of SEQ ID NO:7 and a light chain variable region of the amino acid sequence of SEQ ID NO:8; or (iii) a heavy chain of the amino acid sequence of SEQ ID NO:10 and a light chain of the amino acid sequence of SEQ ID NO:11.
33. A method of selling a drug product comprising ustekinumab, comprising: manufacturing ustekinumab; promoting that a therapy comprising ustekinumab is safe and effective for treatment of a subject with ulcerative colitis, wherein performing the steps a) and b) results in a health care professional (HCP) to purchase the drug product; thereby selling the drug product.

Having generally described the invention, the same will be more readily understood by reference to the following Examples, which are provided by way of illustration and are not intended as limiting. Further details of the invention are illustrated by the following non-limiting Examples. The disclosures of all citations in the specification are expressly incorporated herein by reference.

EXAMPLES

Example 1: Induction Study of Ustekinumab in the Treatment of Ulcerative Colitis in Humans The following multicenter, randomized, double-blind, placebo-controlled, clinical study in adult men and women with moderately to severely active ulcerative colitis (UC) was performed: A Phase 3, Randomized, Double-blind, Placebo-controlled, Parallel-group, Multicenter Study to Evaluate the Safety and Efficacy of ustekinumab Induction and Maintenance Therapy in Subjects with Moderately to Severely Active Ulcerative Colitis Overall Rationale A study was performed to assess the efficacy of intravenous (IV) administration of ustekinumab in subjects with moderately to severely active ulcerative colitis who demonstrated inadequate response or failure to tolerate conventional (corticosteroids or 6-mercaptopurine/azathioprine [6-MP/AZA]) or biologic therapy (TNF antagonist and/or the integrin antagonist, vedolizumab). Subjects received a single 130 mg, a single 6 mg/kg IV dose, or placebo at Week 0. Subjects who demonstrated no clinical response at Week 8 received an additional IV or subcutaneous (SC) dose at Week 8.

Objectives

The primary objectives of the study included (1) evaluating the efficacy of ustekinumab in inducing clinical remission in subjects with moderately to severely active UC; and (2) evaluating the safety of the IV ustekinumab in subjects with moderately to severely active UC.

The secondary objectives of the study included (1) evaluating the efficacy of IV ustekinumab in inducing endoscopic healing (i.e. improvement in the endoscopic appearance of mucosa) in subjects with moderately to severely active UC; (2) evaluating the efficacy of IV ustekinumab in inducing clinical response in subjects with moderately to severely active UC; (3) evaluating the impact of IV ustekinumab on disease-specific health-related quality of life; (4) evaluating the efficacy of ustekinumab treatment on mucosal healing (i.e, endoscopic healing and histologic healing); (5) evaluating the efficacy of induction therapy with IV ustekinumab by biologic failure status; and (6) evaluating the pharmacokinetics (PK), immunogenicity, and pharmacodynamics (PD) of ustekinumab induction therapy in subjects with moderately to severely active UC, including changes in C-reactive protein (CRP), fecal calprotectin, fecal lactoferrin, and other PD biomarkers.

The exploratory objectives of the study included (1) evaluating response using the Mayo score without the physician's global assessment (PGA) subscore and (2) evaluating the performance of the Bristol Stool Form Scale (BSFS) score.

Experimental Design

The Phase 3 development program for ustekinumab comprised 2 separate studies, an induction study and a maintenance study. In the induction study, subjects were randomized at Week 0 into one of three treatment groups: placebo, low-dose ustekinumab, and high-dose ustekinumab. At Week 8, all subjects were evaluated for the primary endpoint of clinical remission and clinical response. Subjects who achieved a clinical response at Week 8 were eligible to enter the maintenance study. Subjects who did not achieve clinical response at Week 8 received a second dose of ustekinumab at Week 8 of treatment.

At Week 16, subjects who did not achieve clinical response at Week 8 were re-evaluated for clinical response. Subjects who achieved clinical response at Week 16 were eligible to enter the maintenance study. Subjects who did not achieve clinical response at Week 16 were not eligible to enter the maintenance study and had a safety follow-up visit approximately 20 weeks after their last dose of study agent (Week 8).

Subjects who were in clinical response to IV ustekinumab during induction comprised the primary population in the maintenance study. The maintenance study is a randomized withdrawal study designed to evaluate maintenance therapy using SC ustekinumab and is currently ongoing.

Dosage and Administration

Subjects received a single IV dose of ustekinumab or placebo at Week 0 of the study. The induction study antibodies with the administered doses are as follows:
  Ustekinumab at a low, fixed does of 130 mg
  Ustekinumab at a high, weight-range based dose of ~6 mg/kg:
    Ustekinumab 260 mg (body-weight≤55 kg)
    Ustekinumab 390 mg (body-weight>55 kg but ≤85 kg)
    Ustekinumab 520 mg (body-weight>85 kg)

Subjects who did not present a clinical response received a second dose of ustekinumab at Week 8. The study antibodies with the second administered doses are as follows:
  Subjects who were randomized to placebo at Week 0 received 1 dose of ustekinumab ~6 mg/kg IV+placebo SC (to maintain the blind) at Week 8.
  Subjects who were randomized to ustekinumab at Week 0 received 1 dose of ustekinumab 90 mg SC+placebo IV (to maintain the blind) at Week 8.

Safety Evaluations

Safety was evaluated based on AEs and clinical laboratory test results (i.e., hematology and serum chemistry). Adverse events were either voluntarily reported by the subject or were obtained by means of interviewing subjects in a non-directed manner at study visits. Safety evaluations included the following clinical laboratory tests:
  Hematology: Hemoglobin (Hb), hematocrit, red blood cell count, white blood cell (WBC) count, and platelets.
  Serum Chemistry: Sodium, potassium, chloride, blood urea nitrogen (BUN), creatinine, aspartate aminotransferase (AST), alanine aminotransferase (ALT), total and direct bilirubin, alkaline phosphatase, calcium, phosphate, albumin, total protein.
  Screening: Serology for human immunodeficiency virus antibody, serology for hepatitis C virus (HCV) antibody, serology for hepatitis B virus (HBV) antibody, hepatitis B surface antigen, HBV surface antibody (anti-HBs), and HBV core (anti-HBc) antibody total, QuantiFERON-TB Gold test, pregnancy (β human chorionic gonadotropin [(β-HCG]).

Pharmacokinetics

Blood samples for the measurement of serum ustekinumab concentrations were collected at Week 0 (pre- and postinfusion) and Weeks 2, 4, and 8. Analyses of serum ustekinumab concentrations were performed using a validated electrochemiluminescent immunoassay (ECLIA) method on the Meso Scale Discovery (MSD®) platform (Gaithersburg, Md., USA). The lowest quantifiable concentration in a sample for the ECLIA method using the MSD platform was 0.1688 µg/mL.

Immunogenicity

Antibodies to ustekinumab were evaluated using serum samples collected from all subjects. Analyses of antibodies to ustekinumab were performed using a validated, drug-tolerant, electrochemiluminescence immunoassay (ECLIA), in which ustekinumab was used to capture and detect induced immune responses to ustekinumab. Antibody titers were determined for all subjects who had antibodies to ustekinumab and the neutralizing antibody (Nab) status of anti-drug antibody positive samples were determined.

Efficacy Evaluation

Efficacy evaluations were collected throughout the study. Mayo score and partial Mayo score, Ulcerative Colitis Endoscopic Index of Severity (UCEIS), Bristol Stool Form Scale (BSFS), C-reactive protein (CRP), fecal lactoferrin, fecal calprotectin, Inflammatory Bowel Disease Questionnaire (IBDQ), 36-item Short Form Health Survey (SF-36), and EuroQoL-5D Health Questionnaire were all evaluated to determine efficacy. The efficacy criteria were defined as follows:
  Clinical remission (global submissions): Mayo score ≤2 points, with no individual subscore >1.
  Clinical remission (US submissions): absolute stool number ≤3, rectal bleeding subscore of 0, and Mayo endoscopy subscore of 0 or 1.
  Clinical response: a decrease from induction baseline in the Mayo score by ≥30% and ≥3 points, with either a decrease from baseline in the rectal bleeding subscore ≥1 or a rectal bleeding subscore of 0 or 1.
  Endoscopic healing (i.e., improvement in the endoscopic appearance of the mucosa): Mayo endoscopy subscore of 0 or 1.
  Histologic healing: based on the Geboes score and is defined as 0 to <5% neutrophils in epithelium and no crypt destruction, erosions, ulcerations, or granulations.
  Mucosal healing: both endoscopic healing and histologic healing.
  Normal or inactive mucosal disease: Mayo endoscopy subscore of 0.
  Symptomatic remission: Mayo stool frequency subscore of 0 or 1 and a rectal bleeding subscore of 0.
  Normalization of CRP concentration: CRP concentration ≤3 mg/L.
  Normalization of fecal lactoferrin concentration: fecal lactoferrin concentration ≤7.24 µg/g.
  Normalization of fecal calprotectin concentration: fecal calprotectin concentration ≤250 mg/kg.
  Modified Mayo score response:
    Definition 1: a decrease in the modified Mayo score of ≥2 points and ≥35% and either a decrease in the rectal bleeding subscore of ≥1 or a rectal bleeding subscore of 0 or 1.
    Definition 2: a decrease in the modified Mayo score of ≥2 points and ≥30% and either a decrease in rectal bleeding of ≥1 or a rectal bleeding score of 0 or 1.

Safety Results

Intravenous ustekinumab doses of both ~6 mg/kg and 130 mg were generally well-tolerated with a safety profile that was generally comparable with placebo through Week 8.0f the 960 subjects in the safety analysis set, 1 or more treatment-emergent AEs was reported through Week 8 for 50.0%, 41.4%, and 48.0% of subjects in the ~6 mg/kg, 130 mg, and placebo groups, respectively. Through Week 8, serious adverse effects (SAEs) were reported for 3.1%, 3.7%, and 6.6% of subjects in the ~6 mg/kg, 130 mg, and placebo groups, respectively.

AEs within 1 hour of infusion were 0.9%, 2.2%, and 1.9% in the ~6 mg/kg, 130 mg, and placebo groups, respectively.

The proportions of subjects with 1 or more infections were 15.3%, 15.9%, and 15.0% in the ~6 mg/kg, 130 mg, and placebo groups, respectively. Serious infections were reported for 0.3%, 0.6%, and 1.3% of subjects in the ~6 mg/kg, 130 mg, and placebo groups, respectively.

Pharmacokinetics Results

Serum samples were collected at Week 0 (preadministration), Week 0 (1 hr post-administration, Week 2, Week 4, and Week 8. For subjects randomized to ustekinumab treatment, a single IV infusion of ustekinumab was given either as a weight-based tiered dose of ~6 mg/kg (ie, 260 mg for subjects with body-weight≤55 kg, 390 mg for subjects with body-weight>55 kg and <85 kg, or 520 mg for subjects with body-weight>85 kg), or as a fixed dose of 130 mg. Considering that the median body-weight of subjects in the 130 mg group was 72 kg, the ustekinumab 130 mg dose corresponded to ~2 mg/kg on a per-kg basis. Thus, on average, ustekinumab exposure in the ~6 mg/kg group was approximately 3 times that of the 130 mg group. In line with this expectation, after a single IV administration of ustekinumab ~6 mg/kg or 130 mg, median serum ustekinumab concentrations were approximately dose proportional at all sampling timepoints through Week 8. Median peak serum ustekinumab concentrations, which were observed 1 hour after the end of the infusion at Week 0, were 127.0 μg/mL and 43.16 μg/mL for the ~6 mg/kg and 130 mg groups, respectively. At Week 8, the time of the primary efficacy endpoint, the median serum ustekinumab concentrations were 8.59 μg/mL and 2.51 μg/mL for the ~6 mg/kg and 130 mg groups, respectively.

Subjects who were not in clinical response at Week 8 following administration of placebo IV at Week 0 received ustekinumab ~6 mg/kg IV at Week 8, while subjects who were not in clinical response at Week 8 following administration of ustekinumab IV at Week 0 received ustekinumab 90 mg SC at Week 8. Among subjects who received placebo IV at Week 0 and who subsequently received ustekinumab ~6 mg/kg IV at Week 8, median serum ustekinumab concentration at Week 16 (8 weeks after the ustekinumab IV dose) was slightly higher than that observed at Week 8 (among subjects who received ustekinumab ~6 mg/kg IV at Week 0 [10.51 μg/mL versus 8.59 μg/mL, respectively]). Among subjects who received ustekinumab 90 mg SC at Week 8 (following their initial IV ustekinumab dose at Week 0), the median serum ustekinumab concentration at Week 16 was slightly higher in subjects who received ustekinumab ~6 mg/kg IV at Week 0 compared to those who received ustekinumab 130 mg at Week 0 (1.92 μg/mL versus 1.59 μg/mL, respectively)

Immunogenicity Results

Of the 635 subjects in the ustekinumab groups with appropriate samples for the assessment of antibodies to ustekinumab, 4 (0.6%) subjects were positive for antibodies to ustekinumab through Week 8. Of these 4 subjects, 2 (50%) were positive for NAbs.

Of 822 subjects who received ustekinumab at any time through Week 16, and had appropriate samples for the assessment of anti-drug antibodies (ADAs), 18 subjects (2.2%) were positive for antibodies to ustekinumab through the final safety visit. Of these, 4 of 15 subjects (26.7%) were positive for NAbs among those evaluable for NAbs through the final safety visit. Among subjects who received ustekinumab 90 mg SC at Week 8, the incidence of antibodies to ustekinumab through Week 16 was numerically higher in the 130 mg IV→90 mg SC group compared to the ~6 mg/kg IV→90 mg SC group (4.5% [6 of 132 subjects] vs 1.0% [1 of 101 subjects]).

Efficacy Results

Clinical Remission at Week 8-Global Definition

At Week 8, significantly greater proportions of subjects in the ~6 mg/kg and 130 mg groups achieved clinical remission (15.5% and 15.6%, respectively) compared with subjects in the placebo group (5.3%; p<0.001 for both comparisons; Table 1).

TABLE 1

Number of Subjects in Clinical Remission (Global Definition) at Week 8

| | Placebo | Ustekinumab IV | | |
|---|---|---|---|---|
| | IV | 130 mg | 6 mg/kg | Combined |
| Primary Efficacy Analysis Set Week 8 (N) | 319 | 320 | 322 | 642 |
| | 319 | 320 | 322 | 642 |
| Subjects in clinical remission | 17 (5.3%) | 50 (15.6%) | 50 (15.5%) | 100 (15.6%) |
| Adjusted Treatment difference | | 10.3 | 10.2 | 10.2 |
| (97.5% CI) | | (5.7, 14.9) | (5.6, 14.8) | (6.6, 13.9) |
| p-value | | <0.001 | <0.001 | <0.001 |

N = number of subjects;
CI = confidence interval

Clinical Remission at Week 8-US Definition

At Week 8, significantly greater proportions of subjects in the ~6 mg/kg and 130 mg groups achieved clinical remission (18.9% and 16.6%, respectively) compared with subjects in the placebo group (6.3%; p<0.001 for both comparisons; Table 2).

TABLE 2

Number of Subjects in Clinical Remission (US Definition) at Week 8

| | Placebo | Ustekinumab IV | | |
|---|---|---|---|---|
| | IV | 130 mg | 6 mg/kg | Combined |
| Primary Efficacy Analysis Set Week 8 (N) | 319 | 320 | 322 | 642 |
| | 319 | 320 | 322 | 642 |
| Subjects in clinical remission | 20 (6.3%) | 53 (16.6%) | 61 (18.9%) | 114 (17.8%) |
| Adjusted Treatment difference | | 10.3 | 12.7 | 11.5 |
| (97.5% CI) | | (4.8, 15.8) | (7.0, 18.4) | (7.0, 16) |
| p-value | | <0.001 | <0.001 | <0.001 |

N = number of subjects;
CI = confidence interval

Endoscopic Healing at Week 8

At Week 8, significantly greater proportions of subjects in the ~6 mg/kg and 130 mg groups achieved endoscopic healing (27.0% and 26.3%, respectively) compared with subjects in the placebo group (13.8%; p<0.001 for both comparisons; Table 3).

TABLE 3

Number of Subjects with Endoscopic Healing at Week 8

| | Placebo IV | Ustekinumab IV | | |
|---|---|---|---|---|
| | | 130 mg | 6 mg/kg | Combined |
| Primary Efficacy Analysis Set Week 8 (N) | 319 | 320 | 322 | 642 |
| | 319 | 320 | 322 | 642 |
| Subjects with endoscopic healing | 44 (13.8%) | 84 (26.3%) | 87 (27.0%) | 171 (26.6%) |
| Adjusted Treatment difference | | 12.4 | 13.3 | 12.8 |
| (95% CI) | | (6.5, 18.4) | (7.3, 19.3) | (7.9, 17.8) |
| (97.5% CI) | | (5.2, 19.2) | (6.4, 20.1) | (7.2, 18.5) |
| p-value | | <0.001 | <0.001 | <0.001 |

N = number of subjects;
CI = confidence interval

Clinical Response at Week 8

At Week 8, significantly greater proportions of subjects in the ~6 mg/kg and 130 mg groups achieved clinical response (61.8% and 51.3%, respectively) compared with subjects in the placebo group (31.3%; p<0.001 for both comparisons; Table 4).

TABLE 4

Number of Subjects in Clinical Response

| | Placebo IV | Ustekinumab IV | | |
|---|---|---|---|---|
| | | 130 mg | 6 mg/kg | Combined |
| Primary Efficacy Analysis Set Week 8 (N) | 319 | 320 | 322 | 642 |
| | 319 | 320 | 322 | 642 |
| Subjects in clinical response | 100 (31.3%) | 164 (51.3%) | 199 (61.8%) | 363 (56.5%) |
| Adjusted Treatment difference | | 19.9 | 30.5 | 25.2 |
| (95% CI) | | (12.8, 27.3) | (23.2, 37.8) | (18.9, 31.5) |
| (97.5% CI) | | (11.4, 28.3) | (22.2, 38.8) | (18.0, 32.4) |
| p-value | | <0.001 | <0.001 | <0.001 |

N = number of subjects;
CI = confidence interval

Change in Baseline in Total IBDQ Score at Week 8

At baseline, median IBDQ scores were similar across all treatment groups. At Week 8, the median improvements from baseline in the IBDQ scores were significantly greater in the ~6 mg/kg and 130 mg groups (31.0 and 31.5, respectively) compared with the placebo group (10.0; p<0.001 for both comparisons).

Clinical Remission at Week 8

When remission was assessed as clinical remission (global definition) with a rectal bleeding subscore of 0 at Week 8, the proportions of subjects who achieved this endpoint were almost identical to that observed based on the primary efficacy analysis (global definition). Significantly greater proportions of subjects in the ~6 mg/kg and 130 mg groups achieved this endpoint (15.2% and 15.3%, respectively) compared with subjects in the placebo group (5.3%; p<0.001 for both comparisons).

Symptomatic Remission at Week 8

At Week 8, significantly greater proportions of subjects in the ~6 mg/kg and 130 mg groups achieved symptomatic remission (44.7% and 41.3%, respectively) compared with subjects in the placebo group (22.6%; p<0.001 for both comparisons).

Histologic Healing at Week 8

Histologic healing was defined as 0 to <5% neutrophils in epithelium and no crypt destruction, erosions, ulcerations, or granulations. At Week 8, significantly greater proportions of subjects in the ~6 mg/kg and 130 mg groups achieved histologic healing (35.6% and 37.9%, respectively) compared with subjects in the placebo group (21.9%; p<0.001 for both comparisons).

Change from Baseline in Mayo Score at Week 8

At baseline, the mean Mayo scores were the same across all treatment groups (8.9 for all groups). At Week 8, the mean decreases from baseline in Mayo scores were significantly greater in the ~6 mg/kg and 130 mg groups (3.5 and 3.2, respectively) compared with the placebo group (1.8; p<0.001 for both comparisons).

Change from Baseline in Partial Mayo Score Through Week 8

At baseline, the mean partial Mayo scores were the same across all treatment groups (6.2 for all groups). As early as Week 2 and continuing for visits through Week 8, the mean decreases in the partial Mayo score were significantly greater in the ~6 mg/kg and 130 mg groups compared with the placebo group. At Week 2, the mean decreases from baseline in the partial Mayo scores were 1.6 and 1.5, in the ~6 mg/kg and 130 mg, respectively, compared with 1.0 in the placebo group (p<0.001 for both comparisons). At Week 8, the mean decreases from baseline in the partial Mayo scores were 2.9 and 2.6, in the ~6 mg/kg and 130 mg, respectively, compared with 1.5 in the placebo group (p<0.001 for both comparisons).

UCEIS Score at Week 8

The UCEIS score provides an overall assessment of endoscopic severity of UC, based on mucosal vascular pattern, bleeding, and ulceration. The score ranges from 3 to 11 with a higher score indicating more severe disease by endoscopy. The UCEIS score was assessed only during the central read of the video of the endoscopy.

At baseline, the mean UCEIS scores were similar across all treatment groups (7.6, 7.5, 7.5 in the ~6 mg/kg, 130 mg and placebo groups, respectively). At Week 8, the mean decreases from baseline in UCEIS scores were significantly greater in the ~6 mg/kg and 130 mg groups (1.3 and 1.1, respectively) compared with the placebo group (0.5; p<0.001 for both comparisons).

At Week 8, significantly greater proportions of subjects in the ~6 mg/kg and 130 mg groups had a UCEIS score of <4 (20.2% and 19.1%, respectively) compared with subjects in the placebo group (11.0%; p<0.001 and p=0.004, respectively). It is hypothesized that a UCEIS score of ≤4 is associated with Mayo endoscopic subscores of 0 or 1 that have defined endoscopic healing in this study.

Bristol Stool Form Scale Score

The BSFS score at a visit was the average of the 3-day daily average of the BSFS score prior to the visit. The same 3 days used to calculate the stool frequency and rectal bleeding subscores of the Mayo score were used to calculate the average BSFS score for the visit.

Approximately 40% (370/961) of randomized subjects had BSFS score collected at baseline. At baseline, 99.2% (367/370) of the subjects had average BSFS scores of ≥3 and the majority of subjects (54.3%) had average BSFS scores of ≥6, indicating diarrhea. As early as Week 2 and continuing for visits through Week 8, the proportions of subjects with diarrhea (average BSFS scores of ≥6) were smaller in the ~6 mg/kg and 130 mg groups compared with the placebo group. At Week 8, 22.8%, 21.1%, and 32.0% of subjects had diarrhea (average BSFS scores of ≥6) in the ~6 mg/kg, 130 mg and placebo groups, respectively. Furthermore, at Week 8 the proportion of subjects with normal stool (≥3 and <5) was greater in the ~6 mg/kg and 130 mg groups compared with placebo (48.3%, 48.9%, and 29.3%, respectively).

Normalization of C-Reactive Protein

C-reactive protein (CRP) is used as a marker of inflammation in subjects with IBD. In UC, elevated CRP has been associated with severe clinical activity, an elevated sedimentation rate, and active disease as detected by colonoscopy. C-reactive protein was assayed using a validated, high-sensitivity CRP assay.

At baseline, the proportion of subjects who had abnormal CRP (>3 mg/L) was similar across all treatment groups; overall, 59.2% of randomized subjects had abnormal CRP concentrations at baseline. As early as Week 2 and continuing for visits through Week 8, among subjects who had abnormal values at baseline, significantly greater proportions of subjects in the ~6 mg/kg and 130 mg groups achieved normalization of CRP (≤3 mg/L) compared with the placebo group. At Week 8, 38.7% and 34.1% of subjects achieved normalization of CRP in the ~6 mg/kg and 130 mg groups, respectively, compared with 21.1% of subjects in the placebo group (p<0.001 for both comparisons).

Normalization of Fecal Lactoferrin

At baseline, the proportions of subjects with abnormal fecal lactoferrin (>7.24 µg/g) were similar across all treatment groups; overall 90.0% of randomized subjects had abnormal fecal lactoferrin concentrations at baseline. At Week 4 and Week 8, among subjects who had abnormal values at baseline, significantly greater proportions of subjects in the ~6 mg/kg and 130 mg groups achieved normalization of fecal lactoferrin (≤7.24 µg/g) compared with the placebo group. At Week 8, 14.6% and 17.2% of subjects in the ~6 mg/kg and 130 mg groups, respectively, achieved normalization of fecal lactoferrin compared with 9.3% of subjects in the placebo group (p=0.042, p=0.006, respectively, for the ustekinumab groups).

Normalization of Fecal Calprotectin

At baseline, the proportions of subjects with abnormal fecal calprotectin (>250 mg/kg) were slightly greater in the ~6 mg/kg group (85.1%) compared with the placebo group (78.4%); 82.5% of subjects in the 130 mg group had abnormal fecal calprotectin at baseline. At Week 2 and Week 4, among subjects who had abnormal values at baseline, significantly greater proportions of subjects in the ~6 mg/kg and 130 mg groups achieved normalization of fecal calprotectin (≤250 mg/kg). At Week 8, among subjects with abnormal fecal calprotectin at baseline, the proportions of subjects with normalized fecal calprotectin, though not significant, were numerically greater in the ustekinumab ~6 mg/kg and 130 mg groups (25.5% and 24.2%, respectively), compared with subjects in the placebo group (20.4%; p=0.148, p=0.301 for both comparisons, respectively).

Example 2: Maintenance Study of Ustekinumab in the Treatment of Ulcerative Colitis in Humans Methodology In this randomized-withdrawal maintenance study, all subjects enrolled were to be responders to study agent administered in the induction study. Primary (randomized) population: Subjects who were in clinical response to IV ustekinumab following induction comprised the primary population in the maintenance study. This population included the following: subjects who were randomized to receive ustekinumab (ie, 130 mg IV or ~6 mg/kg IV) at Week 0 of the induction study and were in clinical response at induction Week 8; and subjects who were randomized to receive placebo at Week 0 of the induction study and were not in clinical response at induction Week 8 but were in clinical response at induction Week 16 after receiving a dose of IV ustekinumab (~6 mg/kg) at induction Week 8 (placebo→ustekinumab ~6 mg/kg IV). These subjects were randomized in a 1:1:1 ratio at maintenance Week 0 to receive ustekinumab 90 mg SC every 8 weeks (q8w), ustekinumab 90 mg SC every 12 weeks (q12w), or placebo SC. Nonrandomized population: Additional subjects entering the maintenance study were not randomized in the primary population and received maintenance treatment in this study as follows: ustekinumab induction delayed responders (ie, subjects who were not in clinical response to IV ustekinumab at induction Week 8 but were in clinical response at induction Week 16 after receiving ustekinumab 90 mg SC at induction Week 8) received ustekinumab 90 mg SC q8w; and placebo induction responders (ie, subjects who were in clinical response to placebo IV induction) received placebo SC. Nonrandomized subjects were followed for both efficacy and safety but were not included in the key efficacy analyses.

All subjects received their assigned dose of SC study agent at the maintenance Week 0 visit. Thereafter, to maintain the blind, all subjects received study agent at all scheduled study agent administration visits. Subjects were assessed for clinical flare at every visit and, if loss of clinical response was confirmed, were eligible for rescue medication. The main portion of the maintenance study was through Week 44 and a long-term study extension will continue through Week 220.

Number of Subjects (Planned and Analyzed):

783 subjects who completed the induction study and were in clinical response to induction study agent were enrolled in this maintenance study. The numbers of subjects in each treatment group at maintenance Week 0 were as follows:

Randomized (primary) population (523 subjects [327 subjects were planned]):
  176 subjects were randomized to ustekinumab 90 mg SC q8w.
  172 subjects were randomized to ustekinumab 90 mg SC q12w.
  175 subjects were randomized to placebo SC.
Nonrandomized population (260 subjects):
  157 subjects who were ustekinumab induction delayed responders (ie, were not in clinical response to ustekinumab at induction Week 8 but were in clinical response at induction Week 16) received ustekinumab 90 mg SC q8w.
  103 subjects who were in clinical response to placebo IV induction (placebo induction responders) received placebo SC.

Diagnosis and Main Criteria for Inclusion:

All subjects enrolled into this randomized-withdrawal maintenance study were those with moderately to severely active UC who had an inadequate response or had failed to tolerate conventional therapy (ie, corticosteroids or immunomodulators) or biologic therapy (ie, a TNF antagonist and/or vedolizumab), and demonstrated a clinical response to study agent during the induction study. This included subjects who were in clinical response to IV ustekinumab, in clinical response to IV placebo, or in delayed clinical response to ustekinumab, and had not received a protocol-prohibited medication change during the induction study.

Criteria for Evaluation:
Pharmacokinetics (PK): Serum ustekinumab concentration
Immunogenicity: Antibodies to ustekinumab
Pharmacodynamics (PD)/biomarkers: Serum biomarkers; fecal microbiome; RNA expression and histologic assessment of disease activity and healing in mucosal biopsies
Genetics and epigenetics: Whole blood deoxyribonucleic acid (DNA)
Efficacy: Mayo score and partial Mayo score, UC Endoscopic Index of Severity (UCEIS), CRP, fecal lactoferrin, and fecal calprotectin
Health-related Quality of Life: Inflammatory Bowel Disease Questionnaire (IBDQ), 36-item Short Form Health Survey (SF-36), EuroQoL-5D Health Questionnaire (EQ-5D)
Health economics: UC disease-related hospitalizations and surgeries; productivity Visual Analog Scale (VAS), and Work Productivity and Activity Impairment Questionnaire-General Health (WPAI-GH)
Safety: Adverse events (AEs), serious adverse events (SAEs), infections, injection site reactions, allergic reactions, hematology and chemistry parameters, vital signs, physical examinations, and early detection of tuberculosis Endpoints The primary endpoint was clinical remission at Week 44.
The definition of clinical remission (as well as the testing procedure) is different for submissions in the US and outside the US to accommodate the global and US preferred definitions of clinical remission. Each definition of clinical remission was applied to all subjects in the primary efficacy analysis set.
The global definition of the primary endpoint of clinical remission was defined as a Mayo score ≤2 points, with no individual subscore >1.
The US definition of clinical remission was defined as an absolute stool number ≤3, a Mayo rectal bleeding subscore of 0, and a Mayo endoscopy subscore of 0 or 1.
The major secondary endpoints, listed in the order in which they were tested, were:
Maintenance of clinical response through Week 44
Endoscopic healing at Week 44
Clinical remission and not receiving concomitant corticosteroids (corticosteroid-free clinical remission) at Week 44
Maintenance of clinical remission through Week 44 among the subjects who had achieved clinical remission at maintenance baseline
For the 3rd and 4th major secondary endpoints, the global definition of clinical remission was used to support submissions for countries outside the US and the US definition of clinical remission was used to support the submission in the United States.

Demographic and baseline disease characteristics were summarized based on the 961 subjects in the primary efficacy analysis set.

Analyses of multiplicity-controlled endpoints, except for the fourth major secondary endpoint related to maintenance of clinical remission, were conducted using a Cochran-Mantel-Haenszel (CMH) chi square test stratified by clinical remission (global definition) status at maintenance baseline (yes/no as determined by the IWRS) and induction treatment (placebo IV [I-0]→ustekinumab ~6 mg/kg IV [I-8], ustekinumab 130 mg IV [I-0], or ustekinumab ~6 mg/kg IV [I-0]). For the fourth major secondary endpoint (maintenance of clinical remission), a CMH chi-square test stratified by induction treatment was used.

Global and US-specific multiple testing procedures were prespecified to control the overall Type 1 error rate at the 0.05 level over the multiplicity-controlled endpoints in this study (Section 3.11.2.7.3). All statistical testing was performed at the 2-sided 0.05 significance level. Nominal p-values are presented.

Safety was assessed by summarizing the frequency and type of treatment-emergent adverse events (AEs), laboratory parameters (hematology and chemistry), and vital signs parameters. Safety summaries are provided separately for randomized subjects, nonrandomized subjects, and all treated subjects. Presentation of the safety data focuses on the randomized population.

Results:

Study Population

A total of 783 subjects who completed the induction study and were in clinical response to induction study agent were enrolled in this maintenance study. Of these, 523 subjects were in the targeted primary population for the maintenance study and were randomized to receive a SC administration of ustekinumab or placebo at maintenance Week 0 (176, 172, and 175 subjects in the ustekinumab 90 mg SC q8w, ustekinumab 90 mg SC q12w, and placebo groups, respectively). The remaining 250 subjects were in the nonrandomized population, including 157 ustekinumab induction delayed responders (who received ustekinumab 90 mg SC q8w) and 103 placebo induction responders (who received placebo). All enrolled subjects who were assigned treatment at maintenance baseline received their study agent at that time.

Prior to Week 40 (last dosing visit of the maintenance study), 85 subjects (16.3%) in the primary population discontinued study agent. The proportion of subjects who discontinued study agent was greater in the placebo group (24.6%) than those in the ustekinumab q8w and q12w groups (10.2% and 14.0%, respectively). The most common reasons for discontinuation were lack of efficacy and an adverse event due to worsening of UC. Prior to Week 44, 29 subjects (5.5%) in the primary population terminated study participation; the most common reason for termination of study participation was withdrawal of consent.

Baseline clinical disease characteristics were representative of a population of subjects with moderately to severely active UC that was refractory to available therapies and were generally well-balanced across the 3 treatment groups. The median duration of disease was 6.05 years and the median baseline Mayo score was 9.0, with 86.9% and 13.1% presenting with moderate and severe UC, respectively. At induction baseline, 52.2% of subjects in the primary population of the maintenance study were taking corticosteroids, 26.6% were taking immunomodulatory drugs, and 70.7% were taking aminosalicylates. The majority of subjects (93.5%) had an inadequate response to, or were intolerant of, corticosteroids and/or 6-MP/AZA, or demonstrated corticosteroid dependence at induction baseline. Overall in the primary population, 47.6% of subjects had a history of documented biologic failure and 52.4% of subjects did not. Also, 47.2% had failed at least 1 anti-TNF whereas 13.4% had failed both an anti-TNF and vedolizumab, and 49.3% were naïve to biologic therapy; 2 subjects were biologic failures to only vedolizumab.

Efficacy Results

Ustekinumab maintenance therapy demonstrated efficacy in a population of subjects with moderately to severely active UC who had previously failed or were intolerant of conventional or biologic therapies, including TNF antagonists and/or vedolizumab, and were in clinical response 8 weeks after receiving a single dose of ustekinumab IV induction therapy.

Based on the pre-specified global and US-specific multiple testing procedures, statistical significance can be claimed for both ustekinumab dose regimens (90 mg q8w and 90 mg q12w) for the primary endpoint of clinical remission at Week 44 and the three major secondary endpoints of maintenance of clinical response through Week 44, endoscopic healing at Week 44, and corticosteroid-free clinical remission at Week 44. Additionally, statistical significance can be claimed for maintenance of clinical remission through Week 44 (among the subjects who had achieved clinical remission at maintenance baseline) for both ustekinumab doses based on the US-specific testing procedure, and for the ustekinumab q12w regimen based on the global testing procedure.

Clinical Efficacy in the Primary Population (ie, Subjects in Clinical Response 8 Weeks After Receiving Ustekinumab IV Induction Therapy)

Primary Endpoint: Clinical Remission

The proportions of subjects in clinical remission (based on the global definition) at Week 44 were significantly greater in the ustekinumab q8w group and ustekinumab q12w group (43.8% and 38.4%, respectively) compared with subjects in the placebo group (24.0%; $p<0.001$ and $p=0.002$, respectively).

The proportions of subjects in clinical remission (based on the US-specific definition) at Week 44 were significantly greater in the ustekinumab q8w group and ustekinumab q12w group (42.6% and 39.5%, respectively) compared with subjects in the placebo group (24.6%; $p<0.001$ and $p=0.002$, respectively).

The effect of ustekinumab on achieving clinical remission (based on both the global and US specific definitions) was generally consistent across subgroups (including subjects who were biologic failures and those who were not biologic failures as well as subjects who were receiving concomitant immunomodulators or corticosteroids at induction baseline and those who were not) and was robust to prespecified changes in data-handling rules.

Major Secondary Endpoints: Maintenance of Clinical Response, Endoscopic Healing, Corticosteroid-Free Clinical Remission, and Maintenance of Clinical Remission The proportions of subjects who maintained clinical response through Week 44, achieved endoscopic healing, achieved corticosteroid-free remission (applying both global and US specific definitions of clinical remission) were significantly greater ($p<0.01$) in the ustekinumab q8w and q12w groups compared with that in the placebo group.

The proportions of subjects who maintained clinical remission among the subjects who had achieved clinical remission at maintenance baseline was numerically greater for both the ustekinumab q8w and q12w groups compared with that in the placebo group (applying both the global and US specific definition of clinical remission). Statistical significance ($p<0.01$) was achieved for both comparisons of the q8w and q12w groups versus placebo using the US-specific definition of clinical remission; however, statistical significance was only achieved for the q12w group ($p<0.01$) compared to placebo using the global definition of clinical remission.

Other Histologic, Mucosal, Clinical, and Endoscopic Endpoints

The analyses summarized below were not adjusted for multiplicity. Statements of statistical significance are based on nominal p-values.

The proportions of subjects who achieved histologic healing (ie, neutrophil infiltration in <5% of crypts, no crypt destruction, and no erosions, ulcerations, or granulation tissue) at Week 44 were significantly ($p<0.001$) greater in the ustekinumab q8w and q12w groups compared with the placebo group.

The proportions of subjects who achieved mucosal healing (a combination of endoscopic healing and histologic healing) at Week 44 were significantly ($p<0.01$) greater in the ustekinumab q8w and q12w groups compared with the placebo group.

Applying both global and US-specific definitions of clinical remission, the proportions of subjects achieving corticosteroid-free remission for at least 90 days prior to Week 44 was significantly greater ($p<0.01$) in the ustekinumab q8w and q12w groups compared with that in the placebo group. Furthermore, among subjects receiving corticosteroids at maintenance baseline, significantly greater proportions of subjects ($p<0.05$) were in clinical remission and not receiving concomitant corticosteroids for at least 90 days prior to Week 44 in the ustekinumab q8w and q12w groups compared with those in the placebo group.

The efficacy of ustekinumab maintenance treatment was also demonstrated in clinical outcomes as measured by maintained improvement in the partial Mayo score, maintenance of symptomatic remission as well as maintenance of endoscopic healing. Further evidence of the efficacy of ustekinumab maintenance treatment was observed in partial Mayo remission and symptomatic remission over time as well as symptom control (stool frequency and rectal bleeding).

Inflammatory Biomarkers

Over time through Week 44, the ustekinumab treatment groups maintained their CRP, fecal lactoferrin, and fecal calprotectin concentration levels observed at maintenance baseline, whereas median CRP, fecal lactoferrin, and fecal calprotectin concentrations worsened (increased) in the placebo group.

At Week 44, the proportion of subjects with normalized CRP, fecal calprotectin and fecal lactoferrin were generally significantly greater in the ustekinumab q8w and q12w groups compared with the placebo group.

Clinical Endpoints by Biologic Failure Status

For subjects with and subjects without a history of biologic failure, the proportions of subjects who achieved each of the primary and major secondary endpoints and mucosal healing were generally greater in the ustekinumab q8w and q12w groups compared with subjects in the placebo group.

In some cases, where treatment effects were similar in the biologic non-failure and failure populations, there was a consistent trend in the biologic-failure subjects across endpoints that the treatment effect for the ustekinumab q8w group was greater than that for the ustekinumab q12w group. This trend was not observed in the biologic non-failure population.

Efficacy Based on Inflammatory Biomarker Subgroups
  Among subjects with a higher inflammatory burden (elevated CRP and/or elevated fecal inflammatory markers) at either induction or maintenance baseline, while both dosages generally demonstrated efficacy compared to placebo, the efficacy of ustekinumab q8w seemed to be better across the range of clinical endpoints than the ustekinumab q12w group. However, in subjects with low inflammatory burden at baseline, the ustekinumab q8w and q12w groups demonstrated similar efficacy over the endpoints.

Health-Related Quality of Life
  Through Week 44, subjects in the ustekinumab q8w and q12w groups were generally able to maintain improvement in health-related quality of life as assessed using the IBDQ, SF 36 and EQ 5D instruments compared to subjects in the placebo group.

Outcomes for the Ustekinumab 90 mg q8w Dose and Ustekinumab 90 mg q12w Dose
  While both the ustekinumab q8w and q12w groups demonstrated generally similar efficacy for the primary and major secondary endpoints, q8w was modestly better than q12w based on the following more objective and stringent measures of efficacy, including:
    Endoscopic and mucosal healing at Week 44
    Durable partial Mayo remission at Week 44
    Corticosteroid-free clinical remission as well as the elimination of corticosteroids for at least 90 days prior to Week 44 among subjects receiving corticosteroids at maintenance baseline
  Furthermore, when efficacy was examined over time (for the following endpoints), the q8w group showed greater efficacy than the q12w group:
    Mayo stool frequency and rectal bleeding subscores indicating inactive or mild disease (ie, subscores of 0 or 1), as well as an absolute stool number ≤3 over time through Week 44.
    Partial Mayo remission and symptomatic remission over time through Week 44
    Median changes from baseline in fecal lactoferrin and calprotectin concentrations over time through Week 44.

Efficacy in Ustekinumab Induction Delayed Responders
Subjects who were delayed responders to ustekinumab induction therapy were able to maintain clinical response and achieve clinical remission, endoscopic, histologic, and mucosal healing (a combination of endoscopic healing and histologic healing) while receiving ustekinumab 90 mg q8w.

Efficacy and Pharmacokinetics/Immunogenicity
  In general, during maintenance, a positive association was observed between serum ustekinumab concentration and the clinical efficacy outcomes of clinical remission and endoscopic healing. In addition, lower levels of inflammation, as measured by CRP, were observed in subjects with higher serum ustekinumab concentrations.
  Among subjects receiving maintenance ustekinumab, the development of antibodies to ustekinumab did not appear to have an impact on clinical efficacy as measured by multiple endpoints such as clinical remission, endoscopic healing, clinical response, and change from maintenance baseline in Mayo score; however, the interpretation of the data is limited by the small sample size.

Pharmacokinetic and Immunogenicity Results
  Following maintenance treatment with ustekinumab 90 mg SC q8w or q12w, steady-state was reached at approximately 8 or 12 weeks after subjects began receiving ustekinumab 90 mg SC q8w, or ustekinumab 90 mg SC q12w maintenance dose regimens, respectively. Median steady state trough serum ustekinumab concentrations over time were approximately 3-fold greater the concentrations in the ustekinumab q8w group (2.69 μg/mL to 3.09 μg/mL) than in the q12w group (0.92 μg/mL to 1.19 μg/mL).
  Following maintenance dose regimens of ustekinumab 90 mg SC q8w or q12w, serum ustekinumab concentrations were sustained through Week 44 in almost all subjects, with a smaller proportion of subjects with undetectable trough concentrations over time in the 90 mg q8w group (0.7% to 2.4%) compared to those in the 90 mg q12w group (4.9% to 7.1%). The median ustekinumab concentration in subjects in the placebo group was below detectable levels by Week 16.
  The impact of the different ustekinumab IV induction doses on serum ustekinumab concentrations during maintenance continued to diminish over time, as expected.
  Median trough serum ustekinumab concentrations tended to be lower in subjects with higher body weight.
  Nonrandomized subjects in the ustekinumab induction delayed responders group tended to have lower serum ustekinumab concentrations over time compared to randomized subjects in the ustekinumab q8w group following SC administration of the same ustekinumab dose regimen of 90 mg q8w.
  Among 680 treated subjects with appropriate samples for the assessment of antibodies to ustekinumab, 39 (5.7%) were positive for antibodies to ustekinumab through 52 weeks of treatment, the majority with antibody titers ≤1:800. Of the 39 treated subjects who were positive for antibodies to ustekinumab in this maintenance study, 11 (28.2%) were positive for neutralizing antibodies.
  In all randomized treatment groups, median serum ustekinumab concentrations were lower over time in subjects who were positive for antibodies to ustekinumab compared with levels in subjects who were negative for antibodies to ustekinumab.

Safety Results
Subcutaneous maintenance regimens of ustekinumab 90 mg administered q12w or q8w through Week 44 were generally well tolerated and consistent with the known safety profile of ustekinumab.
  AEs were reported in 77.3%, 69.2%, and 78.9% of subjects in the ustekinumab q8w, ustekinumab q12w, and placebo groups, respectively.
    Reasonably related AEs were reported in 26.1%, 17.4%, and 28.6% of subjects in the ustekinumab q8w, ustekinumab q12w, and placebo groups, respectively.

Infections (as identified by the investigator) were reported in 48.9%, 33.7%, and 46.3% of subjects in the ustekinumab q8w, ustekinumab q12w, and placebo groups, respectively.

Infections requiring oral or parenteral antibiotic treatment were reported in 22.7%, 15.7%, and 19.4% of subjects in the ustekinumab q8w, ustekinumab q12w, and placebo groups, respectively.

Serious infections were infrequent among randomized subjects and were reported in 1.7%, 3.5%, and 2.3% in the ustekinumab q8w, ustekinumab q12w, and placebo groups, respectively. Opportunistic infections were identified in 3 subjects (all in the randomized population); cytomegalovirus colitis was diagnosed for 2 subjects in the ustekinumab q12w group and 1 subject was diagnosed with concurrent moderate AEs of ophthalmic and labial herpes. No cases of active TB were reported among ustekinumab-treated subjects through Week 44.

The proportion of randomized subjects with AEs leading to discontinuation of study agent was higher in the placebo group than in the q12w and q8w groups and the most frequent AEs leading to discontinuation in the placebo group was worsening UC.

Among all treated subjects, including delayed ustekinumab induction responders, the overall safety profile was consistent with that observed in the randomized population.

There was 1 death reported for a subject who was a delayed ustekinumab induction responder and was receiving ustekinumab q8w. The cause of death was attributed to acute respiratory failure that occurred during thyroid surgery for a multinodular goiter.

Among all treated subjects, 2 subjects (1 subject in the ustekinumab induction delayed-responders group [receiving ustekinumab q8w] and 1 subject randomized to the placebo group who had received ustekinumab IV during induction) reported serious major adverse cardiovascular events; both events were associated with perioperative complications.

Among all treated subjects, there were 6 subjects for whom malignancies were reported (5 ustekinumab-treated subjects and 1 placebo-only subject).

Three ustekinumab-treated subjects reported non-melanoma skin cancers (NMSCs); all had either a prior history of azathioprine or 6-MP treatment and 2 were on concomitant immunomodulator therapy at the time of the diagnosis.

Two ustekinumab-treated subjects were reported to have solid tumors; one subject with a papillary renal cell carcinoma (q12w) and one subject with colon cancer (q8w); both tumors were detected early during the subject's participation in this maintenance study.

There were no cases of anaphylaxis or delayed hypersensitivity reactions identified among ustekinumab treated subjects.

There were no notable differences in the proportions of subjects with post-baseline maximum toxicity Grade ≥1 chemistry and hematology laboratory between the placebo and respective ustekinumab groups. Grade 3 and Grade 4 chemistry and hematology laboratory values were infrequent.

Health Economics and Medical Resource Utilization Results

Through Week 44, fewer subjects in the combined ustekinumab group had a UC disease-related hospitalization or surgery compared with the placebo group.

At Week 44, change from maintenance baseline in productivity visual analog scores (VAS) demonstrated improvement in subjects in the ustekinumab treatment groups and worsening in subjects in the placebo group.

At Week 44, percentages within each of the 4 WPAI-GH domains were maintained from maintenance baseline for the ustekinumab treatment groups, with additional improvement observed in subjects in the ustekinumab q8w group for percent impairment while working due to health, percent overall work impairment due to health, and percent activity impairment due to health. For subjects in the placebo group, percentages for all 4 WPAI-GH domains worsened (ie, increased).

Conclusions

The ustekinumab maintenance study provided consistent and definitive evidence that the ustekinumab 90 mg SC q12w and q8w dose regimens were both effective in adult subjects with moderately to severely active UC who had responded to a single IV ustekinumab induction dose.

The efficacy of ustekinumab was observed in subjects who were biologic failures as well as those who failed conventional but not biologic therapy (ie, biology-naïve).

Of note, while both doses of ustekinumab were effective, the q8w dose regimen demonstrated modestly better efficacy across several objective and/or more stringent endpoints (eg, endoscopic healing and durable partial Mayo remission) as well as in over-time analyses of symptomatic and partial Mayo remission.

Maintenance dosing with ustekinumab SC dose regimens of 90 mg q12w and 90 mg q8w was generally well-tolerated over 44 weeks in this population of adult subjects with moderate to severe ulcerative colitis.

The safety and efficacy data from this study support a positive benefit/risk profile for ustekinumab SC maintenance therapy.

The European Commission has approved STELARA® (ustekinumab) for the treatment of ulcerative colitis (UC) in Europe as of Sep. 4, 2019. The approved label is shown in Annex I below describing the intravenous preparation (Sections 1-10) and subcutaneous preparation (Sections 1-10).

The present invention comprises a pharmaceutical composition of an anti-IL-12/IL-23p40 antibody and packaging comprising one or more label elements disclosed in Annex I, wherein the antibody comprises: (i) a heavy chain variable region and a light chain variable region, the heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and the light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6; (ii) a heavy chain variable region of the amino acid sequence of SEQ ID NO:7 and a light chain variable region of the amino acid sequence of SEQ ID NO:8; or (iii) a heavy chain of the amino acid sequence of SEQ ID NO:10 and a light chain of the amino acid sequence of SEQ ID NO:11.

Annex I

Summary of Product Characteristics

1. Name of the Medicinal Product

STELARA 130 mg concentrate for solution for infusion

2. Qualitative and Quantitative Composition

Each vial contains 130 mg ustekinumab in 26 mL (5 mg/mL).

Ustekinumab is a fully human IgG1K monoclonal antibody to interleukin (IL)-12/23 produced in a murine myeloma cell line using recombinant DNA technology.

For the full list of excipients, see section 6.1.

3. Pharmaceutical Form

Concentrate for solution for infusion.

The solution is clear, colourless to light yellow.

4. Clinical Particulars 4.1 Therapeutic Indications

Crohn's Disease

STELARA is indicated for the treatment of adult patients with moderately to severely active Crohn's disease who have had an inadequate response with, lost response to, or were intolerant to either conventional therapy or a TNFα antagonist or have medical contraindications to such therapies.

Ulcerative Colitis

STELARA is indicated for the treatment of adult patients with moderately to severely active ulcerative colitis who have had an inadequate response with, lost response to, or were intolerant to either conventional therapy or a biologic or have medical contraindications to such therapies (see section 5.1).

4.2 Posology and Method of Administration

STELARA concentrate for solution for infusion is intended for use under the guidance and supervision of physicians experienced in the diagnosis and treatment of Crohn's disease or ulcerative colitis. STELARA concentrate for solution for infusion should only be used for the intravenous induction dose.

Posology

Crohn's Disease and Ulcerative Colitis

STELARA treatment is to be initiated with a single intravenous dose based on body weight. The infusion solution is to be composed of the number of vials of STELARA 130 mg as specified in Label Table 1 (see section 6.6 for preparation).

LABEL TABLE 1

Initial intravenous dosing of STELARA

| Body weight of patient at the time of dosing | Recommended dose[a] | Number of 130 mg STELARA Vials |
|---|---|---|
| ≤55 kg | 260 mg | 2 |
| >55 kg to ≤85 kg | 390 mg | 3 |
| >85 kg | 520 mg | 4 |

[a]Approximately 6 mg/kg

The first subcutaneous dose should be given at week 8 following the intravenous dose. For the posology of the subsequent subcutaneous dosing regimen, see section 4.2 of the STELARA solution for injection (vial) and solution for injection in pre-filled syringe SmPC.

Elderly (≥65 Years)

No dose adjustment is needed for elderly patients (see section 4.4).

Renal and Hepatic Impairment

STELARA has not been studied in these patient populations. No dose recommendations can be made.

Paediatric Population

The safety and efficacy of STELARA for the treatment of Crohn's disease or ulcerative colitis in children less than 18 years have not yet been established. No data are available.

Method of Administration

STELARA 130 mg is for intravenous use only. It should be administered over at least one hour. For instructions on dilution of the medicinal product before administration, see section 6.6.

4.3 Contraindications

Hypersensitivity to the active substance or to any of the excipients listed in section 6.1.

Clinically important, active infection (e.g. active tuberculosis; see section 4.4).

4.4 Special Warnings and Precautions for Use

Traceability

In order to improve the traceability of biological medicinal products, the tradename and the batch number of the administered product should be clearly recorded.

Infections

Ustekinumab may have the potential to increase the risk of infections and reactivate latent infections. In clinical studies, serious bacterial, fungal, and viral infections have been observed in patients receiving STELARA (see section 4.8).

Caution should be exercised when considering the use of STELARA in patients with a chronic infection or a history of recurrent infection (see section 4.3).

Prior to initiating treatment with STELARA, patients should be evaluated for tuberculosis infection. STELARA must not be given to patients with active tuberculosis (see section 4.3). Treatment of latent tuberculosis infection should be initiated prior to administering STELARA. Anti-tuberculosis therapy should also be considered prior to initiation of STELARA in patients with a history of latent or active tuberculosis in whom an adequate course of treatment cannot be confirmed. Patients receiving STELARA should be monitored closely for signs and symptoms of active tuberculosis during and after treatment.

Patients should be instructed to seek medical advice if signs or symptoms suggestive of an infection occur. If a patient develops a serious infection, the patient should be closely monitored and STELARA should not be administered until the infection resolves.

Malignancies

Immunosuppressants like ustekinumab have the potential to increase the risk of malignancy. Some patients who received STELARA in clinical studies developed cutaneous and non-cutaneous malignancies (see section 4.8).

No studies have been conducted that include patients with a history of malignancy or that continue treatment in patients who develop malignancy while receiving STELARA. Thus, caution should be exercised when considering the use of STELARA in these patients.

All patients, in particular those greater than 60 years of age, patients with a medical history of prolonged immunosuppressant therapy or those with a history of PUVA treatment, should be monitored for the appearance of non-melanoma skin cancer (see section 4.8).

Systemic and Respiratory Hypersensitivity Reactions

Systemic

Serious hypersensitivity reactions have been reported in the postmarketing setting, in some cases several days after treatment. Anaphylaxis and angioedema have occurred. If an anaphylactic or other serious hypersensitivity reaction occurs, appropriate therapy should be instituted and administration of STELARA should be discontinued (see section 4.8).

Respiratory

Cases of allergic alveolitis and eosinophilic pneumonia have been reported during post-approval use of ustekinumab. Clinical presentations included cough, dyspnoea, and interstitial infiltrates following one to three doses. Serious outcomes have included respiratory failure and prolonged hospitalisation. Improvement has been reported after discontinuation of ustekinumab and also, in some cases, administration of corticosteroids. If infection has been excluded and diagnosis is confirmed, discontinue ustekinumab and institute appropriate treatment (see section 4.8).

Vaccinations

It is recommended that live viral or live bacterial vaccines (such as *Bacillus* of Calmette and Guérin (BCG)) should not be given concurrently with STELARA. Specific studies have not been conducted in patients who had recently received live viral or live bacterial vaccines. No data are available on the secondary transmission of infection by live vaccines in patients receiving STELARA. Before live viral or live bacterial vaccination, treatment with STELARA should be withheld for at least 15 weeks after the last dose and can be resumed at least 2 weeks after vaccination. Prescribers should consult the Summary of Product Characteristics for the specific vaccine for additional information and guidance on concomitant use of immunosuppressive agents post-vaccination.

Patients receiving STELARA may receive concurrent inactivated or non-live vaccinations.

Long term treatment with STELARA does not suppress the humoral immune response to pneumococcal polysaccharide or tetanus vaccines (see section 5.1).

Concomitant Immunosuppressive Therapy

In psoriasis studies, the safety and efficacy of STELARA in combination with immunosuppressants, including biologics, or phototherapy have not been evaluated. In psoriatic arthritis studies, concomitant MTX use did not appear to influence the safety or efficacy of STELARA. In Crohn's disease and ulcerative colitis studies, concomitant use of immunosuppressants or corticosteroids did not appear to influence the safety or efficacy of STELARA. Caution should be exercised when considering concomitant use of other immunosuppressants and STELARA or when transitioning from other immunosuppressive biologics (see section 4.5).

Immunotherapy

STELARA has not been evaluated in patients who have undergone allergy immunotherapy. It is not known whether STELARA may affect allergy immunotherapy.

Serious Skin Conditions

In patients with psoriasis, exfoliative dermatitis has been reported following ustekinumab treatment (see section 4.8). Patients with plaque psoriasis may develop erythrodermic psoriasis, with symptoms that may be clinically indistinguishable from exfoliative dermatitis, as part of the natural course of their disease. As part of the monitoring of the patient's psoriasis, physicians should be alert for symptoms of erythrodermic psoriasis or exfoliative dermatitis. If these symptoms occur, appropriate therapy should be instituted. STELARA should be discontinued if a drug reaction is suspected.

Special Populations

Elderly ($\geq$65 Years)

No overall differences in efficacy or safety in patients age 65 and older who received STELARA were observed compared to younger patients in clinical studies in approved indications, however the number of patients aged 65 and older is not sufficient to determine whether they respond differently from younger patients. Because there is a higher incidence of infections in the elderly population in general, caution should be used in treating the elderly.

Sodium Content

STELARA contains less than 1 mmol sodium (23 mg) per dose, i.e. essentially 'sodium-free'. STELARA is however, diluted in sodium chloride 9 mg/ml (0.9%) solution for infusion. This should be taken into consideration for patients on a controlled sodium diet (see section 6.6).

4.5 Interaction with Other Medicinal Products and Other Forms of Interaction

Live vaccines should not be given concurrently with STELARA (see section 4.4).

No interaction studies have been performed in humans. In the population pharmacokinetic analyses of the phase III studies, the effect of the most frequently used concomitant medicinal products in patients with psoriasis (including paracetamol, ibuprofen, acetylsalicylic acid, metformin, atorvastatin, levothyroxine) on pharmacokinetics of ustekinumab was explored. There were no indications of an interaction with these concomitantly administered medicinal products. The basis for this analysis was that at least 100 patients (>5% of the studied population) were treated concomitantly with these medicinal products for at least 90% of the study period. The pharmacokinetics of ustekinumab was not impacted by concomitant use of MTX, NSAIDs, 6-mercaptopurine, azathioprine and oral corticosteroids in patients with psoriatic arthritis, Crohn's disease or ulcerative colitis, or prior exposure to anti-TNFα agents, in patients with psoriatic arthritis or Crohn's disease or by prior exposure to biologics (i.e. anti-TNFα agents and/or vedolizumab) in patients with ulcerative colitis.

The results of an in vitro study do not suggest the need for dose adjustments in patients who are receiving concomitant CYP450 substrates (see section 5.2).

In psoriasis studies, the safety and efficacy of STELARA in combination with immunosuppressants, including biologics, or phototherapy have not been evaluated. In psoriatic arthritis studies, concomitant MTX use did not appear to influence the safety or efficacy of STELARA. In Crohn's disease and ulcerative colitis studies, concomitant use of immunosuppressants or corticosteroids did not appear to influence the safety or efficacy of STELARA. (see section 4.4).

4.6 Fertility, Pregnancy and Lactation

Women of Childbearing Potential

Women of childbearing potential should use effective methods of contraception during treatment and for at least 15 weeks after treatment.

Pregnancy

There are no adequate data from the use of ustekinumab in pregnant women. Animal studies do not indicate direct or indirect harmful effects with respect to pregnancy, embryonic/foetal development, parturition or postnatal development (see section 5.3). As a precautionary measure, it is preferable to avoid the use of STELARA in pregnancy.

Breast-Feeding

It is unknown whether ustekinumab is excreted in human breast milk. Animal studies have shown excretion of ustekinumab at low levels in breast milk. It is not known if ustekinumab is absorbed systemically after ingestion. Because of the potential for adverse reactions in nursing infants from ustekinumab, a decision on whether to discontinue breast-feeding during treatment and up to 15 weeks after treatment or to discontinue therapy with STELARA must be made taking into account the benefit of breast-feeding to the child and the benefit of STELARA therapy to the woman.

Fertility

The effect of ustekinumab on human fertility has not been evaluated (see section 5.3).

4.7 Effects on Ability to Drive and Use Machines

STELARA has no or negligible influence on the ability to drive and use machines.

4.8 Undesirable Effects

Summary of the Safety Profile

The most common adverse reactions (>5%) in controlled periods of the adult psoriasis, psoriatic arthritis, Crohn's disease and ulcerative colitis clinical studies with ustekinumab were nasopharyngitis and headache. Most were considered to be mild and did not necessitate discontinuation of study treatment. The most serious adverse reaction that has been reported for STELARA is serious hypersensitivity reactions including anaphylaxis (see section 4.4). The overall safety profile was similar for patients with psoriasis, psoriatic arthritis, Crohn's disease and ulcerative colitis.

Tabulated List of Adverse Reactions

The safety data described below reflect exposure in adults to ustekinumab in 14 phase 2 and phase 3 studies in 6,709 patients (4,135 with psoriasis and/or psoriatic arthritis, 1,749 with Crohn's disease and 825 patients with ulcerative colitis). This includes exposure to STELARA in the controlled and non-controlled periods of the clinical studies for at least 6 months or 1 year (4,577 and 3,253 patients respectively with psoriasis, psoriatic arthritis, Crohn's disease or ulcerative colitis) and exposure for at least 4 or 5 years (1,482 and 838 patients with psoriasis respectively).

Label Table 2 provides a list of adverse reactions from adult psoriasis, psoriatic arthritis, Crohn's disease and ulcerative colitis clinical studies as well as adverse reactions reported from post-marketing experience. The adverse reactions are classified by System Organ Class and frequency, using the following convention: Very common (≥1/10), Common (≥1/100 to <1/10), Uncommon (≥1/1,000 to <1/100), Rare (≥1/10,000 to <1/1,000), Very rare (<1/10,000), not known (cannot be estimated from the available data). Within each frequency grouping, adverse reactions are presented in order of decreasing seriousness.

LABEL TABLE 2

| List of adverse reactions | |
|---|---|
| System Organ Class | Frequency: Adverse reaction |
| Infections and infestations | Common: Upper respiratory tract infection, nasopharyngitis, sinusitis<br>Uncommon: Cellulitis, dental infections, herpes zoster, lower respiratory tract infection, viral upper respiratory tract infection, vulvovaginal mycotic infection |
| Immune system disorders | Uncommon: Hypersensitivity reactions (including rash, urticaria)<br>Rare: Serious hypersensitivity reactions (including anaphylaxis, angioedema) |
| Psychiatric disorders | Uncommon: Depression |
| Nervous system disorders | Common: Dizziness, headache<br>Uncommon: Facial palsy |
| Respiratory, thoracic and mediastinal disorders | Common: Oropharyngeal pain<br>Uncommon: Nasal congestion<br>Rare: Allergic alveolitis, eosinophilic pneumonia |
| Gastrointestinal disorders | Common: Diarrhoea, nausea, vomiting |
| Skin and subcutaneous tissue disorders | Common: Pruritus<br>Uncommon: Pustular psoriasis, skin exfoliation, acne<br>Rare: Exfoliative dermatitis |
| Musculoskeletal and connective tissue disorders | Common: Back pain, myalgia, arthralgia |
| General disorders and administration site conditions | Common: Fatigue, injection site erythema, injection site pain<br>Uncommon: Injection site reactions (including haemorrhage, haematoma, induration, swelling and pruritus), asthenia |

Description of Selected Adverse Reactions

Infections

In the placebo-controlled studies of patients with psoriasis, psoriatic arthritis, Crohn's disease and ulcerative colitis, the rates of infection or serious infection were similar between ustekinumab-treated patients and those treated with placebo. In the placebo-controlled period of these clinical studies, the rate of infection was 1.36 per patient-year of follow-up in ustekinumab-treated patients, and 1.34 in placebo-treated patients. Serious infections occurred at the rate of 0.03 per patient-year of follow-up in ustekinumab-treated patients (30 serious infections in 930 patient-years of follow-up) and 0.03 in placebo-treated patients (15 serious infections in 434 patient-years of follow-up) (see section 4.4).

In the controlled and non-controlled periods of psoriasis, psoriatic arthritis, Crohn's disease and ulcerative colitis clinical studies, representing 11,581 patient-years of exposure in 6,709 patients, the median follow up was 1.0 years; 1.1 years for psoriatic disease studies, 0.6 year for Crohn's disease studies and 1.0 years for ulcerative colitis studies. The rate of infection was 0.91 per patient-year of follow-up in ustekinumab-treated patients, and the rate of serious infections was 0.02 per patient-year of follow-up in ustekinumab-treated patients (199 serious infections in 11,581 patient-years of follow-up) and serious infections reported included pneumonia, anal abscess, cellulitis, diverticulitis, gastroenteritis and viral infections.

In clinical studies, patients with latent tuberculosis who were concurrently treated with isoniazid did not develop tuberculosis.

Malignancies

In the placebo-controlled period of the psoriasis, psoriatic arthritis, Crohn's disease and ulcerative colitis clinical studies, the incidence of malignancies excluding non-melanoma skin cancer was 0.11 per 100 patient-years of follow-up for ustekinumab-treated patients (1 patient in 929 patient-years of follow-up) compared with 0.23 for placebo-treated patients (1 patient in 434 patient-years of follow-up). The incidence of non-melanoma skin cancer was 0.43 per 100 patient-years of follow-up for ustekinumab-treated patients (4 patients in 929 patient-years of follow-up) compared to 0.46 for placebo-treated patients (2 patients in 433 patient-years of follow-up).

In the controlled and non-controlled periods of psoriasis, psoriatic arthritis, Crohn's disease and ulcerative colitis clinical studies, representing 11,561 patient-years of exposure in 6,709 patients, the median follow-up was 1.0 years; 1.1 years for psoriatic disease studies, 0.6 year for Crohn's disease studies and 1.0 years for ulcerative colitis studies. Malignancies excluding non-melanoma skin cancers were reported in 62 patients in 11,561 patient-years of follow-up (incidence of 0.54 per 100 patient-years of follow-up for ustekinumab-treated patients). The incidence of malignancies reported in ustekinumab-treated patients was comparable to the incidence expected in the general population (standardised incidence ratio=0.93 [95% confidence interval: 0.71, 1.20], adjusted for age, gender and race). The most frequently observed malignancies, other than non-melanoma skin cancer, were prostate, colorectal, melanoma and breast cancers. The incidence of non-melanoma skin cancer was 0.49 per 100 patient-years of follow-up for ustekinumab-treated patients (56 patients in 11,545 patient-years of follow-up). The ratio of patients with basal versus squamous cell skin cancers (3:1) is comparable with the ratio expected in the general population (see section 4.4).

Hypersensitivity and Infusion Reactions

In Crohn's disease and ulcerative colitis intravenous induction studies, no events of anaphylaxis or other serious infusion reactions were reported following the single intravenous dose. In these studies, 2.2% of 785 placebo treated patients and 1.9% of 790 patients treated with the recommended dose of ustekinumab reported adverse events occurring during or within an hour of the infusion.

Paediatric Population

Undesirable effects in paediatric patients 12 years and older with plaque psoriasis. The safety of ustekinumab has been studied in a phase 3 study of 110 patients from 12 to 17 years of age for up to 60 weeks. In this study, the adverse events reported were similar to those seen in previous studies in adults with plaque psoriasis.

Reporting of Suspected Adverse Reactions

Reporting suspected adverse reactions after authorisation of the medicinal product is important. It allows continued monitoring of the benefit/risk balance of the medicinal product. Healthcare professionals are asked to report any suspected adverse reactions via the national reporting system listed in Appendix V.

4.9 Overdose

Single doses up to 6 mg/kg have been administered intravenously in clinical studies without dose-limiting toxicity. In case of overdose, it is recommended that the patient be monitored for any signs or symptoms of adverse reactions and appropriate symptomatic treatment be instituted immediately.

5. Pharmacological Properties 5.1 Pharmacodynamic Properties

Pharmacotherapeutic group: Immunosuppressants, interleukin inhibitors, ATC code: L04AC05.

Mechanism of Action

Ustekinumab is a fully human IgG1κ monoclonal antibody that binds with specificity to the shared p40 protein subunit of human cytokines interleukin (IL)-12 and IL-23. Ustekinumab inhibits the bioactivity of human IL-12 and IL-23 by preventing p40 from binding to the IL-12Rβ1 receptor protein expressed on the surface of immune cells. Ustekinumab cannot bind to IL-12 or IL-23 that is already bound to IL-12Rβ1 cell surface receptors. Thus, ustekinumab is not likely to contribute to complement- or antibody-mediated cytotoxicity of cells with IL-12 and/or IL-23 receptors. IL-12 and IL-23 are heterodimeric cytokines secreted by activated antigen presenting cells, such as macrophages and dendritic cells, and both cytokines participate in immune functions; IL-12 stimulates natural killer (NK) cells and drives the differentiation of CD4+ T cells toward the T helper 1 (Th1) phenotype, IL-23 induces the T helper 17 (Th17) pathway. However, abnormal regulation of IL 12 and IL 23 has been associated with immune mediated diseases, such as psoriasis, psoriatic arthritis, Crohn's disease and ulcerative colitis.

By binding the shared p40 subunit of IL-12 and IL-23, ustekinumab may exert its clinical effects in psoriasis, psoriatic arthritis, Crohn's disease and ulcerative colitis through interruption of the Th1 and Th17 cytokine pathways, which are central to the pathology of these diseases.

In patients with Crohn's disease and ulcerative colitis, treatment with ustekinumab resulted in a decrease in inflammatory markers including C-Reactive Protein (CRP) and fecal calprotectin during the induction phase, which were then maintained throughout the maintenance phase.

Immunisation

During the long term extension of Psoriasis Study 2 (PHOENIX 2), adult patients treated with STELARA for at least 3.5 years mounted similar antibody responses to both pneumococcal polysaccharide and tetanus vaccines as a non-systemically treated psoriasis control group. Similar proportions of adult patients developed protective levels of anti-pneumococcal and anti-tetanus antibodies and antibody titers were similar among STELARA-treated and control patients.

Clinical Efficacy

Crohn's Disease

The safety and efficacy of ustekinumab was assessed in three randomized, double-blind, placebo-controlled, multi-center studies in adult patients with moderately to severely active Crohn's disease (Crohn's Disease Activity Index [CDAI] score of ≥220 and ≤450). The clinical development program consisted of two 8-week intravenous induction studies (UNITI-1 and UNITI-2) followed by a 44 week subcutaneous randomized withdrawal maintenance study (IM-UNITI) representing 52 weeks of therapy.

The induction studies included 1409 (UNITI-1, n=769; UNITI-2 n=640) patients. The primary endpoint for both induction studies was the proportion of subjects in clinical response (defined as a reduction in CDAI score of ≥100 points) at week 6. Efficacy data were collected and analyzed through week 8 for both studies. Concomitant doses of oral corticosteroids, immunomodulators, aminosalicylates and antibiotics were permitted and 75% of patients continued to receive at least one of these medications. In both studies, patients were randomised to receive a single intravenous administration of either the recommended tiered dose of approximately 6 mg/kg (see Table 1, section 4.2), a fixed dose of 130 mg ustekinumab, or placebo at week 0.

Patients in UNITI-1 had failed or were intolerant to prior anti-TNFα therapy. Approximately 48% of the patients had failed 1 prior anti-TNFα therapy and 52% had failed 2 or 3 prior anti-TNFα therapies. In this study, 29.1% of the patients had an inadequate initial response (primary non-responders), 69.4% responded but lost response (secondary non-responders), and 36.4% were intolerant to anti-TNFα therapies.

Patients in UNITI-2 had failed at least one conventional therapy, including corticosteroids or immunomodulators, and were either anti-TNF-α naïve (68.6%) or had previously received but not failed anti-TNFα therapy (31.4%).

In both UNITI-1 and UNITI-2, a significantly greater proportion of patients were in clinical response and remission in the ustekinumab treated group compared to placebo (Label Table 3). Clinical response and remission were significant as early as week 3 in ustekinumab treated patients and continued to improve through week 8. In these induction studies, efficacy was higher and better sustained in the tiered dose group compared to the 130 mg dose group, and tiered dosing is therefore the recommended intravenous induction dose.

The maintenance study (IM-UNITI), evaluated 388 patients who achieved 100 point clinical response at week 8 of induction with ustekinumab in studies UNITI-1 and UNITI-2. Patients were randomized to receive a subcutaneous maintenance regimen of either 90 mg ustekinumab every 8 weeks, 90 mg ustekinumab every 12 weeks or placebo for 44 weeks (for recommended maintenance posology, see section 4.2 of the STELARA Solution for injection (vial) and Solution for injection in pre filled syringe SmPC).

Significantly higher proportions of patients maintained clinical remission and response in the ustekinumab treated groups compared to the placebo group at week 44 (see Label Table 4).

LABEL TABLE 4

Maintenance of Clinical Response and Remission in IM-UNITI (week 44; 52 weeks from initiation of the induction dose)

| | Placebo* N = 131[†] | 90 mg ustekinumab every 8 weeks N = 128[†] | 90 mg ustekinumab every 12 weeks N = 129[†] |
|---|---|---|---|
| Clinical Remission | 36% | 53%[a] | 49%[b] |
| Clinical Response | 44% | 59%[b] | 58%[b] |
| Corticosteroid-Free Clinical Remission | 30% | 47%[a] | 43%[c] |
| Clinical Remission in patients: | | | |
| in remission at the start of maintenance therapy | 46% (36/79) | 67% (52/78)[a] | 56% (44/78) |
| who entered from study CRD3002[‡] | 44% (31/70) | 63% (45/72)[c] | 57% (41/72) |

LABEL TABLE 3

Induction of Clinical Response and Remission in UNITI-1 and UNITI 2

| | UNITI-1* | | UNITI-2** | |
|---|---|---|---|---|
| | Placebo N = 247 | Recommended dose of ustekinumab N = 249 | Placebo N = 209 | Recommended dose of ustekinumab N = 209 |
| Clinical Remission, week 8 | 18 (7.3%) | 52 (20.9%)[a] | 41 (19.6%) | 84 (40.2%)[a] |
| Clinical Response (100 point), week 6 | 53 (21.5%) | 84 (33.7%)[b] | 60 (28.7%) | 116 (55.5%)[a] |
| Clinical Response (100 point), week 8 | 50 (20.2%) | 94 (37.8%)[a] | 67 (32.1%) | 121 (57.9%)[a] |
| 70 Point Response, week 3 | 67 (27.1%) | 101 (40.6%)[b] | 66 (31.6%) | 106 (50.7%)[a] |
| 70 Point Response, week 6 | 75 (30.4%) | 109 (43.8%)[b] | 81 (38.8%) | 135 (64.6%)[a] |

Clinical remission is defined as CDAI score <150; Clinical response is defined as reduction in CDAI score by at least 100 points or being in clinical remission
70 point response is defined as reduction in CDAI score by at least 70 points
*Anti-TNFα failures
**Conventional therapy failures
[a]$p < 0.001$
[b]$p < 0.01$ LABEL TABLE 4-continued Maintenance of Clinical Response and Remission in IM-UNITI
(week 44; 52 weeks from initiation of the induction dose)

|  | Placebo* N = 131[†] | 90 mg ustekinumab every 8 weeks N = 128[†] | 90 mg ustekinumab every 12 weeks N = 129[†] |
|---|---|---|---|
| who are Anti-TNFα naïve | 49% (25/51) | 65% (34/52)[c] | 57% (30/53) |
| who entered from study CRD3001[§] | 26% (16/61) | 41% (23/56) | 39% (22/57) |

Clinical remission is defined as CDAI score <150; Clinical response is defined as reduction in CDAI of at least 100 points or being in clinical remission
*The placebo group consisted of patients who were in response to ustekinumab and were randomized to receive placebo at the start of maintenance therapy.
[†]Patients who were in 100 point clinical response to ustekinumab at start of maintenance therapy
[‡]Patients who failed conventional therapy but not anti-TNFα therapy
[§]Patients who are anti-TNFα refractory/intolerant
[a]$p < 0.01$
[b]$p < 0.05$
[c]nominally significant ($p < 0.05$)

In IM-UNITI, 29 of 129 patients did not maintain response to ustekinumab when treated every 12 weeks and were allowed to dose adjust to receive ustekinumab every 8 weeks. Loss of response was defined as a CDAI score ≥220 points and a ≥100 point increase from the CDAI score at baseline. In these patients, clinical remission was achieved in 41.4% of patients 16 weeks after dose adjustment.

Patients who were not in clinical response to ustekinumab induction at week 8 of the UNITI-1 and UNITI-2 induction studies (476 patients) entered into the non-randomized portion of the maintenance study (IM-UNITI) and received a 90 mg subcutaneous injection of ustekinumab at that time. Eight weeks later, 50.5% of the patients achieved clinical response and continued to receive maintenance dosing every 8 weeks; among these patients with continued maintenance dosing, a majority maintained response (68.1%) and achieved remission (50.2%) at week 44, at proportions that were similar to the patients who initially responded to ustekinumab induction.

Of 131 patients who responded to ustekinumab induction, and were randomized to the placebo group at the start of the maintenance study, 51 subsequently lost response and received 90 mg ustekinumab subcutaneously every 8 weeks. The majority of patients who lost response and resumed ustekinumab did so within 24 weeks of the induction infusion. Of these 51 patients, 70.6% achieved clinical response and 39.2% percent achieved clinical remission 16 weeks after receiving the first subcutaneous dose of ustekinumab.

In IM-UNITI, patients who completed the study through week 44 were eligible to continue treatment in a study extension. Among patients who entered the study extension, clinical remission and response were generally maintained through week 92 for both patients who failed TNF-therapies and those who failed conventional therapies.

No new safety concerns were identified in this study extension with up to 2 years of treatment in patients with Crohn's Disease.

Endoscopy

Endoscopic appearance of the mucosa was evaluated in 252 patients with eligible baseline endoscopic disease activity in a substudy. The primary endpoint was change from baseline in Simplified Endoscopic Disease Severity Score for Crohn's Disease (SES-CD), a composite score across 5 ileo-colonic segments of presence/size of ulcers, proportion of mucosal surface covered by ulcers, proportion of mucosal surface affected by any other lesions and presence/type of narrowing/strictures. At week 8, after a single intravenous induction dose, the change in SES-CD score was greater in the ustekinumab group (n=155, mean change=−2.8) than in the placebo group (n=97, mean change=−0.7, p=0.012).

Fistula Response

In a subgroup of patients with draining fistulas at baseline (8.8%; n=26), 12/15 (80%) of ustekinumab-treated patients achieved a fistula response over 44 weeks (defined as ≥50% reduction from baseline of the induction study in the number of draining fistulas) compared to 5/11 (45.5%) exposed to placebo.

Health-Related Quality of Life

Health-related quality of life was assessed by Inflammatory Bowel Disease Questionnaire (IBDQ) and SF-36 questionnaires. At week 8, patients receiving ustekinumab showed statistically significantly greater and clinically meaningful improvements on IBDQ total score and SF-36 Mental Component Summary Score in both UNITI-1 and UNITI-2, and SF-36 Physical Component Summary Score in UNITI-2, when compared to placebo. These improvements were generally better maintained in ustekinumab-treated patients in the IM-UNITI study through week 44 when compared to placebo. Improvement in health-related quality of life was generally maintained during the extension through week 92.

Ulcerative Colitis

The safety and efficacy of ustekinumab was assessed in two randomized, double-blind, placebo-controlled, multi-center studies in adult patients with moderately to severely active ulcerative colitis (Mayo score 6 to 12; Endoscopy subscore ≥2). The clinical development program consisted of one intravenous induction study (referred to as UNIFI-I) with treatment of up to 16 weeks followed by a 44 week subcutaneous randomized withdrawal maintenance study (referred to as UNIFI-M) representing at least 52 weeks of therapy.

Efficacy results presented for UNIFI-I and UNIFI-M were based on central review of endoscopies.

UNIFI-I included 961 patients. The primary endpoint for the induction study was the proportion of subjects in clinical remission at week 8. Patients were randomised to receive a single intravenous administration of either the recommended tiered dose of approximately 6 mg/kg (see Label Table 1, section 4.2), a fixed dose of 130 mg ustekinumab, or placebo at week 0.

Concomitant doses of oral corticosteroids, immunomodulators, and aminosalicylates were permitted and 90% of patients continued to receive at least one of these medications. Enrolled patients had to have failed conventional therapy (corticosteroids or immunomodulators) or at least one biologic (a TNFα antagonist and/or vedolizumab). 49% of patients had failed conventional therapy, but not a biologic (of which 94% where biological-naïve). 51% of patients had failed or were intolerant to a biologic. Approximately 50% of the patients had failed at least 1 prior anti-TNFα therapy (of which 48% were primary non-responders) and 17% had failed at least 1 anti-TNFα therapy and vedolizumab.

In UNIFI-I a significantly greater proportion of patients were in clinical remission in the ustekinumab treated group compared to placebo at week 8 (Label Table 5). As early as Week 2, the earliest scheduled study visit, and at each visit thereafter, a higher proportion of ustekinumab patients had no rectal bleeding or achieved normal stool frequency as compared with placebo patients. Significant differences in partial Mayo score and symptomatic remission were observed between ustekinumab and placebo as early as Week 2.

Efficacy was higher in the tiered dose group (6 mg/kg) compared to the 130 mg dose group in select endpoints, and tiered dosing is therefore the recommended intravenous induction dose.

LABEL TABLE 5

Summary of Key Efficacy Outcomes in UNIFI-I (Week 8)

|  | Placebo N = 319 | Recommended dose of ustekinumab£ N = 322 |
|---|---|---|
| Clinical Remission* | 5% | 16%$^a$ |
| In patients who failed conventional therapy, but not a biologic | 9% (15/158) | 19% (29/156)$^c$ |
| In patients who failed biological therapy¥ | 1% (2/161) | 13% (21/166)$^b$ |
| In patients who failed both a TNF and vedolizumab | 0% (0/47) | 10% (6/58)$^c$ |
| Clinical Response§ | 31% | 62%$^a$ |
| In patients who failed conventional therapy, but not a biologic | 35% (56/158) | 67% (104/156)$^b$ |
| In patients who failed biological therapy¥ | 27% (44/161) | 57% (95/166)$^b$ |
| In patients who failed both a TNF and vedolizumab | 28% (13/47) | 52% (30/58)$^c$ |
| Mucosal Healing† | 14% | 27%$^a$ |
| In patients who failed conventional therapy, but not a biologic | 21% (33/158) | 33% (52/156)$^c$ |
| In patients who failed biological therapy | 7% (11/161) | 21% (35/166)$^b$ |

LABEL TABLE 5-continued

Summary of Key Efficacy Outcomes in UNIFI-I (Week 8)

|  | Placebo N = 319 | Recommended dose of ustekinumab£ N = 322 |
|---|---|---|
| Symptomatic Remission‡ | 23% | 45%$^b$ |
| Combined Symptomatic Remission and Mucosal Healing ⁺ | 8% | 21%$^b$ |

$^£$Infusion dose of ustekinumab using the weight-based dosage regimen specified in Label Table 1.
*Clinical remission is defined as Mayo score ≤2 points, with no individual subscore >1.
§Clinical response is defined as a decrease from baseline in the Mayo score by ≥30% and ≥3 points, with either a decrease from baseline in the rectal bleeding subscore ≥1 or a rectal bleeding subscore of 0 or 1.
¥A TNFα antagonist and/or vedolizumab.
†Mucosal healing is defined as a Mayo endoscopic subscore of 0 or 1.
‡Symptomatic remission is defined as a Mayo stool frequency subscore of 0 or 1 and a rectal bleeding subscore of 0.
⁺ Combined symptomatic remission and mucosal healing is defined as a stool frequency subscore of 0 or 1, a rectal bleeding subscore of 0, and an endoscopy subscore of 0 or 1.
$^a$p < 0.001
$^b$Nominally significant (p < 0.001)
$^c$Nominally significant (p < 0.05)

UNIFI-M, evaluated 523 patients who achieved clinical response with single IV administration of ustekinumab in UNIFI-I. Patients were randomized to receive a subcutaneous maintenance regimen of either 90 mg ustekinumab every 8 weeks, 90 mg ustekinumab every 12 weeks or placebo for 44 weeks (for recommended maintenance posology, see section 4.2 of the STELARA Solution for injection (vial) and Solution for injection in pre filled syringe SmPC).

Significantly greater proportions of patients were in clinical remission in both ustekinumab treated groups compared to the placebo group at week 44 (see Label Table 6).

LABEL TABLE 6

Summary of Key Efficacy Measures in UNIFI-M (week 44; 52 weeks from initiation of the induction dose)

|  | Placebo* N = 175 | 90 mg ustekinumab every 8 Weeks N = 176 | 90 mg ustekinumab every 12 Weeks N = 172 |
|---|---|---|---|
| Clinical Remission** | 24% | 44%$^a$ | 38%$^b$ |
| In patients who failed conventional therapy, but not a biologic | 31% (27/87) | 48% (41/85)$^d$ | 49% (50/102)$^d$ |
| In patients who failed biological therapy¥ | 17% (15/88) | 40% (36/91)$^c$ | 23% (16/70)$^d$ |
| In patients who failed both a TNF and vedolizumab | 15% (4/27) | 33% (7/21)$^e$ | 23% (5/22)$^e$ |
| Maintenance of Clinical Response through week 44§ | 45% | 71%$^a$ | 68%$^a$ |
| In patients who failed conventional therapy, but not a biologic | 51% (44/87) | 78% (66/85)$^c$ | 77% (78/102)$^c$ |
| In patients who failed biological therapy¥ | 39% (34/88) | 65% (59/91)$^c$ | 56% (39/70)$^d$ |
| In patients who failed both a TNF and vedolizumab | 41% (11/27) | 67% (14/21)$^e$ | 50% (11/22)$^e$ |
| Mucosal Healing† | 29% | 51%$^a$ | 44%$^b$ |
| Maintenance of Clinical Remission through week 44£ | 38% (17/45) | 58% (22/38) | 65% (26/40)$^c$ |
| Corticosteroid Free Clinical Remission€ | 23% | 42%$^a$ | 38%$^b$ |
| Durable Remission‖ | 35% | 57%$^c$ | 48%$^d$ |

LABEL TABLE 6-continued

Summary of Key Efficacy Measures in UNIFI-M (week 44; 52 weeks from initiation of the induction dose)

|  | Placebo*<br>N = 175 | 90 mg ustekinumab every 8 Weeks<br>N = 176 | 90 mg ustekinumab every 12 Weeks<br>N = 172 |
|---|---|---|---|
| Symptomatic Remission‡ | 45% | 68%$^c$ | 62%$^d$ |
| Combined Symptomatic Remission and Mucosal Healing⁺ | 28% | 48%$^c$ | 41%$^d$ |

*Following response to IV ustekinumab.
**Clinical remission is defined as Mayo score ≤2 points, with no individual subscore >1.
§Clinical response is defined as a decrease from baseline in the Mayo score by ≥30% and ≥3 points, with either a decrease from baseline in the rectal bleeding subscore ≥1 or a rectal bleeding subscore of 0 or 1.
¥A TNFα antagonist and/or vedolizumab.
†Mucosal healing is defined as a Mayo endoscopic sub-score of 0 or 1.
£Maintenance of clinical remission through Week 44 is defined as patients in clinical remission through Week 44 among patients in clinical remission at maintenance baseline.
€Corticosteroid-free clinical remission is defined as patients in clinical remission and not receiving corticosteroids at Week 44.
∥Durable Remission is defined as partial Mayo remission at ≥80% of all visits prior to Week 44 and in partial Mayo remission at last visit (Week 44).
‡Symptomatic remission is defined as a Mayo stool frequency subscore of 0 or 1 and a rectal bleeding subscore of 0.
⁺Combined symptomatic remission and mucosal healing is defined as a stool frequency subscore of 0 or 1, a rectal bleeding subscore of 0, and an endoscopy subscore of 0 or 1.
$^a$p < 0.001
$^b$p < 0.05
$^c$Nominally significant (p < 0.001)
$^d$Nominally significant (p < 0.05)
$^e$Not statistically significant The beneficial effect of ustekinumab on clinical response, mucosal healing and clinical remission was observed in induction and in maintenance both in patients who failed conventional therapy but not a biologic therapy, as well as in those who had failed at least one prior TNFα antagonist therapy including in patients with a primary non-response to TNFα antagonist therapy. A beneficial effect was also observed in induction in patients who failed at least one prior TNFα antagonist therapy and vedolizumab, however the number of patients in this subgroup was too small to draw definitive conclusions about the beneficial effect in this group during maintenance.

Week 16 Responders to Ustekinumab Induction

Ustekinumab treated patients who were not in response at week 8 of UNIFI-I received an administration of 90 mg SC ustekinumab at week 8 (36% of patients). Of those patients, 9% of patients who were initially randomized to the recommended induction dose achieved clinical remission and 58% achieved clinical response at Week 16.

Patients who were not in clinical response to ustekinumab induction at week 8 of the UNFI-I study but were in response at week 16 (157 patients) entered into the non-randomized portion of UNIFI-M and continued to receive maintenance dosing every 8 weeks; among these patients, a majority (62%) maintained response and 30% achieved remission at week 44.

Endoscopic Normalization

Endoscopic normalization was defined as a Mayo endoscopic subscore of 0 and was observed as early as week 8 of UNIFI-I. At week 44 of UNIFI-M, it was achieved in 24% and 29% of patients treated with ustekinumab every 12 or 8 weeks, respectively, as compared to 18% of patients in the placebo group.

Histologic & Histo Endoscopic Mucosal Healing

Histologic healing (defined as neutrophil infiltration in <5% of crypts, no crypt destruction, and no erosions, ulcerations, or granulation tissue) was assessed at week 8 of UNIFI-I and Week 44 of UNIFI-M. At week 8, after a single intravenous induction dose, significantly greater proportions of patients in the recommended dose group achieved histologic healing (36%) compared with patients in the placebo group (22%). At Week 44 maintenance of this effect was observed with significantly more patients in histologic healing in the every 12 week (54%) and every 8 week (59%) ustekinumab groups as compared to placebo (33%).

A combined endpoint of histo-endoscopic mucosal healing defined as subjects having both mucosal healing and histologic healing was evaluated at week 8 of UNIFI-I and week 44 of UNIFI-M. Patients receiving ustekinumab at the recommended dose showed significant improvements on the histo-endoscopic mucosal healing endpoint at week 8 in the ustekinumab group (18%) as compared to the placebo group (9%). At week 44, maintenance of this effect was observed with significantly more patients in histo-endoscopic mucosal healing in the every 12 week (39%) and every 8 week (46%) ustekinumab groups compared to placebo (24%).

Health-Related Quality of Life

Health-related quality of life was assessed by Inflammatory Bowel Disease Questionnaire (IBDQ), SF-36 and EuroQoL-5D (EQ-5D) questionnaires.

At week 8 of UNIFI-I, patients receiving ustekinumab showed significantly greater and clinically meaningful improvements on IBDQ total score, EQ-5D and EQ-5D VAS, and SF-36 Mental Component Summary Score and SF-36 Physical Component Summary Score when compared to placebo. These improvements were maintained in ustekinumab-treated patients in UNIFI-M through week 44.

Patients receiving ustekinumab experienced significantly more improvements in work productivity as assessed by greater reductions in overall work impairment and in activity impairment as assessed by the WPAI-GH questionnaire than patients receiving placebo.

Hospitalizations and Ulcerative Colits (UC) Related Surgeries

Through week 8 of UNIFI-I, the proportions of subjects with UC disease related hospitalizations were significantly lower for subjects in the ustekinumab recommended dose group (1.6%, 5/322) compared with subjects in the placebo group (4.4%, 14/319) and no subjects underwent UC disease related surgeries in subjects receiving ustekinumab at the recommended induction dose compared to 0.6% (2/319) subjects in the placebo group.

Through week 44 of UNIFI-M, a significantly lower number of UC-related hospitalizations was observed in subjects in the combined ustekinumab group (2.0%, 7/348) as compared with subjects in the placebo group (5.7%, 10/175). A numerically lower number of subjects in the ustekinumab group (0.6%, 2/348) underwent UC disease related surgeries compared with subjects in the placebo group (1.7%, 3/175) through week 44.

Immunogenicity

Antibodies to ustekinumab may develop during ustekinumab treatment and most are neutralising. The formation of anti-ustekinumab antibodies is associated with increased clearance of ustekinumab in patients with Crohn's disease or ulcerative colitis. No reduced efficacy was observed. There is no apparent correlation between the presence of anti-ustekinumab antibodies and the occurrence of injection site reactions.

Paediatric Population

The European Medicines Agency has deferred the obligation to submit the results of studies with ustekinumab in one or more subsets of the paediatric population in Crohn's Disease and ulcerative colitis (see section 4.2 for information on paediatric use).

5.2 Pharmacokinetic Properties

Following the recommended intravenous induction dose, median peak serum ustekinumab concentration, observed 1 hour after the infusion, was 126.1 µg/mL in patients with Crohn's disease and 127.0 µg/mL in patients with ulcerative colitis.

Distribution

Median volume of distribution during the terminal phase (Vz) following a single intravenous administration to patients with psoriasis ranged from 57 to 83 mL/kg.

Biotransformation

The exact metabolic pathway for ustekinumab is unknown.

Elimination

Median systemic clearance (CL) following a single intravenous administration to patients with psoriasis ranged from 1.99 to 2.34 mL/day/kg. Median half-life ($t_{1/2}$) of ustekinumab was approximately 3 weeks in patients with ulcerative colitis, Crohn's disease, psoriasis and/or psoriatic arthritis, ranging from 15 to 32 days across all psoriasis and psoriatic arthritis studies.

Dose Linearity

The systemic exposure of ustekinumab ($C_{max}$ and AUC) increased in an approximately dose-proportional manner after a single intravenous administration at doses ranging from 0.09 mg/kg to 4.5 mg/kg.

Special Populations

No pharmacokinetic data are available in patients with impaired renal or hepatic function. No specific studies have been conducted with intravenous ustekinumab in elderly or paediatric patients.

In patients with Crohn's disease and ulcerative colitis, variability in ustekinumab clearance was affected by body weight, serum albumin level, sex, and antibody to ustekinumab status while body weight was the main covariate affecting the volume of distribution. Additionally in Crohn's disease, clearance was affected by C-reactive protein, TNF antagonist failure status and race (Asian versus non-Asian). The impact of these covariates was within ±20% of the typical or reference value of the respective PK parameter, thus dose adjustment is not warranted for these covariates. Concomitant use of immunomodulators did not have a significant impact on ustekinumab disposition.

Regulation of CYP450 Enzymes

The effects of IL-12 or IL-23 on the regulation of CYP450 enzymes were evaluated in an in vitro study using human hepatocytes, which showed that IL-12 and/or IL-23 at levels of 10 ng/mL did not alter human CYP450 enzyme activities (CYP1A2, 2B6, 2C9, 2C19, 2D6, or 3A4; see section 4.5).

5.3 Preclinical Safety Data

Non-clinical data reveal no special hazard (e.g. organ toxicity) for humans based on studies of repeated-dose toxicity and developmental and reproductive toxicity, including safety pharmacology evaluations. In developmental and reproductive toxicity studies in cynomolgus monkeys, neither adverse effects on male fertility indices nor birth defects or developmental toxicity were observed. No adverse effects on female fertility indices were observed using an analogous antibody to IL-12/23 in mice.

Dose levels in animal studies were up to approximately 45-fold higher than the highest equivalent dose intended to be administered to psoriasis patients and resulted in peak serum concentrations in monkeys that were more than 100-fold higher than observed in humans. Carcinogenicity studies were not performed with ustekinumab due to the lack of appropriate models for an antibody with no cross-reactivity to rodent IL-12/23 p40.

6. Pharmaceutical Particulars 6.1 List of Excipients

EDTA disodium salt dihydrate
L-histidine
L-histidine monohydrochloride monohydrate
L-methionine
Polysorbate 80
Sucrose
Water for injection 6.2 Incompatibilities In the absence of compatibility studies, this medicinal product must not be mixed with other medicinal products. STELARA should only be diluted with sodium chloride 9 mg/mL (0.9%) solution. STELARA should not be administered concomitantly in the same intravenous line with other medicinal products.

6.3 Shelf Life 3 years.
Do not freeze.

Chemical and physical in-use stability has been demonstrated for 8 hours at 15-25° C.

From a microbiological point of view, unless the method of dilution precludes the risk of microbial contamination, the product should be used immediately. If not used immediately, in-use storage times and conditions are the responsibility of user.

6.4 Special Precautions for Storage

Store in a refrigerator (2° C.-8° C.). Do not freeze.
Keep the vial in the outer carton in order to protect from light.

For storage conditions after dilution of the medicinal product, see section 6.3

6.5 Nature and Contents of Container 26 mL solution in a type I glass 30 mL vial closed with a coated butyl rubber stopper. STELARA is available in a 1 vial pack.

6.6 Special Precautions for Disposal and Other Handling

The solution in the STELARA vial should not be shaken. The solution should be visually inspected for particulate matter or discoloration prior to administration. The solution is clear, colourless to light yellow. The medicinal product should not be used if the solution is discoloured or cloudy, or if foreign particulate matter is present.

Dilution

STELARA concentrate for solution for infusion must be diluted and prepared by a healthcare professional using aseptic technique.

1. Calculate the dose and the number of STELARA vials needed based on patient weight (see section 4.2, Label Table 1). Each 26 mL vial of STELARA contains 130 mg of ustekinumab. Only use complete vials of STELARA.
2. Withdraw and discard a volume of the sodium chloride 9 mg/mL (0.9%) solution from the 250 mL infusion bag equal to the volume of STELARA to be added. (discard 26 mL sodium chloride for each vial of STELARA needed, for 2 vials-discard 52 mL, for 3 vials-discard 78 mL, for 4 vials-discard 104 mL)
3. Withdraw 26 mL of STELARA from each vial needed and add it to the 250 mL infusion bag. The final volume in the infusion bag should be 250 mL. Gently mix.
4. Visually inspect the diluted solution before administration. Do not use if visibly opaque particles, discoloration or foreign particles are observed.
5. Administer the diluted solution over a period of at least one hour. Once diluted, the infusion should be completed within eight hours of the dilution in the infusion bag.
6. Use only an infusion set with an in-line, sterile, non-pyrogenic, low protein-binding filter (pore size 0.2 micrometer).
7. Each vial is for single use only and any unused medicinal product should be disposed of in accordance with local requirements.
7. Marketing Authorisation Holder
   Janssen-Cilag International NV
   Turnhoutseweg 30
   2340 Beerse
   Belgium
8. Marketing Authorisation Number(S)
   EU/1/08/494/005
9. Date of First Authorisation/Renewal of the Authorisation
   Date of first authorisation: 16 Jan. 2009
   Date of latest renewal: 19 Sep. 2013
10. Date of Revision of the Text Detailed information on this medicinal product is available on the website of the European Medicines Agency http://www.ema.europa.eu/

1. Name of the Medicinal Product
   STELARA 45 mg solution for injection
   STELARA 90 mg solution for injection
   STELARA 45 mg solution for injection in pre-filled syringe
   STELARA 90 mg solution for injection in pre-filled syringe
2. Qualitative and Quantitative Composition
   STELARA 45 mg Solution for Injection
     Each vial contains 45 mg ustekinumab in 0.5 mL.
   STELARA 90 mg Solution for Injection
     Each vial contains 90 mg ustekinumab in 1 mL.
   STELARA 45 mg Solution for Injection in Pre-Filled Syringe
     Each pre-filled syringe contains 45 mg ustekinumab in 0.5 mL.
   STELARA 90 mg Solution for Injection in Pre-Filled Syringe
     Each pre-filled syringe contains 90 mg ustekinumab in 1 mL.

Ustekinumab is a fully human IgG1κ monoclonal antibody to interleukin (IL)-12/23 produced in a murine myeloma cell line using recombinant DNA technology.

For the full list of excipients, see section 6.1.
3. Pharmaceutical Form
   STELARA 45 mg Solution for Injection
     Solution for injection.
   STELARA 90 mg Solution for Injection
     Solution for injection.
   STELARA 45 mg Solution for Injection in Pre-Filled Syringe
     Solution for injection.
   STELARA 90 mg Solution for Injection in Pre-Filled Syringe
     Solution for injection.

The solution is clear to slightly opalescent, colourless to light yellow.
4. Clinical Particulars 4.1 Therapeutic Indications Plaque Psoriasis STELARA is indicated for the treatment of moderate to severe plaque psoriasis in adults who failed to respond to, or who have a contraindication to, or are intolerant to other systemic therapies including ciclosporin, methotrexate (MTX) or PUVA (psoralen and ultraviolet A) (see section 5.1).

Paediatric Plaque Psoriasis

STELARA is indicated for the treatment of moderate to severe plaque psoriasis in adolescent patients from the age of 12 years and older, who are inadequately controlled by, or are intolerant to, other systemic therapies or phototherapies (see section 5.1).

Psoriatic Arthritis (PsA)

STELARA, alone or in combination with MTX, is indicated for the treatment of active psoriatic arthritis in adult patients when the response to previous non-biological disease-modifying anti-rheumatic drug (DMARD) therapy has been inadequate (see section 5.1).

Crohn's Disease

STELARA is indicated for the treatment of adult patients with moderately to severely active Crohn's disease who have had an inadequate response with, lost response to, or were intolerant to either conventional therapy or a TNFα antagonist or have medical contraindications to such therapies.

Ulcerative Colitis

STELARA is indicated for the treatment of adult patients with moderately to severely active ulcerative colitis who have had an inadequate response with, lost response to, or were intolerant to either conventional therapy or a biologic or have medical contraindications to such therapies (see section 5.1).

4.2 Posology and Method of Administration

STELARA is intended for use under the guidance and supervision of physicians experienced in the diagnosis and treatment of conditions for which STELARA is indicated.

Posology

Plaque Psoriasis

The recommended posology of STELARA is an initial dose of 45 mg administered subcutaneously, followed by a 45 mg dose 4 weeks later, and then every 12 weeks thereafter.

Consideration should be given to discontinuing treatment in patients who have shown no response up to 28 weeks of treatment.

Patients with Body Weight>100 kg

For patients with a body weight>100 kg the initial dose is 90 mg administered subcutaneously, followed by a 90 mg dose 4 weeks later, and then every 12 weeks thereafter. In these patients, 45 mg was also shown to be efficacious. However, 90 mg resulted in greater efficacy. (see section 5.1, Label Table 4)

Psoriatic Arthritis (PsA)

The recommended posology of STELARA is an initial dose of 45 mg administered subcutaneously, followed by a 45 mg dose 4 weeks later, and then every 12 weeks thereafter. Alternatively, 90 mg may be used in patients with a body weight>100 kg.

Consideration should be given to discontinuing treatment in patients who have shown no response up to 28 weeks of treatment.

Elderly (≥65 years)

No dose adjustment is needed for elderly patients (see section 4.4).

Renal and Hepatic Impairment

STELARA has not been studied in these patient populations. No dose recommendations can be made.

Paediatric Population

The safety and efficacy of STELARA in children with psoriasis less than 12 years of age or in children with psoriatic arthritis less than 18 years of age have not yet been established.

Paediatric Plaque Psoriasis (12 Years and Older)

The recommended dose of STELARA based on body weight is shown below (Label Tables 1 and 2). STELARA should be administered at Weeks 0 and 4, then every 12 weeks thereafter.

LABEL TABLE 1

Recommended dose of STELARA for paediatric psoriasis

| Body weight at the time of dosing | Recommended Dose |
|---|---|
| <60 kg | 0.75 mg/kg[a] |
| ≥60-≤100 kg | 45 mg |
| >100 kg | 90 mg |

[a]To calculate the volume of injection (mL) for patients < 60 kg, use the following formula: body weight (kg) x 0.0083 (mL/kg) or see Label Table 2. The calculated volume should be rounded to the nearest 0.01 mL and administered using a 1 mL graduated syringe. A 45 mg vial is available for paediatric patients who need to receive less than the full 45 mg dose.

LABEL TABLE 2

Injection volumes of STELARA for paediatric psoriasis patients <60 kg

| Body weight at time of dosing (kg) | Dose (mg) | Volume of injection (mL) |
|---|---|---|
| 30 | 22.5 | 0.25 |
| 31 | 23.3 | 0.26 |

LABEL TABLE 2-continued

Injection volumes of STELARA for paediatric psoriasis patients <60 kg

| Body weight at time of dosing (kg) | Dose (mg) | Volume of injection (mL) |
|---|---|---|
| 32 | 24.0 | 0.27 |
| 33 | 24.8 | 0.27 |
| 34 | 25.5 | 0.28 |
| 35 | 26.3 | 0.29 |
| 36 | 27.0 | 0.30 |
| 37 | 27.8 | 0.31 |
| 38 | 28.5 | 0.32 |
| 39 | 29.3 | 0.32 |
| 40 | 30.0 | 0.33 |
| 41 | 30.8 | 0.34 |
| 42 | 31.5 | 0.35 |
| 43 | 32.3 | 0.36 |
| 44 | 33.0 | 0.37 |
| 45 | 33.8 | 0.37 |
| 46 | 34.5 | 0.38 |
| 47 | 35.3 | 0.39 |
| 48 | 36.0 | 0.40 |
| 49 | 36.8 | 0.41 |
| 50 | 37.5 | 0.42 |
| 51 | 38.3 | 0.42 |
| 52 | 39.0 | 0.43 |
| 53 | 39.8 | 0.44 |
| 54 | 40.5 | 0.45 |
| 55 | 41.3 | 0.46 |
| 56 | 42.0 | 0.46 |
| 57 | 42.8 | 0.47 |
| 58 | 43.5 | 0.48 |
| 59 | 44.3 | 0.49 |

Consideration should be given to discontinuing treatment in patients who have shown no response up to 28 weeks of treatment.

Crohn's Disease and Ulcerative Colitis

In the treatment regimen, the first dose of STELARA is administered intravenously. For the posology of the intravenous dosing regimen, see section 4.2 of the STELARA 130 mg Concentrate for solution for infusion SmPC.

The first subcutaneous administration of 90 mg STELARA should take place at week 8 after the intravenous dose. After this, dosing every 12 weeks is recommended.

Patients who have not shown adequate response at 8 weeks after the first subcutaneous dose, may receive a second subcutaneous dose at this time (see section 5.1).

Patients who lose response on dosing every 12 weeks may benefit from an increase in dosing frequency to every 8 weeks (see section 5.1, section 5.2).

Patients may subsequently be dosed every 8 weeks or every 12 weeks according to clinical judgment (see section 5.1).

Consideration should be given to discontinuing treatment in patients who show no evidence of therapeutic benefit 16 weeks after the IV induction dose or 16 weeks after switching to the 8-weekly maintenance dose.

Immunomodulators and/or corticosteroids may be continued during treatment with STELARA. In patients who have responded to treatment with STELARA, corticosteroids may be reduced or discontinued in accordance with standard of care.

In Crohn's disease, if therapy is interrupted, resumption of treatment with subcutaneous dosing every 8 weeks is safe and effective.

Elderly (≥65 Years)

No dose adjustment is needed for elderly patients (see section 4.4).

Renal and Hepatic Impairment

STELARA has not been studied in these patient populations. No dose recommendations can be made.

Paediatric Population

The safety and efficacy of STELARA in treatment of Crohn's disease or ulcerative colitis in children less than 18 years have not yet been established. No data are available.

Method of Administration

STELARA 45 mg and 90 mg vials or pre-filled syringes are for subcutaneous injection only. If possible, areas of the skin that show psoriasis should be avoided as injection sites.

After proper training in subcutaneous injection technique, patients or their caregivers may inject STELARA if a physician determines that it is appropriate. However, the physician should ensure appropriate follow-up of patients. Patients or their caregivers should be instructed to inject the prescribed amount of STELARA according to the directions provided in the package leaflet.

Comprehensive instructions for administration are given in the package leaflet.

For further instructions on preparation and special precautions for handling, see section 6.6.

4.3 Contraindications

Hypersensitivity to the active substance or to any of the excipients listed in section 6.1.

Clinically important, active infection (e.g. active tuberculosis; see section 4.4).

4.4 Special Warnings and Precautions for Use

Traceability

In order to improve the traceability of biological medicinal products, the tradename and the batch number of the administered product should be clearly recorded.

Infections

Ustekinumab may have the potential to increase the risk of infections and reactivate latent infections. In clinical studies, serious bacterial, fungal, and viral infections have been observed in patients receiving STELARA (see section 4.8).

Caution should be exercised when considering the use of STELARA in patients with a chronic infection or a history of recurrent infection (see section 4.3).

Prior to initiating treatment with STELARA, patients should be evaluated for tuberculosis infection. STELARA must not be given to patients with active tuberculosis (see section 4.3). Treatment of latent tuberculosis infection should be initiated prior to administering STELARA. Antituberculosis therapy should also be considered prior to initiation of STELARA in patients with a history of latent or active tuberculosis in whom an adequate course of treatment cannot be confirmed. Patients receiving STELARA should be monitored closely for signs and symptoms of active tuberculosis during and after treatment.

Patients should be instructed to seek medical advice if signs or symptoms suggestive of an infection occur. If a patient develops a serious infection, the patient should be closely monitored and STELARA should not be administered until the infection resolves.

Malignancies

Immunosuppressants like ustekinumab have the potential to increase the risk of malignancy. Some patients who received STELARA in clinical studies developed cutaneous and non-cutaneous malignancies (see section 4.8).

No studies have been conducted that include patients with a history of malignancy or that continue treatment in patients who develop malignancy while receiving STELARA. Thus, caution should be exercised when considering the use of STELARA in these patients.

All patients, in particular those greater than 60 years of age, patients with a medical history of prolonged immunosuppressant therapy or those with a history of PUVA treatment, should be monitored for the appearance of non-melanoma skin cancer (see section 4.8).

Systemic and respiratory hypersensitivity reactions

Systemic

Serious hypersensitivity reactions have been reported in the postmarketing setting, in some cases several days after treatment. Anaphylaxis and angioedema have occurred. If an anaphylactic or other serious hypersensitivity reaction occurs, appropriate therapy should be instituted and administration of STELARA should be discontinued (see section 4.8).

Respiratory

Cases of allergic alveolitis and eosinophilic pneumonia have been reported during post-approval use of ustekinumab. Clinical presentations included cough, dyspnoea, and interstitial infiltrates following one to three doses. Serious outcomes have included respiratory failure and prolonged hospitalisation. Improvement has been reported after discontinuation of ustekinumab and also, in some cases, administration of corticosteroids. If infection has been excluded and diagnosis is confirmed, discontinue ustekinumab and institute appropriate treatment (see section 4.8).

Latex Sensitivity

The needle cover on the syringe in the STELARA pre-filled syringe is manufactured from dry natural rubber (a derivative of latex), which may cause allergic reactions in individuals sensitive to latex.

Vaccinations

It is recommended that live viral or live bacterial vaccines (such as *Bacillus* of Calmette and Guérin (BCG)) should not be given concurrently with STELARA. Specific studies have not been conducted in patients who had recently received live viral or live bacterial vaccines. No data are available on the secondary transmission of infection by live vaccines in patients receiving STELARA. Before live viral or live bacterial vaccination, treatment with STELARA should be withheld for at least 15 weeks after the last dose and can be resumed at least 2 weeks after vaccination. Prescribers should consult the Summary of Product Characteristics for the specific vaccine for additional information and guidance on concomitant use of immunosuppressive agents post-vaccination.

Patients receiving STELARA may receive concurrent inactivated or non-live vaccinations.

Long term treatment with STELARA does not suppress the humoral immune response to pneumococcal polysaccharide or tetanus vaccines (see section 5.1).

Concomitant Immunosuppressive Therapy

In psoriasis studies, the safety and efficacy of STELARA in combination with immunosuppressants, including biologics, or phototherapy have not been evaluated. In psoriatic arthritis studies, concomitant MTX use did not appear to influence the safety or efficacy of STELARA. In Crohn's disease and ulcerative colitis studies, concomitant use of immunosuppressants or corticosteroids did not appear to influence the safety or efficacy of STELARA. Caution should be exercised when considering concomitant use of other immunosuppressants and STELARA or when transitioning from other immunosuppressive biologics (see section 4.5).

Immunotherapy

STELARA has not been evaluated in patients who have undergone allergy immunotherapy. It is not known whether STELARA may affect allergy immunotherapy.

Serious Skin Conditions

In patients with psoriasis, exfoliative dermatitis has been reported following ustekinumab treatment (see section 4.8). Patients with plaque psoriasis may develop erythrodermic psoriasis, with symptoms that may be clinically indistinguishable from exfoliative dermatitis, as part of the natural course of their disease. As part of the monitoring of the patient's psoriasis, physicians should be alert for symptoms of erythrodermic psoriasis or exfoliative dermatitis. If these symptoms occur, appropriate therapy should be instituted. STELARA should be discontinued if a drug reaction is suspected.

Special Populations

Elderly (≥65 years)

No overall differences in efficacy or safety in patients age 65 and older who received STELARA were observed compared to younger patients in clinical studies in approved indications, however the number of patients aged 65 and older is not sufficient to determine whether they respond differently from younger patients. Because there is a higher incidence of infections in the elderly population in general, caution should be used in treating the elderly.

4.5 Interaction with Other Medicinal Products and Other Forms of Interaction

Live vaccines should not be given concurrently with STELARA (see section 4.4).

No interaction studies have been performed in humans. In the population pharmacokinetic analyses of the phase III studies, the effect of the most frequently used concomitant medicinal products in patients with psoriasis (including paracetamol, ibuprofen, acetylsalicylic acid, metformin, atorvastatin, levothyroxine) on pharmacokinetics of ustekinumab was explored. There were no indications of an interaction with these concomitantly administered medicinal products. The basis for this analysis was that at least 100 patients (>5% of the studied population) were treated concomitantly with these medicinal products for at least 90% of the study period. The pharmacokinetics of ustekinumab was not impacted by concomitant use of MTX, NSAIDs, 6-mercaptopurine, azathioprine and oral corticosteroids in patients with psoriatic arthritis, Crohn's disease or ulcerative colitis, or prior exposure to anti-TNFα agents, in patients with psoriatic arthritis or Crohn's disease or by prior exposure to biologics (i.e. anti-TNFα agents and/or vedolizumab) in patients with ulcerative colitis.

The results of an in vitro study do not suggest the need for dose adjustments in patients who are receiving concomitant CYP450 substrates (see section 5.2).

In psoriasis studies, the safety and efficacy of STELARA in combination with immunosuppressants, including biologics, or phototherapy have not been evaluated. In psoriatic arthritis studies, concomitant MTX use did not appear to influence the safety or efficacy of STELARA. In Crohn's disease and ulcerative colitis studies, concomitant use of immunosuppressants or corticosteroids did not appear to influence the safety or efficacy of STELARA. (see section 4.4).

4.6 Fertility, Pregnancy and Lactation

Women of Childbearing Potential

Women of childbearing potential should use effective methods of contraception during treatment and for at least 15 weeks after treatment.

Pregnancy

There are no adequate data from the use of ustekinumab in pregnant women. Animal studies do not indicate direct or indirect harmful effects with respect to pregnancy, embryonic/foetal development, parturition or postnatal development (see section 5.3). As a precautionary measure, it is preferable to avoid the use of STELARA in pregnancy.

Breast-Feeding

It is unknown whether ustekinumab is excreted in human breast milk. Animal studies have shown excretion of ustekinumab at low levels in breast milk. It is not known if ustekinumab is absorbed systemically after ingestion. Because of the potential for adverse reactions in nursing infants from ustekinumab, a decision on whether to discontinue breast-feeding during treatment and up to 15 weeks after treatment or to discontinue therapy with STELARA must be made taking into account the benefit of breast-feeding to the child and the benefit of STELARA therapy to the woman.

Fertility

The effect of ustekinumab on human fertility has not been evaluated (see section 5.3).

4.7 Effects on Ability to Drive and Use Machines

STELARA has no or negligible influence on the ability to drive and use machines.

4.8 Undesirable Effects

Summary of the Safety Profile

The most common adverse reactions (>5%) in controlled periods of the adult psoriasis, psoriatic arthritis, Crohn's disease and ulcerative colitis clinical studies with ustekinumab were nasopharyngitis and headache. Most were considered to be mild and did not necessitate discontinuation of study treatment. The most serious adverse reaction that has been reported for STELARA is serious hypersensitivity reactions including anaphylaxis (see section 4.4). The overall safety profile was similar for patients with psoriasis, psoriatic arthritis, Crohn's disease and ulcerative colitis.

Tabulated List of Adverse Reactions

The safety data described below reflect exposure in adults to ustekinumab in 14 phase 2 and phase 3 studies in 6,709 patients (4,135 with psoriasis and/or psoriatic arthritis, 1,749 with Crohn's disease and 825 patients with ulcerative colitis). This includes exposure to STELARA in the controlled and non-controlled periods of the clinical studies for at least 6 months or 1 year (4,577 and 3,253 patients respectively with psoriasis, psoriatic arthritis, Crohn's disease or ulcerative colitis) and exposure for at least 4 or 5 years (1,482 and 838 patients with psoriasis respectively).

Table 3 provides a list of adverse reactions from adult psoriasis, psoriatic arthritis, Crohn's disease and ulcerative colitis clinical studies as well as adverse reactions reported from post-marketing experience. The adverse reactions are classified by System Organ Class and frequency, using the following convention: Very common (≥1/10), Common (≥1/100 to <1/10), Uncommon (≥1/1,000 to <1/100), Rare (≥1/10,000 to <1/1,000), Very rare (≤1/10,000), not known (cannot be estimated from the available data). Within each frequency grouping, adverse reactions are presented in order of decreasing seriousness.

LABEL TABLE 3

List of adverse reactions

| System Organ Class | Frequency: Adverse reaction |
|---|---|
| Infections and infestations | Common: Upper respiratory tract infection, nasopharyngitis, sinusitis<br>Uncommon: Cellulitis, dental infections, herpes zoster, lower respiratory tract infection, viral upper respiratory tract infection, vulvovaginal mycotic infection |
| Immune system disorders | Uncommon: Hypersensitivity reactions (including rash, urticaria)<br>Rare: Serious hypersensitivity reactions (including anaphylaxis, angioedema) |
| Psychiatric disorders | Uncommon: Depression |
| Nervous system disorders | Common: Dizziness, headache<br>Uncommon: Facial palsy |
| Respiratory, thoracic and mediastinal disorders | Common: Oropharyngeal pain<br>Uncommon: Nasal congestion<br>Rare: Allergic alveolitis, eosinophilic pneumonia |
| Gastrointestinal disorders | Common: Diarrhoea, nausea, vomiting |
| Skin and subcutaneous tissue disorders | Common: Pruritus<br>Uncommon: Pustular psoriasis, skin exfoliation, acne<br>Rare: Exfoliative dermatitis |
| Musculoskeletal and connective tissue disorders | Common: Back pain, myalgia, arthralgia |
| General disorders and administration site conditions | Common: Fatigue, injection site erythema, injection site pain<br>Uncommon: Injection site reactions (including haemorrhage, haematoma, induration, swelling and pruritus), asthenia |

Description of Selected Adverse Reactions
Infections

In the placebo-controlled studies of patients with psoriasis, psoriatic arthritis, Crohn's disease and ulcerative colitis, the rates of infection or serious infection were similar between ustekinumab-treated patients and those treated with placebo. In the placebo-controlled period of these clinical studies, the rate of infection was 1.36 per patient-year of follow-up in ustekinumab-treated patients, and 1.34 in placebo-treated patients. Serious infections occurred at the rate of 0.03 per patient-year of follow-up in ustekinumab-treated patients (30 serious infections in 930 patient-years of follow-up) and 0.03 in placebo-treated patients (15 serious infections in 434 patient-years of follow-up) (see section 4.4).

In the controlled and non-controlled periods of psoriasis, psoriatic arthritis, Crohn's disease and ulcerative colitis clinical studies, representing 11,581 patient-years of exposure in 6,709 patients, the median follow up was 1.0 years; 1.1 years for psoriatic disease studies, 0.6 year for Crohn's disease studies, and 1.0 years for ulcerative colitis studies. The rate of infection was 0.91 per patient-year of follow-up in ustekinumab-treated patients, and the rate of serious infections was 0.02 per patient-year of follow-up in ustekinumab-treated patients (199 serious infections in 11,581 patient-years of follow-up) and serious infections reported included pneumonia, anal abscess, cellulitis, diverticulitis, gastroenteritis and viral infections.

In clinical studies, patients with latent tuberculosis who were concurrently treated with isoniazid did not develop tuberculosis.
Malignancies In the placebo-controlled period of the psoriasis, psoriatic arthritis, Crohn's disease and ulcerative colitis clinical studies, the incidence of malignancies excluding non-melanoma skin cancer was 0.11 per 100 patient-years of follow-up for ustekinumab-treated patients (1 patient in 929 patient-years of follow-up) compared with 0.23 for placebo-treated patients (1 patient in 434 patient-years of follow-up). The incidence of non-melanoma skin cancer was 0.43 per 100 patient-years of follow-up for ustekinumab-treated patients (4 patients in 929 patient-years of follow-up) compared to 0.46 for placebo-treated patients (2 patients in 433 patient-years of follow-up).

In the controlled and non-controlled periods of psoriasis, psoriatic arthritis, Crohn's disease and ulcerative colitis clinical studies, representing 11,561 patient-years of exposure in 6,709 patients, the median follow-up was 1.0 years; 1.1 years for psoriatic disease studies, 0.6 year for Crohn's disease studies and 1.0 years for ulcerative colitis studies. Malignancies excluding non-melanoma skin cancers were reported in 62 patients in 11,561 patient-years of follow-up (incidence of 0.54 per 100 patient-years of follow-up for ustekinumab-treated patients). The incidence of malignancies reported in ustekinumab-treated patients was comparable to the incidence expected in the general population (standardised incidence ratio=0.93 [95% confidence interval: 0.71, 1.20], adjusted for age, gender and race). The most frequently observed malignancies, other than non-melanoma skin cancer, were prostate, colorectal, melanoma and breast cancers. The incidence of non-melanoma skin cancer was 0.49 per 100 patient-years of follow-up for ustekinumab-treated patients (56 patients in 11,545 patient-years of follow-up). The ratio of patients with basal versus squamous cell skin cancers (3:1) is comparable with the ratio expected in the general population (see section 4.4).
Hypersensitivity Reactions During the controlled periods of the psoriasis and psoriatic arthritis clinical studies of ustekinumab, rash and urticaria have each been observed in <1% of patients (see section 4.4).
Paediatric Population Undesirable effects in paediatric patients 12 years and older with plaque psoriasis The safety of ustekinumab has been studied in a phase 3 study of 110 patients from 12 to 17 years of age for up to 60 weeks. In this study, the adverse events reported were similar to those seen in previous studies in adults with plaque psoriasis.
Reporting of Suspected Adverse Reactions Reporting suspected adverse reactions after authorisation of the medicinal product is important. It allows continued monitoring of the benefit/risk balance of the medicinal product. Healthcare professionals are asked to report any suspected adverse reactions via the national reporting system listed in Appendix V.
4.9 Overdose Single doses up to 6 mg/kg have been administered intravenously in clinical studies without dose-limiting toxicity. In case of overdose, it is recommended that the patient be monitored for any signs or symptoms of adverse reactions and appropriate symptomatic treatment be instituted immediately.
5. Pharmacological Properties
5.1 Pharmacodynamic Properties Pharmacotherapeutic group: Immunosuppressants, interleukin inhibitors, ATC code: L04AC05.
Mechanism of Action Ustekinumab is a fully human IgG1K monoclonal antibody that binds with specificity to the shared p40 protein subunit of human cytokines interleukin (IL)-12 and IL-23.

Ustekinumab inhibits the bioactivity of human IL-12 and IL-23 by preventing p40 from binding to the IL-12Rβ1 receptor protein expressed on the surface of immune cells. Ustekinumab cannot bind to IL-12 or IL-23 that is already bound to IL-12Rβ1 cell surface receptors. Thus, ustekinumab is not likely to contribute to complement- or antibody-mediated cytotoxicity of cells with IL-12 and/or IL-23 receptors. IL-12 and IL-23 are heterodimeric cytokines secreted by activated antigen presenting cells, such as macrophages and dendritic cells, and both cytokines participate in immune functions; IL-12 stimulates natural killer (NK) cells and drives the differentiation of CD4+ T cells toward the T helper 1 (Th1) phenotype, IL-23 induces the T helper 17 (Th17) pathway. However, abnormal regulation of IL 12 and IL 23 has been associated with immune mediated diseases, such as psoriasis, psoriatic arthritis, Crohn's disease and ulcerative colitis.

By binding the shared p40 subunit of IL-12 and IL-23, ustekinumab may exert its clinical effects in psoriasis, psoriatic arthritis, Crohn's disease and ulcerative colitis through interruption of the Th1 and Th17 cytokine pathways, which are central to the pathology of these diseases.

In patients with Crohn's disease and ulcerative colitis, treatment with ustekinumab resulted in a decrease in inflammatory markers including C-Reactive Protein (CRP) and fecal calprotectin during the induction phase, which were then maintained throughout the maintenance phase.

Immunisation

During the long term extension of Psoriasis Study 2 (PHOENIX 2), adult patients treated with STELARA for at least 3.5 years mounted similar antibody responses to both pneumococcal polysaccharide and tetanus vaccines as a non-systemically treated psoriasis control group. Similar proportions of adult patients developed protective levels of anti-pneumococcal and anti-tetanus antibodies and antibody titers were similar among STELARA-treated and control patients.

Clinical Efficacy

Plaque Psoriasis (Adults)

The safety and efficacy of ustekinumab was assessed in 1,996 patients in two randomised, double-blind, placebo-controlled studies in patients with moderate to severe plaque psoriasis and who were candidates for phototherapy or systemic therapy. In addition, a randomised, blinded assessor, active-controlled study compared ustekinumab and etanercept in patients with moderate to severe plaque psoriasis who had had an inadequate response to, intolerance to, or contraindication to ciclosporin, MTX, or PUVA.

Psoriasis Study 1 (PHOENIX 1) evaluated 766 patients. 53% of these patients were either non-responsive, intolerant, or had a contraindication to other systemic therapy. Patients randomised to ustekinumab received 45 mg or 90 mg doses at Weeks 0 and 4 and followed by the same dose every 12 weeks. Patients randomised to receive placebo at Weeks 0 and 4 crossed over to receive ustekinumab (either 45 mg or 90 mg) at Weeks 12 and 16 followed by dosing every 12 weeks. Patients originally randomised to ustekinumab who achieved Psoriasis Area and Severity Index 75 response (PASI improvement of at least 75% relative to baseline) at both Weeks 28 and 40 were re-randomised to receive ustekinumab every 12 weeks or to placebo (i.e., withdrawal of therapy). Patients who were re-randomised to placebo at week 40 reinitiated ustekinumab at their original dosing regimen when they experienced at least a 50% loss of their PASI improvement obtained at week 40. All patients were followed for up to 76 weeks following first administration of study treatment.

Psoriasis Study 2 (PHOENIX 2) evaluated 1,230 patients. 61% of these patients were either non-responsive, intolerant, or had a contraindication to other systemic therapy. Patients randomised to ustekinumab received 45 mg or 90 mg doses at Weeks 0 and 4 followed by an additional dose at 16 weeks. Patients randomised to receive placebo at Weeks 0 and 4 crossed over to receive ustekinumab (either 45 mg or 90 mg) at Weeks 12 and 16. All patients were followed for up to 52 weeks following first administration of study treatment.

Psoriasis Study 3 (ACCEPT) evaluated 903 patients with moderate to severe psoriasis who inadequately responded to, were intolerant to, or had a contraindication to other systemic therapy and compared the efficacy of ustekinumab to etanercept and evaluated the safety of ustekinumab and etanercept. During the 12-week active-controlled portion of the study, patients were randomised to receive etanercept (50 mg twice a week), ustekinumab 45 mg at Weeks 0 and 4, or ustekinumab 90 mg at Weeks 0 and 4.

Baseline disease characteristics were generally consistent across all treatment groups in Psoriasis Studies 1 and 2 with a median baseline PASI score from 17 to 18, median baseline Body Surface Area (BSA)≥20, and median Dermatology Life Quality Index (DLQI) range from 10 to 12.

Approximately one third (Psoriasis Study 1) and one quarter (Psoriasis Study 2) of subjects had Psoriatic Arthritis (PsA). Similar disease severity was also seen in Psoriasis Study 3.

The primary endpoint in these studies was the proportion of patients who achieved PASI 75 response from baseline at week 12 (see Label Tables 4 and 5).

LABEL TABLE 4

Summary of clinical response in Psoriasis Study 1 (PHOENIX 1) and Psoriasis Study 2 (PHOENIX 2)

|  | Week 12 2 doses (week 0 and week 4) | | | Week 28 3 doses (week 0, week 4 and week 16) | |
|---|---|---|---|---|---|
|  | PBO | 45 mg | 90 mg | 45 mg | 90 mg |
| Psoriasis Study 1 | | | | | |
| Number of patients randomised | 255 | 255 | 256 | 250 | 243 |
| PASI 50 response N (%) | 26 (10%) | 213 (84%)$^a$ | 220 (86%)$^a$ | 228 (91%) | 234 (96%) |
| PASI 75 response N (%) | 8 (3%) | 171 (67%)$^a$ | 170 (66%)$^a$ | 178 (71%) | 191 (79%) |
| PASI 90 response N (%) | 5 (2%) | 106 (42%)$^a$ | 94 (37%)$^a$ | 123 (49%) | 135 (56%) |
| PGA$^b$ of cleared or minimal N (%) | 10 (4%) | 151 (59%)$^a$ | 156 (61%)$^a$ | 146 (58%) | 160 (66%) |

LABEL TABLE 4-continued

Summary of clinical response in Psoriasis Study 1 (PHOENIX 1) and Psoriasis Study 2 (PHOENIX 2)

| | Week 12 2 doses (week 0 and week 4) | | | Week 28 3 doses (week 0, week 4 and week 16) | |
|---|---|---|---|---|---|
| | PBO | 45 mg | 90 mg | 45 mg | 90 mg |
| Number of patients ≤100 kg | 166 | 168 | 164 | 164 | 153 |
| PASI 75 response N (%) | 6 (4%) | 124 (74%) | 107 (65%) | 130 (79%) | 124 (81%) |
| Number of patients >100 kg | 89 | 87 | 92 | 86 | 90 |
| PASI 75 response N (%) | 2 (2%) | 47 (54%) | 63 (68%) | 48 (56%) | 67 (74%) |
| Psoriasis Study 2 | | | | | |
| Number of patients randomised | 410 | 409 | 411 | 397 | 400 |
| PASI 50 response N (%) | 41 (10%) | 342 (84%)$^a$ | 367 (89%)$^a$ | 369 (93%) | 380 (95%) |
| PASI 75 response N (%) | 15 (4%) | 273 (67%)$^a$ | 311 (76%)$^a$ | 276 (70%) | 314 (79%) |
| PASI 90 response N (%) | 3 (1%) | 173 (42%)$^a$ | 209 (51%)$^a$ | 178 (45%) | 217 (54%) |
| PGA$^b$ of cleared or minimal N (%) | 18 (4%) | 277 (68%)$^a$ | 300 (73%)$^a$ | 241 (61%) | 279 (70%) |
| Number of patients ≤100 kg | 290 | 297 | 289 | 287 | 280 |
| PASI 75 response N (%) | 12 (4%) | 218 (73%) | 225 (78%) | 217 (76%) | 226 (81%) |
| Number of patients >100 kg | 120 | 112 | 121 | 110 | 119 |
| PASI 75 response N (%) | 3 (3%) | 55 (49%) | 86 (71%) | 59 (54%) | 88 (74%) |

$^a$p < 0.001 for ustekinumab 45 mg or 90 mg in comparison with placebo (PBO).
$^b$PGA = Physician Global Assessment

LABEL TABLE 5

Summary of clinical response at week 12 in Psoriasis Study 3 (ACCEPT)

| | Psoriasis Study 3 | | |
|---|---|---|---|
| | Etanercept 24 doses (50 mg twice a week) | Ustekinumab 2 doses (week 0 and week 4) | |
| | | 45 mg | 90 mg |
| Number of patients randomised | 347 | 209 | 347 |
| PASI 50 response N (%) | 286 (82%) | 181 (87%) | 320 (92%)$^a$ |
| PASI 75 response N (%) | 197 (57%) | 141 (67%)$^b$ | 256 (74%)$^a$ |
| PASI 90 response N (%) | 80 (23%) | 76 (36%)$^a$ | 155 (45%)$^a$ |
| PGA of cleared or minimal N (%) | 170 (49%) | 136 (65%)$^a$ | 245 (71%)$^a$ |
| Number of patients ≤100 kg | 251 | 151 | 244 |
| PASI 75 response N (%) | 154 (61%) | 109 (72%) | 189 (77%) |
| Number of patients >100 kg | 96 | 58 | 103 |
| PASI 75 response N (%) | 43 (45%) | 32 (55%) | 67 (65%) |

$^a$p < 0.001 for ustekinumab 45 mg or 90 mg in comparison with etanercept.
$^b$p = 0.012 for ustekinumab 45 mg in comparison with etanercept.

In Psoriasis Study 1 maintenance of PASI 75 was significantly superior with continuous treatment compared with treatment withdrawal (p<0.001). Similar results were seen with each dose of ustekinumab. At 1 year (week 52), 89% of patients re-randomised to maintenance treatment were PASI 75 responders compared with 63% of patients re-randomised to placebo (treatment withdrawal) (p<0.001). At 18 months (week 76), 84% of patients re-randomised to maintenance treatment were PASI 75 responders compared with 19% of patients re-randomised to placebo (treatment withdrawal). At 3 years (week 148), 82% of patients re-randomised to maintenance treatment were PASI 75 responders. At 5 years (week 244), 80% of patients re-randomised to maintenance treatment were PASI 75 responders.

In patients re-randomised to placebo, and who reinitiated their original ustekinumab treatment regimen after loss of ≥50% of PASI improvement 85% regained PASI 75 response within 12 weeks after re-initiating therapy.

In Psoriasis Study 1, at week 2 and week 12, significantly greater improvements from baseline were demonstrated in the DLQI in each ustekinumab treatment group compared with placebo. The improvement was sustained through week 28. Similarly, significant improvements were seen in Psoriasis Study 2 at week 4 and 12, which were sustained through week 24. In Psoriasis Study 1, improvements in nail psoriasis (Nail Psoriasis Severity Index), in the physical and mental component summary scores of the SF-36 and in the Itch Visual Analogue Scale (VAS) were also significant in each ustekinumab treatment group compared with placebo. In Psoriasis Study 2, the Hospital Anxiety and Depression Scale (HADS) and Work Limitations Questionnaire (WLQ)

were also significantly improved in each ustekinumab treatment group compared with placebo.

Psoriatic Arthritis (PsA) (Adults)

Ustekinumab has been shown to improve signs and symptoms, physical function and health-related quality of life, and reduce the rate of progression of peripheral joint damage in adult patients with active PsA.

The safety and efficacy of ustekinumab was assessed in 927 patients in two randomised, double-blind, placebo-controlled studies in patients with active PsA (≥5 swollen joints and ≥5 tender joints) despite non-steroidal anti-inflammatory (NSAID) or disease modifying antirheumatic (DMARD) therapy. Patients in these studies had a diagnosis of PsA for at least 6 months. Patients with each subtype of PsA were enrolled, including polyarticular arthritis with no evidence of rheumatoid nodules (39%), spondylitis with peripheral arthritis (28%), asymmetric peripheral arthritis (21%), distal interphalangeal involvement (12%) and arthritis mutilans (0.5%). Over 70% and 40% of the patients in both studies had enthesitis and dactylitis at baseline, respectively. Patients were randomised to receive treatment with ustekinumab 45 mg, 90 mg, or placebo subcutaneously at Weeks 0 and 4 followed by every 12 weeks (q12w) dosing. Approximately 50% of patients continued on stable doses of MTX (≤25 mg/week).

In PsA Study 1 (PSUMMIT I) and PsA Study 2 (PSUMMIT II), 80% and 86% of the patients, respectively, had been previously treated with DMARDs. In Study 1 previous treatment with anti-tumour necrosis factor (TNF)α agent was not allowed. In Study 2, the majority of patients (58%, n=180) had been previously treated with one or more anti-TNFα agent(s), of whom over 70% had discontinued their anti-TNFα treatment for lack of efficacy or intolerance at any time.

Signs and Symptoms

Treatment with ustekinumab resulted in significant improvements in the measures of disease activity compared to placebo at week 24. The primary endpoint was the percentage of patients who achieved American College of Rheumatology (ACR) 20 response at week 24. The key efficacy results are shown in Label Table 6 below.

LABEL TABLE 6

Number of patients who achieved clinical response in Psoriatic arthritis Study 1 (PSUMMIT I) and Study 2 (PSUMMIT II) at week 24

| | Psoriatic arthritis Study 1 | | | Psoriatic arthritis Study 2 | | |
|---|---|---|---|---|---|---|
| | PBO | 45 mg | 90 mg | PBO | 45 mg | 90 mg |
| Number of patients randomised | 206 | 205 | 204 | 104 | 103 | 105 |
| ACR 20 response, N (%) | 47 (23%) | 87 (42%)[a] | 101 (50%)[a] | 21 (20%) | 45 (44%)[a] | 46 (44%)[a] |
| ACR 50 response, N (%) | 18 (9%) | 51 (25%)[a] | 57 (28%)[a] | 7 (7%) | 18 (17%)[b] | 24 (23%)[a] |
| ACR 70 response, N (%) | 5 (2%) | 25 (12%)[a] | 29 (14%)[a] | 3 (3%) | 7 (7%)[c] | 9 (9%)[c] |
| Number of patients with ≥3% BSA[d] | 146 | 145 | 149 | 80 | 80 | 81 |
| PASI 75 response, N (%) | 16 (11%) | 83 (57%)[a] | 93 (62%)[a] | 4 (5%) | 41 (51%)[a] | 45 (56%)[a] |
| PASI 90 response, N (%) | 4 (3%) | 60 (41%)[a] | 65 (44%)[a] | 3 (4%) | 24 (30%)[a] | 36 (44%)[a] |
| Combined PASI 75 and ACR 20 response, N (%) | 8 (5%) | 40 (28%)[a] | 62 (42%)[a] | 2 (3%) | 24 (30%)[a] | 31 (38%)[a] |
| Number of patients ≤100 kg | 154 | 153 | 154 | 74 | 74 | 73 |
| ACR 20 response, N (%) | 39 (25%) | 67 (44%) | 78 (51%) | 17 (23%) | 32 (43%) | 34 (47%) |
| Number of patients with ≥3% BSA[d] | 105 | 105 | 111 | 54 | 58 | 57 |
| PASI 75 response, N (%) | 14 (13%) | 64 (61%) | 73 (66%) | 4 (7%) | 31 (53%) | 32 (56%) |
| Number of patients >100 kg | 52 | 52 | 50 | 30 | 29 | 31 |
| ACR 20 response, N (%) | 8 (15%) | 20 (38%) | 23 (46%) | 4 (13%) | 13 (45%) | 12 (39%) |
| Number of patients with ≥3% BSA[d] | 41 | 40 | 38 | 26 | 22 | 24 |
| PASI 75 response, N (%) | 2 (5%) | 19 (48%) | 20 (53%) | 0 | 10 (45%) | 13 (54%) |

[a] p < 0.001
[b] p < 0.05
[c] p = NS
[d] Number of patients with ≥3% BSA psoriasis skin involvement at baseline ACR 20, 50 and 70 responses continued to improve or were maintained through week 52 (PsA Study 1 and 2) and week 100 (PsA Study 1). In PsA Study 1, ACR 20 responses at week 100 were achieved by 57% and 64%, for 45 mg and 90 mg, respectively. In PsA Study 2, ACR 20 responses at week 52 were achieved by 47% and 48%, for 45 mg and 90 mg, respectively.

The proportion of patients achieving a modified PsA response criteria (PsARC) response was also significantly greater in the ustekinumab groups compared to placebo at week 24. PsARC responses were maintained through weeks 52 and 100. A higher proportion of patients treated with ustekinumab who had spondylitis with peripheral arthritis as their primary presentation, demonstrated 50 and 70 percent improvement in Bath Ankylosing Spondylitis Disease Activity Index (BASDAI) scores compared with placebo at week 24.

Responses observed in the ustekinumab treated groups were similar in patients receiving and not receiving concomitant MTX, and were maintained through weeks 52 and 100. Patients previously treated with anti-TNFα agents who received ustekinumab achieved a greater response at week 24 than patients receiving placebo (ACR 20 response at week 24 for 45 mg and 90 mg was 37% and 34%, respectively, compared with placebo 15%; p<0.05), and responses were maintained through week 52.

For patients with enthesitis and/or dactylitis at baseline, in PsA Study 1 significant improvement in enthesitis and dactylitis score was observed in the ustekinumab groups compared with placebo at week 24. In PsA Study 2 significant improvement in enthesitis score and numerical improvement (not statistically significant) in dactylitis score was observed in the ustekinumab 90 mg group compared with placebo at week 24. Improvements in enthesitis score and dactylitis score were maintained through weeks 52 and 100.

Radiographic Response

Structural damage in both hands and feet was expressed as change in total van der Heijde-Sharp score (vdH-S score), modified for PsA by addition of hand distal interphalangeal joints, compared to baseline. A pre-specified integrated analysis combining data from 927 subjects in both PsA Study 1 and 2 was performed. Ustekinumab demonstrated a statistically significant decrease in the rate of progression of structural damage compared to placebo, as measured by change from baseline to week 24 in the total modified vdH-S score (mean±SD score was 0.97±3.85 in the placebo group compared with 0.40±2.11 and 0.39±2.40 in the ustekinumab 45 mg (p<0.05) and 90 mg (p<0.001) groups, respectively). This effect was driven by PsA Study 1. The effect is considered demonstrated irrespective of concomitant MTX use, and was maintained through Weeks 52 (integrated analysis) and 100 (PsA Study 1).

Physical Function and Health-Related Quality of Life

Ustekinumab-treated patients showed significant improvement in physical function as assessed by the Disability Index of the Health Assessment Questionnaire (HAQ-DI) at week 24. The proportion of patients achieving a clinically meaningful ≥0.3 improvement in HAQ-DI score from baseline was also significantly greater in the ustekinumab groups when compared with placebo. Improvement in HAQ-DI score from baseline was maintained through Weeks 52 and 100.

There was significant improvement in DLQI scores in the ustekinumab groups as compared with placebo at week 24, which was maintained through weeks 52 and 100. In PsA Study 2 there was a significant improvement in Functional Assessment of Chronic Illness Therapy-Fatigue (FACIT-F) scores in the ustekinumab groups when compared with placebo at week 24. The proportion of patients achieving a clinically significant improvement in fatigue (4 points in FACIT-F) was also significantly greater in the ustekinumab groups compared with placebo. Improvements in FACIT scores were maintained through week 52.

Paediatric Population

The European Medicines Agency has deferred the obligation to submit the results of studies with ustekinumab in one or more subsets of the paediatric population aged 6 to 11 years in moderate to severe plaque psoriasis and juvenile idiopathic arthritis (see section 4.2 for information on paediatric use).

Paediatric Plaque Psoriasis

Ustekinumab has been shown to improve signs and symptoms, and health related quality of life in paediatric patients 12 years and older with plaque psoriasis.

The efficacy of ustekinumab was studied in 110 paediatric patients aged 12 to 17 years with moderate to severe plaque psoriasis in a multicenter, Phase 3, randomised, double blind, placebo controlled study (CADMUS). Patients were randomised to receive either placebo (n=37), or the recommended dose of ustekinumab (see section 4.2; n=36) or half of the recommended dose of ustekinumab (n=37) by subcutaneous injection at Weeks 0 and 4 followed by every 12 week (q12w) dosing. At week 12, placebo treated patients crossed over to receive ustekinumab.

Patients with PASI≥12, PGA≥3 and BSA involvement of at least 10%, who were candidates for systemic therapy or phototherapy, were eligible for the study. Approximately 60% of the patients had prior exposure to conventional systemic therapy or phototherapy. Approximately 11% of the patients had prior exposure to biologics.

The primary endpoint was the proportion of patients who achieve a PGA score of cleared (0) or minimal (1) at week 12. Secondary endpoints included PASI 75, PASI 90, change from baseline in Children's Dermatology Life Quality Index (CDLQI), change from baseline in the total scale score of PedsQL (Paediatric Quality of Life Inventory) at week 12. At week 12, subjects treated with ustekinumab showed significantly greater improvement in their psoriasis and health related quality of life compared with placebo (Table 7).

All patients were followed for efficacy for up to 52 weeks following first administration of study agent. The proportion of patients with a PGA score of cleared (0) or minimal (1) and the proportion achieving PASI 75 showed separation between the ustekinumab treated group and placebo at the first post-baseline visit at week 4, reaching a maximum by week 12.

Improvements in PGA, PASI, CDLQI and PedsQL were maintained through week 52 (Label Table 7).

LABEL TABLE 7

Summary of primary and secondary endpoints at week
12 and week 52 Paediatric psoriasis study (CADMUS)

|  | Week 12 | | Week 52 |
| --- | --- | --- | --- |
|  | Placebo<br>N (%) | Recommended<br>dose of<br>Ustekinumab<br>N (%) | Recommended<br>dose of<br>Ustekinumab<br>N (%) |
| Patients randomised | 37 | 36 | 35 |
| PGA | | | |
| PGA of cleared (0) or minimal (1) | 2 (5.4%) | 25 (69.4%)$^a$ | 20 (57.1%) |
| PGA of Cleared (0) | 1 (2.7%) | 17 (47.2%)$^a$ | 13 (37.1%) |
| PASI | | | |
| PASI 75 responders | 4 (10.8%) | 29 (80.6%)$^a$ | 28 (80.0%) |
| PASI 90 responders | 2 (5.4%) | 22 (61.1%)$^a$ | 23 (65.7%) |
| PASI 100 responders | 1 (2.7%) | 14 (38.9%)$^a$ | 13 (37.1%) |
| CDLQI | | | |
| CDLQI of 0 or 1$^b$ | 6 (16.2%) | 18 (50.0%)$^c$ | 20 (57.1%) |
| PedsQL | | | |
| Change from baseline Mean (SD)$^d$ | 3.35 (10.04) | 8.03 (10.44)$^e$ | 7.26 (10.92) |

$^a$p < 0.001
$^b$CDLQI: The CDLQI is a dermatology instrument to assess the effect of a skin problem on the health-related quality of life in the paediatric population. CDLQI of 0 or 1 indicates no effect on child's quality of life.
$^c$p = 0.002
$^d$PedsQL: The PedsQL Total Scale Score is a general health-related quality of life measure developed for use in children and adolescent populations. For the placebo group at week 12, N = 36
$^e$p = 0.028

During the placebo controlled period through week 12, the efficacy of both the recommended and half of the recommended dose groups were generally comparable at the primary endpoint (69.4% and 67.6% respectively) although there was evidence of a dose response for higher level efficacy criteria (e.g. PGA of cleared (0), PASI 90). Beyond week 12, efficacy was generally higher and better sustained in the recommended dose group compared with half of the recommended dosage group in which a modest loss of efficacy was more frequently observed toward the end of each 12 week dosing interval. The safety profiles of the recommended dose and half of the recommended dose were comparable.

Crohn's Disease

The safety and efficacy of ustekinumab was assessed in three randomized, double-blind, placebo-controlled, multi-center studies in adult patients with moderately to severely active Crohn's disease (Crohn's Disease Activity Index [CDAI] score of ≥220 and ≤450). The clinical development program consisted of two 8-week intravenous induction studies (UNITI-1 and UNITI-2) followed by a 44 week subcutaneous randomized withdrawal maintenance study (IM-UNITI) representing 52 weeks of therapy.

The induction studies included 1409 (UNITI-1, n=769; UNITI-2 n=640) patients. The primary endpoint for both induction studies was the proportion of subjects in clinical response (defined as a reduction in CDAI score of ≥100 points) at week 6. Efficacy data were collected and analyzed through week 8 for both studies. Concomitant doses of oral corticosteroids, immunomodulators, aminosalicylates and antibiotics were permitted and 75% of patients continued to receive at least one of these medications. In both studies, patients were randomised to receive a single intravenous administration of either the recommended tiered dose of approximately 6 mg/kg (see section 4.2 of the STELARA 130 mg Concentrate for solution for infusion SmPC), a fixed dose of 130 mg ustekinumab, or placebo at week 0.

Patients in UNITI-1 had failed or were intolerant to prior anti-TNFα therapy. Approximately 48% of the patients had failed 1 prior anti-TNFα therapy and 52% had failed 2 or 3 prior anti-TNFα therapies. In this study, 29.1% of the patients had an inadequate initial response (primary non-responders), 69.4% responded but lost response (secondary non-responders), and 36.4% were intolerant to anti-TNFα therapies.

Patients in UNITI-2 had failed at least one conventional therapy, including corticosteroids or immunomodulators, and were either anti-TNF-α naïve (68.6%) or had previously received but not failed anti-TNFα therapy (31.4%).

In both UNITI-1 and UNITI-2, a significantly greater proportion of patients were in clinical response and remission in the ustekinumab treated group compared to placebo (Label Table 8). Clinical response and remission were significant as early as week 3 in ustekinumab treated patients and continued to improve through week 8. In these induction studies, efficacy was higher and better sustained in the tiered dose group compared to the 130 mg dose group, and tiered dosing is therefore the recommended intravenous induction dose.

LABEL TABLE 8

Induction of Clinical Response and Remission in UNITI-1 and UNITI 2

|  | UNITI-1* | | UNITI-2** | |
|---|---|---|---|---|
|  | Placebo<br>N = 247 | Recommended dose of ustekinumab<br>N = 249 | Placebo<br>N = 209 | Recommended dose of ustekinumab<br>N = 209 |
| Clinical Remission, week 8 | 18 (7.3%) | 52 (20.9%)$^a$ | 41 (19.6%) | 84 (40.2%)$^a$ |
| Clinical Response (100 point), week 6 | 53 (21.5%) | 84 (33.7%)$^b$ | 60 (28.7%) | 116 (55.5%)$^a$ |
| Clinical Response (100 point), week 8 | 50 (20.2%) | 94 (37.8%)$^a$ | 67 (32.1%) | 121 (57.9%)$^a$ |
| 70 Point Response, week 3 | 67 (27.1%) | 101 (40.6%)$^b$ | 66 (31.6%) | 106 (50.7%)$^a$ |
| 70 Point Response, week 6 | 75 (30.4%) | 109 (43.8%)$^b$ | 81 (38.8%) | 135 (64.6%)$^a$ |

Clinical remission is defined as CDAI score <150; Clinical response is defined as reduction in CDAI score by at least 100 points or being in clinical remission 70 point response is defined as reduction in CDAI score by at least 70 points

*Anti-TNFα failures

**Conventional therapy failures $^a$p < 0.001

$^b$p < 0.01

The maintenance study (IM-UNITI), evaluated 388 patients who achieved 100 point clinical response at week 8 of induction with ustekinumab in studies UNITI-1 and UNITI-2. Patients were randomized to receive a subcutaneous maintenance regimen of either 90 mg ustekinumab every 8 weeks, 90 mg ustekinumab every 12 weeks or placebo for 44 weeks (for recommended maintenance posology, see section 4.2).

Significantly higher proportions of patients maintained clinical remission and response in the ustekinumab treated groups compared to the placebo group at week 44 (see Label Table 9).

LABEL TABLE 9

Maintenance of Clinical Response and Remission in IM-UNITI (week 44; 52 weeks from initiation of the induction dose)

|  | Placebo*<br>N = 131$^†$ | 90 mg ustekinumab every 8 weeks<br>N = 128$^†$ | 90 mg ustekinumab every 12 weeks<br>N = 129$^†$ |
|---|---|---|---|
| Clinical Remission | 36% | 53%$^a$ | 49%$^b$ |
| Clinical Response | 44% | 59%$^b$ | 58%$^b$ |
| Corticosteroid-Free Clinical Remission | 30% | 47%$^a$ | 43%$^c$ |
| Clinical Remission in patients: | | | |
| in remission at the start of maintenance therapy | 46% (36/79) | 67% (52/78)$^a$ | 56% (44/78) |
| who entered from study CRD3002$^‡$ | 44% (31/70) | 63% (45/72)$^c$ | 57% (41/72) |
| who are Anti-TNFα naïve | 49% (25/51) | 65% (34/52)$^c$ | 57% (30/53) |
| who entered from study CRD3001$^§$ | 26% (16/61) | 41% (23/56) | 39% (22/57) |

Clinical remission is defined as CDAI score <150; Clinical response is defined as reduction in CDAI of at least 100 points or being in clinical remission

*The placebo group consisted of patients who were in response to ustekinumab and were randomized to receive placebo at the start of maintenance therapy.

$^†$Patients who were in 100 point clinical response to ustekinumab at start of maintenance therapy $^‡$Patients who failed conventional therapy but not anti-TNFα therapy $^§$Patients who are anti-TNFα refractory/intolerant $^a$p < 0.01

$^b$p < 0.05

$^c$nominally significant (p < 0.05)

In IM-UNITI, 29 of 129 patients did not maintain response to ustekinumab when treated every 12 weeks and were allowed to dose adjust to receive ustekinumab every 8 weeks. Loss of response was defined as a CDAI score ≥220 points and a ≥100 point increase from the CDAI score at baseline. In these patients, clinical remission was achieved in 41.4% of patients 16 weeks after dose adjustment.

Patients who were not in clinical response to ustekinumab induction at week 8 of the UNITI-1 and UNITI-2 induction studies (476 patients) entered into the non-randomized portion of the maintenance study (IM-UNITI) and received a 90 mg subcutaneous injection of ustekinumab at that time. Eight weeks later, 50.5% of the patients achieved clinical response and continued to receive maintenance dosing every 8 weeks; among these patients with continued maintenance dosing, a majority maintained response (68.1%) and achieved remission (50.2%) at week 44, at proportions that were similar to the patients who initially responded to ustekinumab induction.

Of 131 patients who responded to ustekinumab induction, and were randomized to the placebo group at the start of the maintenance study, 51 subsequently lost response and received 90 mg ustekinumab subcutaneously every 8 weeks. The majority of patients who lost response and resumed ustekinumab did so within 24 weeks of the induction infusion. Of these 51 patients, 70.6% achieved clinical response and 39.2% percent achieved clinical remission 16 weeks after receiving the first subcutaneous dose of ustekinumab.

In IM-UNITI, patients who completed the study through week 44 were eligible to continue treatment in a study extension. Among patients who entered the study extension, clinical remission and response were generally maintained through week 92 for both patients who failed TNF-therapies and those who failed conventional therapies.

No new safety concerns were identified in this study extension with up to 2 years of treatment in patients with Crohn's Disease.

Endoscopy

Endoscopic appearance of the mucosa was evaluated in 252 patients with eligible baseline endoscopic disease activity in a substudy. The primary endpoint was change from baseline in Simplified Endoscopic Disease Severity Score for Crohn's Disease (SES-CD), a composite score across 5 ileo-colonic segments of presence/size of ulcers, proportion of mucosal surface covered by ulcers, proportion of mucosal surface affected by any other lesions and presence/type of narrowing/strictures. At week 8, after a single intravenous induction dose, the change in SES-CD score was greater in the ustekinumab group (n=155, mean change=−2.8) than in the placebo group (n=97, mean change=−0.7, p=0.012).

Fistula Response

In a subgroup of patients with draining fistulas at baseline (8.8%; n=26), 12/15 (80%) of ustekinumab-treated patients achieved a fistula response over 44 weeks (defined as ≥50% reduction from baseline of the induction study in the number of draining fistulas) compared to 5/11 (45.5%) exposed to placebo.

Health-Related Quality of Life

Health-related quality of life was assessed by Inflammatory Bowel Disease Questionnaire (IBDQ) and SF-36 questionnaires. At week 8, patients receiving ustekinumab showed statistically significantly greater and clinically meaningful improvements on IBDQ total score and SF-36 Mental Component Summary Score in both UNITI-1 and UNITI-2, and SF-36 Physical Component Summary Score in UNITI-2, when compared to placebo. These improvements were generally better maintained in ustekinumab-treated patients in the IM-UNITI study through week 44 when compared to placebo. Improvement in health-related quality of life was generally maintained during the extension through week 92.

Ulcerative Colitis

The safety and efficacy of ustekinumab was assessed in two randomized, double-blind, placebo-controlled, multi-center studies in adult patients with moderately to severely active ulcerative colitis (Mayo score 6 to 12; Endoscopy subscore ≥2). The clinical development program consisted of one intravenous induction study (referred to as UNIFI-I) with treatment of up to 16 weeks followed by a 44 week subcutaneous randomized withdrawal maintenance study (referred to as UNIFI-M) representing at least 52 weeks of therapy.

Efficacy results presented for UNIFI-I and UNIFI-M were based on central review of endoscopies.

UNIFI-I included 961 patients. The primary endpoint for the induction study was the proportion of subjects in clinical remission at week 8. Patients were randomised to receive a single intravenous administration of either the recommended tiered dose of approximately 6 mg/kg (see Label Table 1, section 4.2), a fixed dose of 130 mg ustekinumab, or placebo at week 0.

Concomitant doses of oral corticosteroids, immunomodulators, and aminosalicylates were permitted and 90% of patients continued to receive at least one of these medications. Enrolled patients had to have failed conventional therapy (corticosteroids or immunomodulators) or at least one biologic (a TNFα antagonist and/or vedolizumab). 49% of patients had failed conventional therapy, but not a biologic (of which 94% where biological-naïve). 51% of patients had failed or were intolerant to a biologic. Approximately 50% of the patients had failed at least 1 prior anti-TNFα therapy (of which 48% were primary non-responders) and 17% had failed at least 1 anti-TNFα therapy and vedolizumab.

In UNIFI-I a significantly greater proportion of patients were in clinical remission in the ustekinumab treated group compared to placebo at week 8 (Label Table 10). As early as Week 2, the earliest scheduled study visit, and at each visit thereafter, a higher proportion of ustekinumab patients had no rectal bleeding or achieved normal stool frequency as compared with placebo patients. Significant differences in partial Mayo score and symptomatic remission were observed between ustekinumab and placebo as early as Week 2.

Efficacy was higher in the tiered dose group (6 mg/kg) compared to the 130 mg dose group in select endpoints, and tiered dosing is therefore the recommended intravenous induction dose.

LABEL TABLE 10

Summary of Key Efficacy Outcomes in UNIFI-I (Week 8)

|  | Placebo N = 319 | Recommended dose of ustekinumab$^£$ N = 322 |
|---|---|---|
| Clinical Remission* | 5% | 16%$^a$ |
| In patients who failed conventional therapy, but not a biologic | 9% (15/158) | 19% (29/156)$^c$ |
| In patients who failed biological therapy$^¥$ | 1% (2/161) | 13% (21/166)$^b$ |
| In patients who failed both a TNF and vedolizumab | 0% (0/47) | 10% (6/58%)$^c$ |
| Clinical Response$^§$ | 31% | 62%$^a$ |
| In patients who failed conventional therapy, but not a biologic | 35% (56/158) | 67% (104/156)$^b$ |
| In patients who failed biological therapy$^¥$ | 27% (44/161) | 57% (95/166)$^b$ |
| In patients who failed both a TNF and vedolizumab | 28% (13/47) | 52% (30/58)$^c$ |
| Mucosal Healing$^†$ | 14% | 27%$^a$ |
| In patients who failed conventional therapy, but not a biologic | 21% (33/158) | 33% (52/156)$^c$ |
| In patients who failed biological therapy | 7% (11/161) | 21% (35/166)$^b$ |
| Symptomatic Remission$^‡$ | 23% | 45%$^b$ |
| Combined Symptomatic Remission and Mucosal Healing$^ⱡ$ | 8% | 21%$^b$ |

$^£$Infusion dose of ustekinumab using the weight-based dosage regimen specified in Table 1.
*Clinical remission is defined as Mayo score ≤2 points, with no individual subscore >1.
$^§$Clinical response is defined as a decrease from baseline in the Mayo score by ≥30% and ≥3 points, with either a decrease from baseline in the rectal bleeding subscore ≥1 or a rectal bleeding subscore of 0 or 1.
$^¥$A TNFα antagonist and/or vedolizumab.
$^†$Mucosal healing is defined as a Mayo endoscopic subscore of 0 or 1.
$^‡$Symptomatic remission is defined as a Mayo stool frequency subscore of 0 or 1 and a rectal bleeding subscore of 0.
$^ⱡ$Combined symptomatic remission and mucosal healing is defined as a stool frequency subscore of 0 or 1, a rectal bleeding subscore of 0, and an endoscopy subscore of 0 or 1.
$^a$p < 0.001
$^b$Nominally significant (p < 0.001)
$^c$Nominally significant (p < 0.05)

UNIFI-M, evaluated 523 patients who achieved clinical response with single IV administration of ustekinumab in UNIFI-I. Patients were randomized to receive a subcutaneous maintenance regimen of either 90 mg ustekinumab every 8 weeks, 90 mg ustekinumab every 12 weeks or placebo for 44 weeks (for recommended maintenance posology, see section 4.2 of the STELARA Solution for injection (vial) and Solution for injection in pre filled syringe SmPC).

Significantly greater proportions of patients were in clinical remission in both ustekinumab treated groups compared to the placebo group at week 44 (see Label Table 11).

LABEL TABLE 11

Summary of Key Efficacy Measures in UNIFI-M (week 44; 52 weeks from initiation of the induction dose)

|  | Placebo* N = 175 | 90 mg ustekinumab every 8 Weeks N = 176 | 90 mg ustekinumab every 12 Weeks N = 172 |
|---|---|---|---|
| Clinical Remission** | 24% | 44%$^a$ | 38%$^b$ |
| In patients who failed conventional therapy, but not a biologic | 31% (27/87) | 48% (41/85)$^d$ | 49% (50/102)$^d$ |
| In patients who failed biological therapy$^¥$ | 17% (15/88) | 40% (36/91)$^c$ | 23% (16/70)$^d$ |
| In patients who failed both a TNF and vedolizumab | 15% (4/27) | 33% (7/21)$^e$ | 23% (5/22)$^e$ |
| Maintenance of Clinical Response through week 44$^§$ | 45% | 71%$^a$ | 68%$^a$ |
| In patients who failed conventional therapy, but not a biologic | 51% (44/87) | 78% (66/85)$^c$ | 77% (78/102)$^c$ |
| In patients who failed biological therapy$^¥$ | 39% (34/88) | 65% (59/91)$^c$ | 56% (39/70)$^d$ |
| In patients who failed both a TNF and vedolizumab | 41% (11/27) | 67% (14/21)$^e$ | 50% (11/22)$^e$ |
| Mucosal Healing$^†$ | 29% | 51%$^a$ | 44%$^b$ |
| Maintenance of Clinical Remission through week 44$^£$ | 38% (17/45) | 58% (22/38) | 65% (26/40)$^c$ |
| Corticosteroid Free Clinical Remission$^∊$ | 23% | 42%$^a$ | 38%$^b$ |
| Durable Remission$^∥$ | 35% | 57%$^c$ | 48%$^d$ |

LABEL TABLE 11-continued

Summary of Key Efficacy Measures in UNIFI-M (week 44; 52 weeks from initiation of the induction dose)

|  | Placebo* N = 175 | 90 mg ustekinumab every 8 Weeks N = 176 | 90 mg ustekinumab every 12 Weeks N = 172 |
|---|---|---|---|
| Symptomatic Remission‡ | 45% | 68%$^c$ | 62%$^d$ |
| Combined Symptomatic Remission and Mucosal Healing⸸ | 28% | 48%$^c$ | 41%$^d$ |

*Following response to IV ustekinumab.
**Clinical remission is defined as Mayo score ≤2 points, with no individual subscore >1.
§Clinical response is defined as a decrease from baseline in the Mayo score by ≥30% and ≥3 points, with either a decrease from baseline in the rectal bleeding subscore ≥1 or a rectal bleeding subscore of 0 or 1.
¶A TNFα antagonist and/or vedolizumab.
†Mucosal healing is defined as a Mayo endoscopic sub-score of 0 or 1.
£Maintenance of clinical remission through Week 44 is defined as patients in clinical remission through Week 44 among patients in clinical remission at maintenance baseline.
€Corticosteroid-free clinical remission is defined as patients in clinical remission and not receiving corticosteroids at Week 44.
‖Durable Remission is defined as partial Mayo remission at ≥80% of all visits prior to Week 44 and in partial Mayo remission at last visit (Week 44).
‡Symptomatic remission is defined as a Mayo stool frequency subscore of 0 or 1 and a rectal bleeding subscore of 0.
⸸ Combined symptomatic remission and mucosal healing is defined as a stool frequency subscore of 0 or 1, a rectal bleeding subscore of 0, and an endoscopy subscore of 0 or 1.
$^a$p < 0.001
$^b$p < 0.05
$^c$Nominally significant (p < 0.001)
$^d$Nominally significant (p < 0.05)
$^e$Not statistically significant The beneficial effect of ustekinumab on clinical response, mucosal healing and clinical remission was observed in induction and in maintenance both in patients who failed conventional therapy but not a biologic therapy, as well as in those who had failed at least one prior TNFα antagonist therapy including in patients with a primary non-response to TNFα antagonist therapy. A beneficial effect was also observed in induction in patients who failed at least one prior TNFα antagonist therapy and vedolizumab, however the number of patients in this subgroup was too small to draw definitive conclusions about the beneficial effect in this group during maintenance.

Week 16 Responders to Ustekinumab Induction

Ustekinumab treated patients who were not in response at week 8 of UNIFI-I received an administration of 90 mg SC ustekinumab at week 8 (36% of patients). Of those patients, 9% of patients who were initially randomized to the recommended induction dose achieved clinical remission and 58% achieved clinical response at Week 16.

Patients who were not in clinical response to ustekinumab induction at week 8 of the UNFI-I study but were in response at week 16 (157 patients) entered into the non-randomized portion of UNIFI-M and continued to receive maintenance dosing every 8 weeks; among these patients, a majority (62%) maintained response and 30% achieved remission at week 44.

Endoscopic Normalization

Endoscopic normalization was defined as a Mayo endoscopic subscore of 0 and was observed as early as week 8 of UNIFI-I. At week 44 of UNIFI-M, it was achieved in 24% and 29% of patients treated with ustekinumab every 12 or 8 weeks, respectively, as compared to 18% of patients in the placebo group.

Histologic & Histo Endoscopic Mucosal Healing

Histologic healing (defined as neutrophil infiltration in <5% of crypts, no crypt destruction, and no erosions, ulcerations, or granulation tissue) was assessed at week 8 of UNIFI-I and Week 44 of UNIFI-M. At week 8, after a single intravenous induction dose, significantly greater proportions of patients in the recommended dose group achieved histologic healing (36%) compared with patients in the placebo group (22%). At Week 44 maintenance of this effect was observed with significantly more patients in histologic healing in the every 12 week (54%) and every 8 week (59%) ustekinumab groups as compared to placebo (33%).

A combined endpoint of histo-endoscopic mucosal healing defined as subjects having both mucosal healing and histologic healing was evaluated at week 8 of UNIFI-I and week 44 of UNIFI-M. Patients receiving ustekinumab at the recommended dose showed significant improvements on the histo-endoscopic mucosal healing endpoint at week 8 in the ustekinumab group (18%) as compared to the placebo group (9%). At week 44, maintenance of this effect was observed with significantly more patients in histo-endoscopic mucosal healing in the every 12 week (39%) and every 8 week (46%) ustekinumab groups as compared to placebo (24%).

Health-Related Quality of Life

Health-related quality of life was assessed by Inflammatory Bowel Disease Questionnaire (IBDQ), SF-36 and EuroQoL-5D (EQ-5D) questionnaires.

At week 8 of UNIFI-I, patients receiving ustekinumab showed significantly greater and clinically meaningful improvements on IBDQ total score, EQ-5D and EQ-5D VAS, and SF-36 Mental Component Summary Score and SF-36 Physical Component Summary Score when compared to placebo. These improvements were maintained in ustekinumab-treated patients in UNIFI-M through week 44.

Patients receiving ustekinumab experienced significantly more improvements in work productivity as assessed by greater reductions in overall work impairment and in activity impairment as assessed by the WPAI-GH questionnaire than patients receiving placebo.

Hospitalizations and Ulcerative Colitis (UC) Related Surgeries

Through week 8 of UNIFI-I, the proportions of subjects with UC disease related hospitalizations were significantly lower for subjects in the ustekinumab recommended dose group (1.6%, 5/322) compared with subjects in the placebo group (4.4%, 14/319) and no subjects underwent UC disease related surgeries in subjects receiving ustekinumab at the recommended induction dose compared to 0.6% (2/319) subjects in the placebo group.

Through week 44 of UNIFI-M, a significantly lower number of UC-related hospitalizations was observed in subjects in the combined ustekinumab group (2.0%, 7/348) as compared with subjects in the placebo group (5.7%, 10/175). A numerically lower number of subjects in the ustekinumab group (0.6%, 2/348) underwent UC disease related surgeries compared with subjects in the placebo group (1.7%, 3/175) through week 44.

Immunogenicity

Antibodies to ustekinumab may develop during ustekinumab treatment and most are neutralising. The formation of anti-ustekinumab antibodies is associated with both increased clearance and reduced efficacy of ustekinumab, except in patients with Crohn's disease or ulcerative colitis where no reduced efficacy was observed. There is no apparent correlation between the presence of anti-ustekinumab antibodies and the occurrence of injection site reactions.

Paediatric Population

The European Medicines Agency has deferred the obligation to submit the results of studies with ustekinumab in one or more subsets of the paediatric population in Crohn's Disease and ulcerative colitis (see section 4.2 for information on paediatric use).

5.2 Pharmacokinetic Properties

Absorption

The median time to reach the maximum serum concentration ($t_{max}$) was 8.5 days after a single 90 mg subcutaneous administration in healthy subjects. The median $t_{max}$ values of ustekinumab following a single subcutaneous administration of either 45 mg or 90 mg in patients with psoriasis were comparable to those observed in healthy subjects.

The absolute bioavailability of ustekinumab following a single subcutaneous administration was estimated to be 57.2% in patients with psoriasis.

Distribution

Median volume of distribution during the terminal phase (Vz) following a single intravenous administration to patients with psoriasis ranged from 57 to 83 mL/kg.

Biotransformation

The exact metabolic pathway for ustekinumab is unknown.

Elimination

Median systemic clearance (CL) following a single intravenous administration to patients with psoriasis ranged from 1.99 to 2.34 mL/day/kg. Median half-life ($t_{1/2}$) of ustekinumab was approximately 3 weeks in patients with psoriasis, psoriatic arthritis, Crohn's disease or ulcerative colitis, ranging from 15 to 32 days across all psoriasis and psoriatic arthritis studies. In a population pharmacokinetic analysis, the apparent clearance (CL/F) and apparent volume of distribution (V/F) were 0.465 l/day and 15.71, respectively, in patients with psoriasis. The CL/F of ustekinumab was not impacted by gender. Population pharmacokinetic analysis showed that there was a trend towards a higher clearance of ustekinumab in patients who tested positive for antibodies to ustekinumab.

Dose Linearity

The systemic exposure of ustekinumab ($C_{max}$ and AUC) increased in an approximately dose-proportional manner after a single intravenous administration at doses ranging from 0.09 mg/kg to 4.5 mg/kg or following a single subcutaneous administration at doses ranging from approximately 24 mg to 240 mg in patients with psoriasis.

Single Dose Versus Multiple Doses

Serum concentration-time profiles of ustekinumab were generally predictable after single or multiple subcutaneous dose administrations. In patients with psoriasis, steady-state serum concentrations of ustekinumab were achieved by week 28 after initial subcutaneous doses at Weeks 0 and 4 followed by doses every 12 weeks. The median steady-state trough concentration ranged from 0.21 µg/mL to 0.26 µg/mL (45 mg) and from 0.47 µg/mL to 0.49 µg/mL (90 mg). There was no apparent accumulation in serum ustekinumab concentration over time when given subcutaneously every 12 weeks.

In patients with Crohn's disease and ulcerative colitis, following an intravenous dose of ~6 mg/kg, starting at week 8, subcutaneous maintenance dosing of 90 mg ustekinumab was administered every 8 or 12 weeks. Steady state ustekinumab concentration was achieved by the start of the second maintenance dose. In patients with Crohn's disease, median steady-state trough concentrations ranged from 1.97 µg/mL to 2.24 µg/mL and from 0.61 µg/mL to 0.76 µg/mL for 90 mg ustekinumab every 8 weeks or every 12 weeks respectively. In patients with ulcerative colitis, median steady-state trough concentrations ranged from 2.69 µg/mL to 3.09 µg/mL and from 0.92 µg/mL to 1.19 µg/mL for 90 mg ustekinumab every 8 weeks or every 12 weeks. The steady-state trough ustekinumab levels resulting from 90 mg ustekinumab every 8 weeks were associated with higher clinical remission rates as compared to the steady-state trough levels following 90 mg every 12 weeks.

Impact of Weight on Pharmacokinetics

In a population pharmacokinetic analysis using data from patients with psoriasis, body weight was found to be the most significant covariate affecting the clearance of ustekinumab. The median CL/F in patients with weight>100 kg was approximately 55% higher compared to patients with weight≤100 kg. The median V/F in patients with weight>100 kg was approximately 37% higher as compared to patients with weight≤100 kg. The median trough serum concentrations of ustekinumab in patients with higher weight (>100 kg) in the 90 mg group were comparable to those in patients with lower weight (≤100 kg) in the 45 mg group. Similar results were obtained from a confirmatory population pharmacokinetic analysis using data from patients with psoriatic arthritis.

Dosing Frequency Adjustment

In patients with Crohn's disease and ulcerative colitis, based on observed data and population PK analyses, randomized subjects who lost response to treatment had lower serum ustekinumab concentrations over time compared with subjects who did not lose response. In Crohn's disease, dose adjustment from 90 mg every 12 weeks to 90 mg every 8 weeks was associated with an increase in trough serum ustekinumab concentrations and an accompanying increase in efficacy. In ulcerative colitis, population PK model based simulations demonstrated that adjusting dosing from 90 mg every 12 weeks to every 8 weeks would be expected to result in a 3-fold increase in steady-state trough ustekinumab concentrations. Additionally on the basis of clinical trial data in patients with ulcerative colitis, a positive exposure-response relationship was established between trough concentrations, and clinical remission and mucosal healing.

Special Populations

No pharmacokinetic data are available in patients with impaired renal or hepatic function. No specific studies have been conducted in elderly patients.

The pharmacokinetics of ustekinumab were generally comparable between Asian and non-Asian patients with psoriasis and ulcerative colitis.

In patients with Crohn's disease and ulcerative colitis, variability in ustekinumab clearance was affected by body weight, serum albumin level, sex, and antibody to ustekinumab status while body weight was the main covariate affecting the volume of distribution. Additionally in Crohn's disease, clearance was affected by C-reactive protein, TNF antagonist failure status and race (Asian versus non-Asian). The impact of these covariates was within ±20% of the typical or reference value of the respective PK parameter, thus dose adjustment is not warranted for these covariates. Concomitant use of immunomodulators did not have a significant impact on ustekinumab disposition.

In the population pharmacokinetic analysis, there were no indications of an effect of tobacco or alcohol on the pharmacokinetics of ustekinumab.

Serum ustekinumab concentrations in paediatric psoriasis patients 12 to 17 years of age, treated with the recommended weight-based dose were generally comparable to those in the adult psoriasis population treated with the adult dose, while serum ustekinumab concentrations in paediatric psoriasis patients treated with half of the recommended weight-based dose were generally lower than those in adults.

Regulation of CYP450 Enzymes

The effects of IL-12 or IL-23 on the regulation of CYP450 enzymes were evaluated in an in vitro study using human hepatocytes, which showed that IL-12 and/or IL-23 at levels of 10 ng/mL did not alter human CYP450 enzyme activities (CYP1A2, 2B6, 2C9, 2C19, 2D6, or 3A4; see section 4.5).

5.3 Preclinical Safety Data

Non-clinical data reveal no special hazard (e.g. organ toxicity) for humans based on studies of repeated-dose toxicity and developmental and reproductive toxicity, including safety pharmacology evaluations. In developmental and reproductive toxicity studies in cynomolgus monkeys, neither adverse effects on male fertility indices nor birth defects or developmental toxicity were observed. No adverse effects on female fertility indices were observed using an analogous antibody to IL-12/23 in mice.

Dose levels in animal studies were up to approximately 45-fold higher than the highest equivalent dose intended to be administered to psoriasis patients and resulted in peak serum concentrations in monkeys that were more than 100-fold higher than observed in humans.

Carcinogenicity studies were not performed with ustekinumab due to the lack of appropriate models for an antibody with no cross-reactivity to rodent IL-12/23 p40.

6. Pharmaceutical Particulars 6.1 List of Excipients

L-histidine

L-histidine monohydrochloride monohydrate

Polysorbate 80

Sucrose

Water for injections 6.2 Incompatibilities

In the absence of compatibility studies, this medicinal product must not be mixed with other medicinal products.

6.3 Shelf life

STELARA 45 mg solution for injection 2 years

STELARA 90 mg solution for injection 2 years

STELARA 45 mg solution for injection in pre-filled syringe 3 years

STELARA 90 mg solution for injection in pre-filled syringe 3 years 6.4 Special Precautions for Storage Store in a refrigerator (2° C.-8° C.). Do not freeze.

Keep the vial or pre-filled syringe in the outer carton in order to protect from light.

6.5 Nature and Contents of Container

STELARA 45 mg Solution for Injection 0.5 mL solution in a type I glass 2 mL vial closed with a coated butyl rubber stopper.

STELARA 90 mg Solution for Injection 1 mL solution in a type I glass 2 mL vial closed with a coated butyl rubber stopper.

STELARA 45 mg Solution for Injection in Pre-Filled Syringe 0.5 mL solution in a type I glass 1 mL syringe with a fixed stainless steel needle and a needle cover containing dry natural rubber (a derivative of latex). The syringe is fitted with a passive safety guard.

STELARA 90 mg Solution for Injection in Pre-Filled Syringe 1 mL solution in a type I glass 1 mL syringe with a fixed stainless steel needle and a needle cover containing dry natural rubber (a derivative of latex). The syringe is fitted with a passive safety guard.

STELARA is available in a 1 vial pack or a pack of 1 pre-filled syringe.

6.6 Special Precautions for Disposal and Other Handling

The solution in the STELARA vial or pre-filled syringe should not be shaken. The solution should be visually inspected for particulate matter or discoloration prior to subcutaneous administration. The solution is clear to slightly opalescent, colourless to light yellow and may contain a few small translucent or white particles of protein. This appearance is not unusual for proteinaceous solutions. The medicinal product should not be used if the solution is discoloured or cloudy, or if foreign particulate matter is present. Before administration, STELARA should be allowed to reach room temperature (approximately half an hour). Detailed instructions for use are provided in the package leaflet.

STELARA does not contain preservatives; therefore any unused medicinal product remaining in the vial and the syringe should not be used. STELARA is supplied as a sterile, single-use vial or single-use pre-filled syringe. The syringe, needle and vial must never be re-used. Any unused medicinal product or waste material should be disposed of in accordance with local requirements.

7. Marketing Authorisation Holder
   Janssen-Cilag International NV
   Turnhoutseweg 30
   2340 Beerse
   Belgium
8. Marketing Authorisation Number(S)
   STELARA 45 mg Solution for Injection
   EU/1/08/494/001
   STELARA 90 mg Solution for Injection
   EU/1/08/494/002
   STELARA 45 mg Solution for Injection in Pre-Filled Syringe
   EU/1/08/494/003
   STELARA 90 mg Solution for Injection in Pre-Filled Syringe
   EU/1/08/494/004
9. Date of First Authorisation/Renewal of the Authorisation
   Date of first authorisation: 16 Jan. 2009
   Date of latest renewal: 19 Sep. 2013
10. Date of Revision of the Text
    Detailed information on this medicinal product is available on the website of the European Medicines Agency http://www.ema.europa.eu/

What is claimed:

1. A method of treating moderately to severely active ulcerative colitis (UC) in a subject in need thereof, comprising administering to the subject a pharmaceutical composition comprising a clinically proven safe and clinically proven effective amount of an anti-IL-12/IL-23p40 antibody, wherein the antibody comprises a heavy chain variable region and a light chain variable region, the heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and the light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6, wherein after treating with the antibody, the subject is a responder to treatment by at least one measure of response to treatment selected from the group consisting of: (i) clinical remission based on at least one of the global definition of clinical remission with Mayo score ≤2 points with no individual subscore >1 and the US definition of clinical remission with absolute stool number ≤3, rectal bleeding subscore of 0 and Mayo endoscopy subscore of 0 or 1, (ii) endoscopic healing with a Mayo endoscopy subscore of 0 or 1, (iii) clinical response based on the Mayo endoscopy subscore, (iv) improvements from baseline in Inflammatory Bowel Disease Questionnaire (IBDQ) score, (v) mucosal healing, (vi) decrease from baseline in Mayo score, and (vii) clinical response as determined by a decrease from baseline in the Mayo score by ≥30% and ≥3 points and a decrease from baseline in the rectal bleeding subscore ≥1 points or a rectal bleeding subscore of 0 or 1.

2. The method of claim 1, wherein the antibody comprises the heavy chain variable region of the amino acid sequence of SEQ ID NO:7 and the light chain variable region of the amino acid sequence of SEQ ID NO:8.

3. The method of claim 1, wherein the antibody comprises a heavy chain of the amino acid sequence of SEQ ID NO:10 and a light chain of the amino acid sequence of SEQ ID NO:11.

4. The method of any one of claims 1-3, wherein the antibody is in a pharmaceutical composition for intravenous administration comprising a solution comprising 10 mM L-histidine, 8.5% (w/v) sucrose, 0.04% (w/v) polysorbate 80, 0.4 mg/mL L-methionine, and 20 µg/mL EDTA disodium salt, dehydrate, at pH 6.0.

5. The method of any one of claims 1-3, wherein the antibody is in a pharmaceutical composition for subcutaneous administration comprising a solution comprising 6.7 mM L-histidine, 7.6% (w/v) sucrose, 0.004% (w/v) polysorbate 80, at pH 6.0.

6. The method of claim 4, wherein the antibody is administered intravenously to the subject at week 0 of the treatment, at a dosage of about 6.0 mg/kg body weight of the subject or 130 mg per administration.

7. The method of claim 6, wherein the antibody is further administered subcutaneously to the subject at week 8 of the treatment, at a dosage of about 90 mg per administration.

8. The method of claim 7, wherein the subject had previously failed or was intolerant of at least one therapy selected from the group consisting of an anti-TNF, vedolizumab, corticosteroids, azathioprine (AZA), and 6 mercaptopurine (6 MP), or the subject had demonstrated corticosteroid dependence.

9. The method of claim 7, wherein the antibody is administered in a maintenance dose every 8 weeks after the treatment at week 8 or every 12 weeks after the treatment at week 8.

10. The method of claim 9, wherein the subject is identified as having a clinical remission based on at least one of the global definition and the US definition by week 16 of the treatment and the clinical remission continues at least 44 weeks after week 0.

11. The method of claim 9, wherein the subject is in corticosteroid-free clinical remission at least 44 weeks after week 0.

12. The method of claim 8, wherein the subject is identified as having an endoscopic healing continuing at least 44 weeks after week 0.

13. The method of claim 9, wherein the subject is identified as achieving a clinical response based on the Mayo endoscopy subscore continuing at least 44 weeks after week 0.

14. The method of claim 9, wherein the subject is identified as having improvements from baseline in Inflammatory Bowel Disease Questionnaire (IBDQ) score continuing at least 44 weeks after week 0.

15. The method of claim 9, wherein the subject is identified as having a mucosal healing continuing at least 44 weeks after week 0.

16. The method of claim 9, wherein the subject identified as having a decrease from baseline in Mayo score continuing at least 44 weeks after week 0.

17. The method of claim 9, wherein the subject is identified as having a normalization of one or more biomarkers selected from the group consisting of C-reactive protein, fecal lactoferrin and fecal calprotectin continuing at least 44 weeks after week 0.

18. The method of claim 9, wherein the subject is in clinical response as determined by a decrease from baseline in the Mayo score by ≥30% and ≥3 points and a decrease from baseline in the rectal bleeding subscore ≥1 points or a rectal bleeding subscore of 0 or 1 continuing at least 44 weeks after week 0.

19. A method of treating moderately to severely active ulcerative colitis (UC) in a subject in need thereof, comprising:
   a. intravenously administering to the subject an anti-IL-12/IL-23p40 antibody in a first pharmaceutical composition at a dosage of about 6.0 mg/kg body weight of the subject or 130 mg per administration at week 0 of the treatment, and
   b. subcutaneously administering to the subject the anti-IL-12/IL-23p40 antibody in a second pharmaceutical composition at a dosage of 90 mg per administration at week 8 of the treatment,
   wherein the antibody comprises a heavy chain variable region and a light chain variable region, the heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and the light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6; and
   wherein the subject is a responder to treatment by at least one measure of response to treatment selected from the group consisting of: (i) having a clinical remission based on at least one of the global definition of clinical remission with Mayo score ≤2 points with no individual subscore >1 and the US definition of clinical remission with absolute stool number ≤3, rectal bleeding subscore of 0 and Mayo endoscopy subscore of 0 or 1, (ii) having an endoscopic healing with a Mayo endoscopy subscore of 0 or 1, (iii) achieving a clinical response based on the Mayo endoscopy subscore, (iv) having improvements from baseline in Inflammatory Bowel Disease Questionnaire (IBDQ) score, (v) having a mucosal healing, (vi) having a decrease from baseline in Mayo score, and (vii) in clinical response as determined by a decrease from baseline in the Mayo score by ≥30% and ≥3 points and a decrease from baseline in the rectal bleeding subscore ≥1 points or a rectal bleeding subscore of 0 or 1, and had previously failed or was intolerant of at least one therapy selected from the group consisting of: an anti-TNF, vedolizumab, corticosteroids, azathioprine (AZA), and 6 mercaptopurine (6 MP), or the subject had demonstrated corticosteroid dependence.

20. The method of claim 19, wherein the antibody comprises the heavy chain variable region of the amino acid sequence of SEQ ID NO:7 and the light chain variable region of the amino acid sequence of SEQ ID NO:8.

21. The method of claim 19, wherein the antibody comprises a heavy chain of the amino acid sequence of SEQ ID NO:10 and a light chain of the amino acid sequence of SEQ ID NO:11.

22. The method of any one of claims 19-21, wherein the pharmaceutical composition for intravenous administration further comprises a solution comprising 10 mM L-histidine, 8.5% (w/v) sucrose, 0.04% (w/v) polysorbate 80, 0.4 mg/mL L-methionine, and 20 µg/mL EDTA disodium salt, dehydrate, at pH 6.0.

23. The method of claim 22, wherein the pharmaceutical composition for subcutaneous administration further comprises a solution comprising 6.7 mM L-histidine, 7.6% (w/v) sucrose, 0.004% (w/v) polysorbate 80, at pH 6.0.

24. The method of any one of claims 19-21, wherein the subject is identified as having a clinical remission based on at least one of the global definition and the US definition by week 16 of the treatment.

25. The method of any one of claims 19-21, wherein the subject is identified as having an endoscopic healing by week 16 of the treatment.

26. The method of any one of claims 19-21, wherein the subject is identified as achieving a clinical response based on the Mayo endoscopy subscore by week 16 of the treatment.

27. The method of any one of claims 19-21, wherein the subject is identified as having improvements from baseline in Inflammatory Bowel Disease Questionnaire (IBDQ) score by week 16 of the treatment.

28. The method of any one of claims 19-21, wherein the subject is identified as having a mucosal healing by week 16 of the treatment.

29. The method of any one of claims 19-21, wherein the subject is identified as having a decrease from baseline in Mayo score by week 16 of the treatment.

30. The method of any one of claims 19-21, wherein the subject is identified as having a normalization of one or more biomarkers selected from the group consisting of C-reactive protein, fecal lactoferrin and fecal calprotectin by week 16 of the treatment.

31. The method of any one of claims 19-21, wherein the subject is in clinical response as determined by a decrease from baseline in the Mayo score by ≥30% and ≥3 points and a decrease from baseline in the rectal bleeding subscore ≥1 points or a rectal bleeding subscore of 0 or 1 by week 16 of the treatment.

32. The method of any one of claims 19-21, wherein the subject is not a responder to the treatment with the antibody by week 8 and is a responder to the treatment by week 16 of the treatment.

33. A method of treating moderately to severely active ulcerative colitis (UC) in a subject in need thereof, comprising:
   a. intravenously administering to the subject an anti-IL-12/IL-23p40 antibody in a first pharmaceutical composition at a dosage of about 6.0 mg/kg body weight of the subject or 130 mg per administration at week 0 of the treatment, and
   b. subcutaneously administering to the subject the anti-IL-12/IL-23p40 antibody in a second pharmaceutical composition at a dosage of 90 mg per administration at week 8 of the treatment,
   wherein the antibody comprises a heavy chain variable region and a light chain variable region, the heavy chain variable region comprising: a complementarity determining region heavy chain 1 (CDRH1) amino acid sequence of SEQ ID NO:1; a CDRH2 amino acid sequence of SEQ ID NO:2; and a CDRH3 amino acid sequence of SEQ ID NO:3; and the light chain variable region comprising: a complementarity determining region light chain 1 (CDRL1) amino acid sequence of SEQ ID NO:4; a CDRL2 amino acid sequence of SEQ ID NO:5; and a CDRL3 amino acid sequence of SEQ ID NO:6, followed by a maintenance therapy,
   wherein the maintenance therapy comprises subcutaneously administering to the subject the anti-IL-12/IL-23p40 antibody at a dosage of 90 mg per administration, once every 8 weeks or once every 12 weeks, and wherein the maintenance therapy is provided for 44 weeks and after treating with the antibody, the subject is a responder to treatment by at least one measure of response to treatment selected from the group consisting of: (i) having a clinical remission based on at least one of the global definition of clinical remission with Mayo score $\leq 2$ points with no individual subscore $>1$ and the US definition of clinical remission with absolute stool number $\leq 3$, rectal bleeding subscore of 0 and Mayo endoscopy subscore of 0 or 1, (ii) having an endoscopic healing with a Mayo endoscopy subscore of 0 or 1, (iii) achieving a clinical response based on the Mayo endoscopy subscore, (iv) having improvements from baseline in Inflammatory Bowel Disease Questionnaire (IBDQ) score, (v) having a mucosal healing, (vi) having a decrease from baseline in Mayo score, and (vii) in clinical response as determined by a decrease from baseline in the Mayo score by $\geq 30\%$ and $\geq 3$ points and a decrease from baseline in the rectal bleeding subscore $\geq 1$ points or a rectal bleeding subscore of 0 or 1.

34. A method of treating moderately to severely active ulcerative colitis (UC) in a subject in need thereof, comprising:
   a. intravenously administering to the subject an anti-IL-12/IL-23p40 antibody comprising a heavy chain variable region of the amino acid sequence of SEQ ID NO:7 and a light chain variable region of the amino acid sequence of SEQ ID NO:8, in a first pharmaceutical composition at a dosage of about 6.0 mg/kg body weight of the subject or 130 mg per administration at week 0 of the treatment, and
   b. subcutaneously administering to the subject the anti-IL-12/IL-23p40 antibody in a second pharmaceutical composition at a dosage of 90 mg per administration at week 8 of the treatment, followed by a maintenance therapy, wherein the maintenance therapy comprises subcutaneously administering to the subject the anti-IL-12/IL-23p40 antibody at a dosage of 90 mg per administration, once every 8 weeks or once every 12 weeks, and after treating with the antibody, the subject is a responder to treatment by at least one measure of response to treatment selected from the group consisting of: (i) having a clinical remission based on at least one of the global definition of clinical remission with Mayo score $\leq 2$ points with no individual subscore $>1$ and the US definition of clinical remission with absolute stool number $\leq 3$, rectal bleeding subscore of 0 and Mayo endoscopy subscore of 0 or 1, (ii) having an endoscopic healing with a Mayo endoscopy subscore of 0 or 1, (iii) achieving a clinical response based on the Mayo endoscopy subscore, (iv) having improvements from baseline in Inflammatory Bowel Disease Questionnaire (IBDQ) score, (v) having a mucosal healing, (vi) having a decrease from baseline in Mayo score, and (vii) in clinical response as determined by a decrease from baseline in the Mayo score by $\geq 30\%$ and $\geq 3$ points and a decrease from baseline in the rectal bleeding subscore $\geq 1$ points or a rectal bleeding subscore of 0 or 1.

\* \* \* \* \*

```
                         SEQUENCE LISTING

<160> NUMBER OF SEQ ID NOS: 11

<210> SEQ ID NO 1
<211> LENGTH: 5
<212> TYPE: PRT
<213> ORGANISM: Artificial Sequence
<220> FEATURE:
<223> OTHER INFORMATION: anti-IL-12/IL-23p40 antibody complementarity
      determining region heavy chain 1

<400> SEQUENCE: 1

Thr Tyr Trp Leu Gly
1               5

<210> SEQ ID NO 2
<211> LENGTH: 17
<212> TYPE: PRT
<213> ORGANISM: Artificial Sequence
<220> FEATURE:
<223> OTHER INFORMATION: anti-IL-12/IL-23p40 antibody complementarity
      determining region heavy chain 2

<400> SEQUENCE: 2

Ile Met Ser Pro Val Asp Ser Asp Ile Arg Tyr Ser Pro Ser Phe Gln
1               5                   10                  15

Gly

<210> SEQ ID NO 3
<211> LENGTH: 10
<212> TYPE: PRT
<213> ORGANISM: Artificial Sequence
<220> FEATURE:
<223> OTHER INFORMATION: anti-IL-12/IL-23p40 antibody complementarity
      determining region heavy chain 3

<400> SEQUENCE: 3

Arg Arg Pro Gly Gln Gly Tyr Phe Asp Phe
1               5                   10

<210> SEQ ID NO 4
<211> LENGTH: 11
<212> TYPE: PRT
<213> ORGANISM: Artificial Sequence
<220> FEATURE:
<223> OTHER INFORMATION: anti-IL-12/IL-23p40 antibody complementarity
      determining region light chain 1

<400> SEQUENCE: 4

Arg Ala Ser Gln Gly Ile Ser Ser Trp Leu Ala
1               5                   10
```

<210> SEQ ID NO 5
<211> LENGTH: 7
<212> TYPE: PRT
<213> ORGANISM: Artificial Sequence
<220> FEATURE:
<223> OTHER INFORMATION: anti-IL-12/IL-23p40 antibody complementarity
      determining region light chain 2

<400> SEQUENCE: 5

Ala Ala Ser Ser Leu Gln Ser
1               5

<210> SEQ ID NO 6
<211> LENGTH: 9
<212> TYPE: PRT
<213> ORGANISM: Artificial Sequence
<220> FEATURE:
<223> OTHER INFORMATION: anti-IL-12/IL-23p40 antibody complementarity
      determining region light chain 3

<400> SEQUENCE: 6

Gln Gln Tyr Asn Ile Tyr Pro Tyr Thr
1               5

<210> SEQ ID NO 7
<211> LENGTH: 119
<212> TYPE: PRT
<213> ORGANISM: Artificial Sequence
<220> FEATURE:
<223> OTHER INFORMATION: anti-IL-12/IL-23p40 antibody variable heavy
      chain region

<400> SEQUENCE: 7

Glu Val Gln Leu Val Gln Ser Gly Ala Glu Val Lys Lys Pro Gly Glu
1               5                   10                  15

Ser Leu Lys Ile Ser Cys Lys Gly Ser Gly Tyr Ser Phe Thr Thr Tyr
            20                  25                  30

Trp Leu Gly Trp Val Arg Gln Met Pro Gly Lys Gly Leu Asp Trp Ile
        35                  40                  45

Gly Ile Met Ser Pro Val Asp Ser Asp Ile Arg Tyr Ser Pro Ser Phe
    50                  55                  60

Gln Gly Gln Val Thr Met Ser Val Asp Lys Ser Ile Thr Thr Ala Tyr
65                  70                  75                  80

Leu Gln Trp Asn Ser Leu Lys Ala Ser Asp Thr Ala Met Tyr Tyr Cys
                85                  90                  95

Ala Arg Arg Arg Pro Gly Gln Gly Tyr Phe Asp Phe Trp Gly Gln Gly
            100                 105                 110

Thr Leu Val Thr Val Ser Ser
        115

<210> SEQ ID NO 8
<211> LENGTH: 108
<212> TYPE: PRT
<213> ORGANISM: Artificial Sequence
<220> FEATURE:
<223> OTHER INFORMATION: anti-IL-12/IL-23p40 antibody variable light
      chain region

<400> SEQUENCE: 8

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp

```
                  20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ile Tyr Pro Tyr
                 85                  90                  95

Thr Phe Gly Gln Gly Thr Lys Leu Glu Ile Lys Arg
             100                 105
```

<210> SEQ ID NO 9
<211> LENGTH: 503
<212> TYPE: PRT
<213> ORGANISM: Artificial Sequence
<220> FEATURE:
<223> OTHER INFORMATION: Human IL-12 with alpha and beta subunits

<400> SEQUENCE: 9

```
Arg Asn Leu Pro Val Ala Thr Pro Asp Pro Gly Met Phe Pro Cys Leu
 1               5                  10                  15

His His Ser Gln Asn Leu Leu Arg Ala Val Ser Asn Met Leu Gln Lys
                 20                  25                  30

Ala Arg Gln Thr Leu Glu Phe Tyr Pro Cys Thr Ser Glu Glu Ile Asp
             35                  40                  45

His Glu Asp Ile Thr Lys Asp Lys Thr Ser Thr Val Glu Ala Cys Leu
         50                  55                  60

Pro Leu Glu Leu Thr Lys Asn Glu Ser Cys Leu Asn Ser Arg Glu Thr
 65                  70                  75                  80

Ser Phe Ile Thr Asn Gly Ser Cys Leu Ala Ser Arg Lys Thr Ser Phe
                 85                  90                  95

Met Met Ala Leu Cys Leu Ser Ser Ile Tyr Glu Asp Leu Lys Met Tyr
             100                 105                 110

Gln Val Glu Phe Lys Thr Met Asn Ala Lys Leu Leu Met Asp Pro Lys
         115                 120                 125

Arg Gln Ile Phe Leu Asp Gln Asn Met Leu Ala Val Ile Asp Glu Leu
130                 135                 140

Met Gln Ala Leu Asn Phe Asn Ser Glu Thr Val Pro Gln Lys Ser Ser
145                 150                 155                 160

Leu Glu Glu Pro Asp Phe Tyr Lys Thr Lys Ile Lys Leu Cys Ile Leu
                165                 170                 175

Leu His Ala Phe Arg Ile Arg Ala Val Thr Ile Asp Arg Val Met Ser
            180                 185                 190

Tyr Leu Asn Ala Ser Ile Trp Glu Leu Lys Lys Asp Val Tyr Val Val
        195                 200                 205

Glu Leu Asp Trp Tyr Pro Asp Ala Pro Gly Glu Met Val Val Leu Thr
    210                 215                 220

Cys Asp Thr Pro Glu Glu Asp Gly Ile Thr Trp Thr Leu Asp Gln Ser
225                 230                 235                 240

Ser Glu Val Leu Gly Ser Gly Lys Thr Leu Thr Ile Gln Val Lys Glu
                245                 250                 255

Phe Gly Asp Ala Gly Gln Tyr Thr Cys His Lys Gly Gly Glu Val Leu
            260                 265                 270

Ser His Ser Leu Leu Leu Leu His Lys Lys Glu Asp Gly Ile Trp Ser
```

```
                    275                 280                 285
Thr Asp Ile Leu Lys Asp Gln Lys Glu Pro Lys Asn Lys Thr Phe Leu
                290                 295                 300
Arg Cys Glu Ala Lys Asn Tyr Ser Gly Arg Phe Thr Cys Trp Trp Leu
305                 310                 315                 320
Thr Thr Ile Ser Thr Asp Leu Thr Phe Ser Val Lys Ser Ser Arg Gly
                325                 330                 335
Ser Ser Asp Pro Gln Gly Val Thr Cys Gly Ala Ala Thr Leu Ser Ala
            340                 345                 350
Glu Arg Val Arg Gly Asp Asn Lys Glu Tyr Glu Tyr Ser Val Glu Cys
        355                 360                 365
Gln Glu Asp Ser Ala Cys Pro Ala Ala Glu Glu Ser Leu Pro Ile Glu
    370                 375                 380
Val Met Val Asp Ala Val His Lys Leu Lys Tyr Glu Asn Tyr Thr Ser
385                 390                 395                 400
Ser Phe Phe Ile Arg Asp Ile Ile Lys Pro Asp Pro Pro Lys Asn Leu
                405                 410                 415
Gln Leu Lys Pro Leu Lys Asn Ser Arg Gln Val Glu Val Ser Trp Glu
            420                 425                 430
Tyr Pro Asp Thr Trp Ser Thr Pro His Ser Tyr Phe Ser Leu Thr Phe
        435                 440                 445
Cys Val Gln Val Gln Gly Lys Ser Lys Arg Glu Lys Lys Asp Arg Val
    450                 455                 460
Phe Thr Asp Lys Thr Ser Ala Thr Val Ile Cys Arg Lys Asn Ala Ser
465                 470                 475                 480
Ile Ser Val Arg Ala Gln Asp Arg Tyr Tyr Ser Ser Ser Trp Ser Glu
                485                 490                 495
Trp Ala Ser Val Pro Cys Ser
            500

<210> SEQ ID NO 10
<211> LENGTH: 449
<212> TYPE: PRT
<213> ORGANISM: Artificial Sequence
<220> FEATURE:
<223> OTHER INFORMATION: anti-IL-12/IL-23p40 antibody heavy chain

<400> SEQUENCE: 10

Glu Val Gln Leu Val Gln Ser Gly Ala Glu Val Lys Lys Pro Gly Glu
1               5                   10                  15
Ser Leu Lys Ile Ser Cys Lys Gly Ser Gly Tyr Ser Phe Thr Thr Tyr
            20                  25                  30
Trp Leu Gly Trp Val Arg Gln Met Pro Gly Lys Gly Leu Asp Trp Ile
        35                  40                  45
Gly Ile Met Ser Pro Val Asp Ser Asp Ile Arg Tyr Ser Pro Ser Phe
    50                  55                  60
Gln Gly Gln Val Thr Met Ser Val Asp Lys Ser Ile Thr Thr Ala Tyr
65                  70                  75                  80
Leu Gln Trp Asn Ser Leu Lys Ala Ser Asp Thr Ala Met Tyr Tyr Cys
                85                  90                  95
Ala Arg Arg Arg Pro Gly Gln Gly Tyr Phe Asp Phe Trp Gly Gln Gly
            100                 105                 110
Thr Leu Val Thr Val Ser Ser Ser Thr Lys Gly Pro Ser Val Phe
        115                 120                 125
Pro Leu Ala Pro Ser Ser Lys Ser Thr Ser Gly Gly Thr Ala Ala Leu
```

```
                130                 135                 140
Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 11
<211> LENGTH: 214
<212> TYPE: PRT
<213> ORGANISM: Artificial Sequence
<220> FEATURE:
<223> OTHER INFORMATION: anti-IL-12/IL-23p40 antibody light chain

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45
```

```
Tyr Ala Ala Ser Ser Leu Gln Ser Gly Val Pro Ser Arg Phe Ser Gly
    50              55                  60

Ser Gly Ser Gly Thr Asp Phe Thr Leu Thr Ile Ser Ser Leu Gln Pro
65              70                  75                  80

Glu Asp Phe Ala Thr Tyr Tyr Cys Gln Gln Tyr Asn Ile Tyr Pro Tyr
                85                  90                  95

Thr Phe Gly Gln Gly Thr Lys Leu Glu Ile Lys Arg Thr Val Ala Ala
            100             105             110

Pro Ser Val Phe Ile Phe Pro Pro Ser Asp Glu Gln Leu Lys Ser Gly
        115             120             125

Thr Ala Ser Val Val Cys Leu Leu Asn Asn Phe Tyr Pro Arg Glu Ala
    130             135             140

Lys Val Gln Trp Lys Val Asp Asn Ala Leu Gln Ser Gly Asn Ser Gln
145             150             155             160

Glu Ser Val Thr Glu Gln Asp Ser Lys Asp Ser Thr Tyr Ser Leu Ser
            165             170             175

Ser Thr Leu Thr Leu Ser Lys Ala Asp Tyr Glu Lys His Lys Val Tyr
            180             185             190

Ala Cys Glu Val Thr His Gln Gly Leu Ser Ser Pro Val Thr Lys Ser
        195             200             205

Phe Asn Arg Gly Glu Cys
    210
```